United States Patent [19]
Ward et al.

[11] Patent Number: 6,165,745
[45] Date of Patent: Dec. 26, 2000

[54] RECOMBINANT PRODUCTION OF IMMUNOGLOBULIN-LIKE DOMAINS IN PROKARYOTIC CELLS

[75] Inventors: E. Sally Ward, Dallas; Jin-Kyoo Kim, Irving, both of Tex.

[73] Assignee: Board of Regents, The University of Texas System, Austin, Tex.

[21] Appl. No.: 08/341,560

[22] Filed: Nov. 17, 1994

Related U.S. Application Data

[63] Continuation-in-part of application No. 07/963,333, Oct. 19, 1992, abandoned, which is a continuation-in-part of application No. 07/873,930, Apr. 24, 1992, abandoned.

[51] Int. Cl.[7] ..................................................... C12P 21/06
[52] U.S. Cl. .................... 435/69.1; 435/71.1; 435/252.3; 436/547
[58] Field of Search ........................... 536/25.3; 435/69.1, 435/71.1, 172.3, 252.3, 317.1, 320.1; 436/547

[56] References Cited

PUBLICATIONS

Waldmann, Science, vol. 252, pp. 1657–1662, Jun. 21, 1991.

*Primary Examiner*—Laurie Scheiner
*Attorney, Agent, or Firm*—Fulbright & Jaworski, LLP

[57] ABSTRACT

Disclosed are recombinant vectors encoding immunoglobulin-like domains and portions thereof, such as T-cell variable domains, antibody Fc-hinge fragments, subfragments and mutant domains with reduced biological half lives. Methods of producing large quantities of such domains, heterodimers, and fusion proteins following expression and secretion by prokaryotic host cells are also reported. Described are single chain T-cell receptors, which are folded into β-pleated sheet structures similar to those of immunoglobulin variable domains; antibody Fc and Fc-hinge domains, which have the same in vivo stability as intact antibodies; and domains engineered to have reduced half lives.

12 Claims, 23 Drawing Sheets

```
  1    /     1                                                    31
GAC   TCA   GTG   ACT   CAG   ACG   GAA   GGT   CAA   GTG   GCC
asp   ser   val   thr   gln   thr   glu   gly   gln   val   ala
 61    /    21                                                    91
CAC   TGC   AAC   TAC   TCA   GCC   TCA   GGG   TAC   CCA   GCT
his   cys   asn   tyr   ser   ala   ser   gly   tyr   pro   ala
121    /    41                                                   151
GAA   GGG   CCA   CAG   TTC   CTC   TTT   AGA   GCC   TCA   AGG
glu   gly   pro   gln   phe   leu   phe   arg   ala   ser   arg
181    /    61                                                   211
TTT   GAA   GCC   ACA   TAC   AAT   AAA   GAA   GCC   ACC   TCC
phe   glu   gln   thr   tyr   asn   lys   glu   ala   thr   ser
241    /    81                                                   271
GAG   TCA   GAC   TCG   GCT   GTG   TAC   TAC   TGC   GCT   CTG
glu   ser   asp   ser   ala   val   tyr   tyr   cys   ala   leu
301    /   101                                                   331
ACT   TTT   GGG   GCT   GGA   ACC   AAA   CTC   ACC   ATT   AAA
thr   phe   gly   ala   gly   thr   lys   leu   thr   ile   lys
361    /   121
TAA
OCH                  (SEQ ID NO: 1)
```

FIG. 5A

```
/    11
CTC TCA GAA GAG GAC TTT CTT ACG ATA
leu ser glu glu asp phe leu thr ile
/    31
CTG TTC TGG TAT GTG CAG TAT CCC GGA
leu phe trp tyr val gln tyr pro gly
/    51
GAC AAA GAG AAA GGA AGC AGC AGA GGG
asp lys glu lys gly ser ser arg gly
/    71
TTC CAC TTG CAG AAA GCC TCA GTG CAA
phe his leu gln lys ala ser val gln
/    91
AGT GAA AAC TAT GGA AAT GAG AAA ATA
ser glu asn tyr gly asn glu lys ile
/   111
CCG GTC ACC CAT CAC CAT CAC CAT CAC
pro val thr his his his his his his
```

FIG. 5B

```
1     /    1                                                     31
GAG  GCT  GCA  GTC  ACC  CAA  AGC  CCA  AGA  AAC  AAG
glu  ala  ala  val  thr  gln  ser  pro  arg  asn  lys
61    /   21                                                    91
TTG  AGC  TGT  AAT  CAG  ACT  AAT  AAC  CAC  AAC  AAC
leu  ser  cys  asn  gln  thr  asn  asn  his  asn  asn
121   /   41                                                    151
CAT  GGG  CTG  AGG  CTG  ATC  CAT  TAT  TCA  TAT  GGT
his  gly  leu  arg  leu  ile  his  tyr  ser  tyr  gly
181   /   61                                                    211
CCT  GAT  GGA  TAC  AAG  GCC  TCC  AGA  CCA  AGC  CAA
pro  asp  gly  tyr  lys  ala  ser  arg  pro  ser  gln
241   /   81                                                    271
GCT  ACC  CCC  TCT  CAG  ACA  TCA  GTG  TAC  TTC  TGT
ala  thr  pro  ser  gln  thr  ser  val  tyr  phe  cys
301   /  101                                                    331
ACG  CTG  TAT  TTT  GGC  TCA  GGA  ACC  AGA  CTG  ACT
thr  leu  tyr  phe  gly  ser  gly  thr  arg  leu  thr
361   /  121
CAC  TAA
his  OCH                      (SEQ ID NO: 3)
```

FIG. 6A

```
        / 11
GTG GCA GTA ACA GGA GGA AAG GTG AGA
val ala val thr gly gly lys val thr
        / 31
ATG TAC TGG TAT CGG CAG GAC ACG GGG
met tyr trp tyr arg gln asp thr gly
        / 51
GCT GGC AGC ACT GAG AAA GGA GAT ATC
ala gly ser thr glu lys gly asp ile
        / 71
GAG AAC TTC TCC CTC ATT CTG GAG TTG
glu asn phe ser leu ile leu glu leu
        / 91
GCC AGC GGT GAT GCG TCG GGA GCA GAA
ala ser gly asp ala ser gly ala glu
        / 111
GTT CTG GTC ACC CAT CAC CAT CAC CAT
val leu val thr his his his his his
```

FIG. 6B

```
1   /    1                                                31
GAC TCA GTG ACT CAG ACG GAA GGT CAA GTG GCC
asp ser val thr gln thr glu gly gln val ala
61  /   21                                                91
CAC TGC AAC TAC TCA GCC TCA GGG TAC CCA GCT
his cys asn tyr ser ala ser gly tyr pro ala
121 /   41                                               151
GAA GGG CCA CAG TTC CTC TTT AGA GCC TCA AGG
glu gly pro gln phe leu phe arg ala ser arg
181 /   61                                               211
TTT GAA GCC ACA TAC AAT AAA GAA GCC ACC TCC
phe glu ala thr tyr asn lys glu ala thr ser
241 /   81                                               271
GAG TCA GAC TCG GCT GTG TAC TAC TGC GCT CTG
glu ser asp ser ala val tyr tyr cys ala leu
301 /   101                                              331
ACT TTT GGG GCT GGA ACC AAA CTC ACC ATT AAA
thr phe gly ala gly thr lys leu thr ile lys
361 /   121                                              391
GGA GGT GGC TCT GGC GGT GGC GGA TCG GAG GCT
gly gly gly ser gly gly gly gly ser glu ala
421 /   141                                              451
GTG GCA GTA ACA GGA GGA AAG GTG ACA TTG AGC
val ala val thr gly gly lys val thr leu ser
481 /   161                                              511
ATG TAC TGG TAT CGG CAG GAC ACG GGG CAT GGG
met tyr trp tyr arg gln asp thr gly his gly
541 /   181                                              571
GCT GGC AGC ACT GAG AAA GGA GAT ATC CCT GAT
ala gly ser thr glu lys gly asp ile pro asp
601 /   201                                              631
GAG AAC TTC TCC CTC ATT CTG GAG TTG CCT ACC
glu asn phe ser leu ile leu glu leu ala thr
661 /   221                                              691
GCC AGC GGT GAT GCG TCG GGA GCA GAA ACG CTG
ala ser gly asp ala ser gly ala glu thr leu
721 /   241                                              751
GTT CTG GTC ACC CAT CAC CAT CAC CAT CAC TAA
val leu val thr his his his his his his OCH
```

FIG. 7A

```
      /   11
CTC TCA GAA GAG GAC TTT CTT ACG ATA
leu ser glu glu asp phe leu thr ile
      /   31
CTG TTC TGG TAT GTG CAG TAT CCC GGA
leu phe trp tyr val gln tyr pro gly
      /   51
GAC AAA GAG AAA GGA AGC AGC AGA GGG
asp lys glu lys gly ser ser arg gly
      /   71
TTC CAC TTG CAG AAA GCC TCA GTG CAA
phe his leu gln lys ala ser val gln
      /   91
AGT GAA AAC TAT GGA AAT GAG AAA ATA
ser glu asn tyr gly asn glu lys ile
      /  111
CCG GTC ACC GGT GGA GGC GGT TCA GGC
pro val thr gly gly gly gly ser gly
      /  131
GCA GTC ACC CAA AGC CCA AGA AAC AAG
ala val thr gln ser pro arg asn lys
      /  151
TGT AAT CAG ACT AAT AAC CAC AAC AAC
cys asn gln thr asn asn his asn asn
      /  171
CTG AGG CTG ATC CAT TAT TCA TAT GGT
leu arg leu ile his tyr ser tyr gly
      /  191
GGA TAC AAG GCC TCC AGA CCA AGC CAA
gly tyr lys ala ser arg pro ser gln
      /  211
CCC TCT CAG ACA TCA GTG TAC TTC TGT
pro ser gln thr ser val tyr phe cys
      /  231
TAT TTT GGC TCA GGA ACC AGA CTG ACT
tyr phe gly ser gly thr arg leu thr
      /  251
```

(SEQ ID NO: 5)

FIG. 7B

```
  1    /    1                                                          31
GAC  TCA  GTG  ACT  CAG  ACG  GAA  GGT  CAA  GTG  GCC
asp  ser  val  thr  gln  thr  glu  gly  gln  val  ala
 61    /   21                                                          91
CAC  TGC  AAC  TAC  TCA  GCC  TCA  GGG  TAC  CCA  GCT
his  cys  asn  tyr  ser  ala  ser  gly  tyr  pro  ala
121    /   41                                                         151
GAA  GGG  CCA  CAG  TTC  CTC  TTT  AGA  GCC  TCA  AGG
glu  gly  pro  gln  phe  leu  phe  arg  ala  ser  arg
181    /   61                                                         211
TTT  GAA  GCC  ACA  TAC  AAT  AAA  GAA  GCC  ACC  TCC
phe  glu  ala  thr  tyr  asn  lys  glu  ala  thr  ser
241    /   81                                                         271
CAG  TCA  GAC  TCG  GCT  GTG  TAC  TAC  TGC  GCT  CTG
glu  ser  asp  ser  ala  val  tyr  tyr  cys  ala  leu
301    /  101                                                         331
ACT  TTT  GGG  GCT  GGA  ACC  AAA  CTC  ACC  ATT  AAA
thr  phe  gly  ala  gly  thr  lys  leu  thr  ile  lys
361    /  121                                                         391
GGA  TCC  GGC  GGT  GGC  GGA  TCG  GAG  GCT  GCA  GTC
gly  ser  gly  gly  gly  gly  ser  glu  ala  ala  val
421    /  141                                                         451
GTA  ACA  GGA  GGA  AAG  GTG  ACA  TTG  AGC  TGT  AAT
val  thr  gly  gly  lys  val  thr  leu  ser  cys  asn
481    /  161                                                         511
TGG  TAT  CGG  CAG  GAC  ACG  GGG  CAT  GGG  CTG  AGG
trp  tyr  arg  gln  asp  thr  gly  his  gly  leu  arg
541    /  181                                                         571
AGC  ACT  GAG  AAA  GGA  GAT  ATC  CCT  GAT  GGA  TAC
ser  thr  glu  lys  gly  asp  ile  pro  asp  gly  tyr
601    /  201                                                         631
TTC  TCC  CTC  ATT  CTG  GAG  TTG  GCT  ACC  CCC  TCT
phe  ser  leu  ile  leu  glu  leu  ala  thr  pro  ser
661    /  221                                                         691
GGT  GAT  GCG  TCG  GGA  GCA  GAA  ACG  CTG  TAT  TTT
gly  asp  ala  ser  gly  ala  glu  thr  leu  tyr  phe
721    /  241
GTC  ACC  CAT  CAC  CAT  CAC  CAT  CAC  TAA
val  thr  his  his  his  his  his  his  OCH
```

FIG. 9A

```
        / 11
CTC TCA GAA GAG GAC TTT CTT ACG ATA
leu ser glu glu asp phe leu thr ile
        / 31
CTG TTC TGG TAT CTG CAG TAT CCC GGA
leu phe trp tyr val gln tyr pro gly
        / 51
GAC AAA GAG AAA GGA AGC AGC AGA GGG
asp lys glu lys gly ser ser arg gly
        / 71
TTC CAC TTG CAG AAA GCC TCA GTG CAA
phe his leu gln lys ala ser val gln
        / 91
AGT GAA AAC TAT GGA AAT GAG AAA ATA
ser glu asn tyr gly asn glu lys ile
        / 111
CCG GGT GGA GGC GGT TCA GGC GGA GGT
pro gly gly gly gly ser gly gly gly
        / 131
ACC CAA AGC CCA AGA AAC AAG GTG GCA
thr gln ser pro arg asn lys val ala
        / 151
CAG ACT AAT AAC CAC AAC AAC ATG TAC
gln thr asn asn his asn asn met tyr
        / 171
CTG ATC CAT TAT TCA TAT GGT GCT GGC
leu ile his tyr ser tyr gly ala gly
        / 191
AAG GCC TCC AGA CCA AGC CAA CAG AAC
lys ala ser arg pro ser gln gln asn
        / 211
CAG ACA TCA GTG TAC TTC TGT GCC AGC
gln thr ser val tyr phe cys ala ser
        / 231
GGC TCA GGA ACC AGA CTG ACT GTT CTG
gly ser gly thr arg leu thr val leu
```

(SEQ ID NO: 7)

FIG. 9B

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 363 base pairs
        (B) TYPE: nucleic acid
        (C) STRANDEDNESS: single
        (D) TOPOLOGY: linear (xi) SEQUENCE DESCRIPTION: SEQ ID NO:1:

```
GACTCAGTGA CTCAGACGGA AGGTCAAGTG GCCCTCTCAG AAGAGGACTT TCTTACGATA      60

CACTGCAACT ACTCAGCCTC AGGGTACCCA GCTCTGTTCT GGTATGTGCA GTATCCCGGA     120

GAAGGGCCAC AGTTCCTCTT TAGAGCCTCA AGGGACAAAG AGAAAGGAAG CAGCAGAGGG     180
```

```
TTTGAAGCCA CATACAATAA AGAAGCCACC TCCTTCCACT TGCAGAAAGC CTCAGTGCAA      240

GAGTCAGACT CGGCTGTGTA CTACTGCGCT CTGAGTGAAA ACTATGGAAA TGAGAAAATA      300

ACTTTTGGGG CTGGAACCAA ACTCACCATT AAACCGGTCA CCCATCACCA TCACCATCAC      360

TAA                                                                    363
```

(2) INFORMATION FOR SEQ ID NO:2:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:2:

```
Asp Ser Val Thr Gln Thr Glu Gly Gln Val Ala Leu Ser Glu Glu
1               5                   10                  15

Phe Leu Thr Ile His Cys Asn Tyr Ser Ala Ser Gly Tyr Pro Ala Leu
            20                  25                  30

Phe Trp Tyr Val Gln Tyr Pro Gly Glu Gly Pro Gln Phe Leu Phe Arg
        35                  40                  45

Ala Ser Arg Asp Lys Glu Lys Gly Ser Ser Arg Gly Phe Glu Ala Thr
    50                  55                  60

Tyr Asn Lys Glu Ala Thr Ser Phe His Leu Gln Lys Ala Ser Val Gln
65                  70                  75                  80

Glu Ser Asp Ser Ala Val Tyr Tyr Cys Ala Leu Ser Glu Asn Tyr Gly
                85                  90                  95

Asn Glu Lys Ile Thr Phe Gly Ala Gly Thr Lys Leu Thr Ile Lys Pro
            100                 105                 110

Val Thr His His His His His His
            115                 120
```

(2) INFORMATION FOR SEQ ID NO:3:

(i) SEQUENCE CHARACTERISTICS:
        (A) LENGTH: 366 base pairs
        (B) TYPE: nucleic acid
        (C) STRANDEDNESS: single
        (D) TOPOLOGY: linear (xi) SEQUENCE DESCRIPTION: SEQ ID NO:3:

```
GAGGCTGCAG TCACCCAAAG CCCAAGAAAC AAGGTGGCAG TAACAGGAGG AAAGGTGACA       60

TTGAGCTGTA ATCAGACTAA TAACCACAAC AACATGTACT GGTATCGGCA GGACACGGGG      120

CATGGGCTGA GGCTGATCCA TTATTCATAT GGTGCTGGCA GCACTGAGAA AGGAGATATC      180

CCTGATGGAT ACAAGGCCTC CAGACCAAGC CAAGAGAACT TCTCCCTCAT TCTGGAGTTG      240

GCTACCCCCT CTCAGACATC AGTGTACTTC TGTGCCAGCG GTGATGCGTC GGGAGCAGAA      300

ACGCTGTATT TTGGCTCAGG AACCAGACTG ACTGTTCTGG TCACCCATCA CCATCACCAT      360

CACTAA                                                                 366
```

(2) INFORMATION FOR SEQ ID NO:4:

(i) SEQUENCE CHARACTERISTICS:
        (A) LENGTH: 121 amino acids
        (B) TYPE: amino acid
        (C) STRANDEDNESS:
        (D) TOPOLOGY: linear (xi) SEQUENCE DESCRIPTION: SEQ ID NO:4:

```
Glu Ala Ala Val Thr Gln Ser Pro Arg Asn Lys Val Ala Val Thr Gly
 1               5                  10                  15

Gly Lys Val Thr Leu Ser Cys Asn Gln Thr Asn Asn His Asn Asn Met
                20                  25                  30

Tyr Trp Tyr Arg Gln Asp Thr Gly His Gly Leu Arg Leu Ile His Tyr
            35                  40                  45

Ser Tyr Gly Ala Gly Ser Thr Glu Lys Gly Asp Ile Pro Asp Gly Tyr
        50                  55                  60

Lys Ala Ser Arg Pro Ser Gln Glu Asn Phe Ser Leu Ile Leu Glu Leu
65                  70                  75                  80

Ala Thr Pro Ser Gln Thr Ser Val Tyr Phe Cys Ala Ser Gly Asp Ala
                85                  90                  95

Ser Gly Ala Glu Thr Leu Tyr Phe Gly Ser Gly Thr Arg Leu Thr Val
            100                 105                 110

Leu Val Thr His His His His His His
            115                 120

(2) INFORMATION FOR SEQ ID NO:5:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (xi) SEQUENCE DESCRIPTION: SEQ ID NO:5:

GACTCAGTGA CTCAGACGGA AGGTCAAGTG GCCCTCTCAG AAGAGGACTT TCTTACGATA      60

CACTGCAACT ACTCAGCCTC AGGGTACCCA GCTCTGTTCT GGTATGTGCA GTATCCCGGA     120

GAAGGGCCAC AGTTCCTCTT TAGAGCCTCA AGGGACAAAG AGAAAGGAAG CAGCAGAGGG     180

TTTGAAGCCA CATACAATAA AGAAGCCACC TCCTTCCACT TGCAGAAAGC CTCAGTGCAA     240

GAGTCAGACT CGGCTGTGTA CTACTGCGCT CTGAGTGAAA ACTATGGAAA TGAGAAAATA     300

ACTTTTGGGG CTGGAACCAA ACTCACCATT AAACCGGTCA CCGGTGGAGG CGGTTCAGGC     360

GGAGGTGGCT CTGGCGGTGG CGGATCGGAG GCTGCAGTCA CCCAAAGCCC AAGAAACAAG     420

GTGGCAGTAA CAGGAGGAAA GGTGACATTG AGCTGTAATC AGACTAATAA CCACAACAAC     480

ATGTACTGGT ATCGGCAGGA CACGGGGCAT GGGCTGAGGC TGATCCATTA TTCATATGGT     540

GCTGGCAGCA CTGAGAAAGG AGATATCCCT GATGGATACA AGGCCTCCAG ACCAAGCCAA     600

GAGAACTTCT CCCTCATTCT GGAGTTGGCT ACCCCCTCTC AGACATCAGT GTACTTCTGT     660

GCCAGCGGTG ATGCGTCGGG AGCAGAAACG CTGTATTTTG GCTCAGGAAC CAGACTGACT     720

GTTCTGGTCA CCCATCACCA TCACCATCAC TAA                                  753

(2) INFORMATION FOR SEQ ID NO:6:

(i) SEQUENCE CHARACTERISTICS:
        (A) LENGTH: 250 amino acids
        (B) TYPE: amino acid
        (C) STRANDEDNESS:
        (D) TOPOLOGY: linear (xi) SEQUENCE DESCRIPTION: SEQ ID NO:6:

Asp Ser Val Thr Gln Thr Glu Gly Gln Val Ala Leu Ser Glu Glu Asp
 1               5                  10                  15

Phe Leu Thr Ile His Cys Asn Tyr Ser Ala Ser Gly Tyr Pro Ala Leu
                20                  25                  30
```

-continued

```
Phe Trp Tyr Val Gln Tyr Pro Gly Glu Gly Pro Gln Phe Leu Phe Arg
         35                  40                  45

Ala Ser Arg Asp Lys Glu Lys Gly Ser Ser Arg Gly Phe Glu Ala Thr
 50                  55                  60

Tyr Asn Lys Glu Ala Thr Ser Phe His Leu Gln Lys Ala Ser Val Gln
 65                  70                  75                  80

Glu Ser Asp Ser Ala Val Tyr Tyr Cys Ala Leu Ser Glu Asn Tyr Gly
                 85                  90                  95

Asn Glu Lys Ile Thr Phe Gly Ala Gly Thr Lys Leu Thr Ile Lys Pro
                100                 105                 110

Val Thr Gly Gly Gly Gly Ser Gly Gly Gly Gly Ser Gly Gly Gly Gly
                115                 120                 125

Ser Glu Ala Ala Val Thr Gln Ser Pro Arg Asn Lys Val Ala Val Thr
130                 135                 140

Gly Gly Lys Val Thr Leu Ser Cys Asn Gln Thr Asn Asn His Asn Asn
145                 150                 155                 160

Met Tyr Trp Tyr Arg Gln Asp Thr Gly His Gly Leu Arg Leu Ile His
                165                 170                 175

Tyr Ser Tyr Gly Ala Gly Ser Thr Glu Lys Gly Asp Ile Pro Asp Gly
                180                 185                 190

Tyr Lys Ala Ser Arg Pro Ser Gln Glu Asn Phe Ser Leu Ile Leu Glu
                195                 200                 205

Leu Ala Thr Pro Ser Gln Thr Ser Val Tyr Phe Cys Ala Ser Gly Asp
210                 215                 220

Ala Ser Gly Ala Glu Thr Leu Tyr Phe Gly Ser Gly Thr Arg Leu Thr
225                 230                 235                 240

Val Leu Val Thr His His His His His
                245                 250
```

(2) INFORMATION FOR SEQ ID NO:7:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (xi) SEQUENCE DESCRIPTION: SEQ ID NO:7:

```
GACTCAGTGA CTCAGACGGA AGGTCAAGTG GCCCTCTCAG AAGAGGACTT TCTTACGATA      60

CACTGCAACT ACTCAGCCTC AGGGTACCCA GCTCTGTTCT GGTATGTGCA GTATCCCGGA     120

GAAGGGCCAC AGTTCCTCTT TAGAGCCTCA AGGGACAAAG AGAAAGGAAG CAGCAGAGGG     180

TTTGAAGCCA CATACAATAA AGAAGCCACC TCCTTCCACT TGCAGAAAGC CTCAGTGCAA     240

GAGTCAGACT CGGCTGTGTA CTACTGCGCT CTGAGTGAAA ACTATGGAAA TGAGAAAATA     300

ACTTTTGGGG CTGGAACCAA ACTCACCATT AAACCGGGTG GAGGCGGTTC AGGCGGAGGT     360

GGATCCGGCG GTGGCGGATC GGAGGCTGCA GTCACCCAAA GCCCAAGAAA CAAGGTGGCA     420

GTAACAGGAG GAAAGGTGAC ATTGAGCTGT AATCAGACTA ATAACCACAA CAACATGTAC     480

TGGTATCGGC AGGACACGGG GCATGGGCTG AGGCTGATCC ATTATTCATA TGGTGCTGGC     540

AGCACTGAGA AAGGAGATAT CCCTGATGGA TACAAGGCCT CCAGACCAAG CCAAGAGAAC     600

TTCTCCCTCA TTCTGGAGTT GGCTACCCCC TCTCAGACAT CAGTGTACTT CTGTGCCAGC     660

GGTGATGCGT CGGGAGCAGA AACGCTGTAT TTTGGCTCAG GAACCAGACT GACTGTTCTG     720

GTCACCCATC ACCATCACCA TCACTAA                                         747
```

(2) INFORMATION FOR SEQ ID NO:8:

(i) SEQUENCE CHARACTERISTICS:
        (A) LENGTH: 248 amino acids
        (B) TYPE: amino acid
        (C) STRANDEDNESS:
        (D) TOPOLOGY: linear (xi) SEQUENCE DESCRIPTION: SEQ ID NO:8:

```
Asp Ser Val Thr Gln Thr Glu Gly Gln Val Ala Leu Ser Glu Glu Asp
1               5                   10                  15

Phe Leu Thr Ile His Cys Asn Tyr Ser Ala Ser Gly Tyr Pro Ala Leu
            20                  25                  30

Phe Trp Tyr Val Gln Tyr Pro Gly Glu Gly Pro Gln Phe Leu Phe Arg
        35                  40                  45

Ala Ser Arg Asp Lys Glu Lys Gly Ser Ser Arg Gly Phe Glu Ala Thr
    50                  55                  60

Tyr Asn Lys Glu Ala Thr Ser Phe His Leu Gly Lys Ala Ser Val Gly
65                  70                  75                  80

Glu Ser Asp Ser Ala Val Tyr Tyr Lys Ala Leu Ser Glu Asn Tyr Gly
                85                  90                  95

Asn Glu Lys Ile Thr Phe Gly Ala Gly Thr Lys Leu Thr Ile Lys Pro
            100                 105                 110

Gly Gly Gly Gly Ser Gly Gly Gly Ser Gly Gly Gly Gly Ser Glu
        115                 120                 125

Ala Ala Val Thr Gly Ser Pro Arg Asn Lys Val Ala Val Thr Gly Gly
    130                 135                 140

Lys Val Thr Leu Ser Lys Asn Gly Thr Asn Asn His Asn Asn Met Tyr
145                 150                 155                 160

Trp Tyr Arg Gly Asp Thr Gly His Gly Leu Arg Leu Ile His Tyr Ser
                165                 170                 175

Tyr Gly Ala Gly Ser Thr Glu Lys Gly Asp Ile Pro Asp Gly Tyr Lys
            180                 185                 190

Ala Ser Arg Pro Ser Gly Glu Asn Phe Ser Leu Ile Leu Glu Leu Ala
        195                 200                 205

Thr Pro Ser Gly Thr Ser Val Tyr Phe Lys Ala Ser Gly Asp Ala Ser
    210                 215                 220

Gly Ala Glu Thr Leu Tyr Phe Gly Ser Gly Thr Arg Leu Thr Val Leu
225                 230                 235                 240

Val Thr His His His His His
                245
```

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:9:

ATCACCATGG CCGGCAGACC GAAGGCTCCA CAG                          33

(2) INFORMATION FOR SEQ ID NO:10:

(i) SEQUENCE CHARACTERISTICS:
        (A) LENGTH: 34 base pairs
        (B) TYPE: nucleic acid
        (C) STRANDEDNESS: single (D) TOPOLOGY: linear (xi) SEQUENCE DESCRIPTION: SEQ ID NO:10:

TACAGGTGAC CTTACCAGGA GAGTGGGAGA GGCT                                34

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:11:

ATCACCATGG CCGTGCCCAG GGATTGTGGT TG                                  32

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:12:

ATCAGGTGAC CTTGGTTTTG GAGATGGTTT T                                   31

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

ATCACCATGG CCGAAGTATC ATCTGTCTTC ATC                                 33

(2) INFORMATION FOR SEQ ID NO:14:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:14:

ATCTACACGT GACCTTAGGA GTCAGAGTAG CGGTGAG                             37

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:15:

GAGCCAGTCG TTGGCCATGA TGGGAAG                                        27

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:16:

AGTATGGTGT TGGGCCAGGC CCTCATG                                       27

(2) INFORMATION FOR SEQ ID NO:17:

(i) SEQUENCE CHARACTERISTICS:
        (A) LENGTH: 445 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 1
        (D) OTHER INFORMATION: /note= "Xaa = Pca (PCA:
            pryollidonecarboxylic acid)"

(xi) SEQUENCE DESCRIPTION: SEQ ID NO:17:

```
Xaa Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Arg Ser
            20                  25                  30

Ala Ile Ile Trp Val Arg Gln Ala Pro Gly Gln Gly Leu Glu Trp Met
        35                  40                  45

Gly Gly Ile Val Pro Met Phe Gly Pro Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Gly Gly Tyr Gly Ile Tyr Ser Pro Glu Glu Tyr Asn Gly Gly Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Gln
            260                 265                 270

Val Lys Phe Asn Trp Tyr Val Asp Gly Val Gln Val His Asn Ala Lys
        275                 280                 285

Thr Lys Pro Arg Glu Gln Gln Tyr Asx Ser Thr Tyr Arg Val Val Ser
290                 295                 300
```

```
Val Leu Thr Val Leu His Gln Asn Trp Leu Asp Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Asp Gly Glu Pro Glu Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Pro Gly
            435                 440                 445

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:18:

ATCCTTCCAT GGCCGACTCA GTGACTCAGA CGGAAGGT                                    38

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:19:

AAGGATGGTG ACCGGTTTAT TGGTGAGTTT GGTTCC                                      36

(2) INFORMATION FOR SEQ ID NO:20:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:20:

ATCCTTCCAT GGCCGAGGCT GCAGTCACCC AAAGTCCA                                    38

(2) INFORMATION FOR SEQ ID NO:21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:21:

AAGGATGGTG ACCAGAACAG TCAGTCTGGT TCCTGA                                      36
```

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:22:

```
GAACAAAAAC TCATCTCAGA AGAGGATCTG AAT                                33
```

(2) INFORMATION FOR SEQ ID NO:23:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:23:

```
Glu Gln Lys Leu Ile Ser Glu Glu Asp Leu Asn
1               5                   10
```

(2) INFORMATION FOR SEQ ID NO:24:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:24:

```
CTGCAGTCTA GAGTCGACCT CGAGGGTCAC C                                  31
```

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:25:

```
GGCCATGGCT GGTTGGG                                                  17
```

(2) INFORMATION FOR SEQ ID NO:26:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:26:

```
ATGAAATACC TATTGCCTAC GGCAGCCGCT GGATTGTTAT TACTCGCTGC CCAACCAGCG   60

ATGGCC                                                              66
```

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:27:

AGCTGAATTC 10

(2) INFORMATION FOR SEQ ID NO:28:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:28:

GTCACCGGTG GAGGCGGTTC AGGCGGAGGT GGCTCTGGCG GTGGCGGATC GGAGGCTGCA 60

(2) INFORMATION FOR SEQ ID NO:29:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:29:

GCCACCTCCG CCAAGTCCGC CTCCACCGAG ACCGCCACCG CCTAGCCTCC G 51

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:30:

GTCACCCATC ACCATCACCA TCACTAATAA 30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:31:

GGTAGTGGTA GTGGTAGTGA TTATTCAGTG 30

(2) INFORMATION FOR SEQ ID NO:32:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:32:

GTATCTGCAG CCTCCGATCC GCCACCGCCG GATCCACCT 39

-continued (2) INFORMATION FOR SEQ ID NO:33:

(i) SEQUENCE CHARACTERISTICS:
  (A) LENGTH: 45 base pairs
  (B) TYPE: nucleic acid
  (C) STRANDEDNESS: single
  (D) TOPOLOGY: linear (xi) SEQUENCE DESCRIPTION: SEQ ID NO:33:

ATCAGGATCC ACCTCCGCCT GAACCGCCTC CACCCGGTTT AATGG    45

RECOMBINANT PRODUCTION OF IMMUNOGLOBULIN-LIKE DOMAINS IN PROKARYOTIC CELLS

This is a continuation-in-part of U.S. patent application Ser. No. 07/963,333, filed Oct. 19, 1992, now abandoned; which is a continuation-in-part of U.S. patent application Ser. No. 07/873,930, filed Apr. 24, 1992, now abandoned. The entire text of each of the above-referenced disclosures is specifically incorporated by reference herein without disclaimer.

The U.S. Government owns certain rights in the present invention pursuant to NIH grant R29 AI31592-01.

BACKGROUND OF THE INVENTION

1. Field of the Invention

The present invention relates generally to the fields of immunology and molecular biology. The invention relates to vectors useful for the expression of immunoglobulin-like domains and fragments, such as T-cell variable domains and wild type and engineered antibody Fc fragments; to bacterial cells capable of secreting said domains, engineered domains, heterodimers and fusion proteins in large quantities; to recombinant domains, fusion proteins or other engineered proteins which have modified in vivo stability; and to methods for their production and use.

2. Description of Related Art

Most glycoproteins that mediate antigen recognition or cell—cell recognition in the immune system contain related structural elements, suggesting that they share a common evolutionary history. Such genes and the resultant protein elements are thus members of an evolutionary conserved group, which has been termed the immunoglobulin (Ig) superfamily. Included in the immune system branch of the immunoglobulin superfamily are antibodies, T cell receptors, MHC glycoproteins, the CD2, CD4 and CD8 proteins, some of the polypeptide chains of the CD3 complex associated with the T cell receptor, various Fc receptors on lymphocytes and other white blood cells, and $\beta_2$-microglobulin.

All of the above molecules contain one or more immunoglobulin (Ig)-like domains which exhibit considerable structural homology. Each immunoglobulin-like domain typically has about 100 amino acids and is thought to be folded into a characteristic structure with two antiparallel $\beta$ sheets, usually stabilized by a conserved disulfide bond. Many of these molecules are dimers or higher oligomers in which Ig homology units of one chain interact with those in another. Other key molecules which contain immunoglobulin-like domains have also been identified, these include receptors such as the PDGF receptor, and cell adhesion molecules such as N-CAM and Ng-CAM.

The majority of T cells recognize antigenic peptides bound to class I or II proteins of the major histocompatibility complex (MHC) and are thus "MHC restricted". The recognition of peptide-MHC complexes is mediated by surface-bound T cell receptors (TCRs). These receptors are comprised of various heterodimeric polypeptides, the majority of which are $\alpha$ and $\beta$ polypeptides. A minor population (1–10%) of mature T-cells bears T-cell receptors (TCRs) comprising $\delta$ $\gamma$ heterodimers (Borst et al., 1987; Brenner et al., 1986).

The production of single or heterodimeric T-cell receptor variable domains is of interest for purposes of studying T-cell receptor interaction with antigens and developing approaches to therapies for autoimmune diseases and cancer. An important goal of molecular biology is a detailed understanding at the molecular level of the binding of T-cell receptors to cognate peptide-major histocompatibility complexes. Detailed knowledge of this process will be a step in the development of, for example, immunotherapy for T-cell mediated autoimmune disease. Despite this interest and the potential applications arising from the study of T-cell receptor domains, no methods are available for the production of only single T-cell receptor domains, nor has expression and secretion in prokaryotic hosts been successful.

Several composite dimeric species incorporating the $\alpha$ and $\beta$ polypeptides have been produced in various systems. TCR $\alpha\beta$ heterodimers have been expressed as phosphatidylinositol linked polypeptides (Lin et al., 1990) or TCR-immunoglobulin chimeras (Gregoire et al., 1991) in mammalian transfectomas. The production of $V_\alpha C\kappa$ homodimers (Mariuzza & Winter, 1989) and $V\beta$-$C\beta$ monomers (Gascoigne, 1990) in mammalian cells has also been described. The expression and secretion of immunoglobulin VH domains (Ward et al., 1989), Fv fragments (Skerra and Pluckthum, 1988; Ward et al., 1989) and Fab fragments (Better et al., 1988) has been reported. Molecular modeling analyses indicate that there are structural similarities between immunoglobulin $F_{ab}$ fragments and the extracellular domains of TCRs (Novotny et al., 1986; Chothia et al., 1988). Several expression systems for the production of recombinant TCRs in mammalian cell transfectomas have been documented but successful expression and secretion of these proteins in a prokaryotic host has not been reported.

Despite apparent expression of a single chain anti-fluorescein TCR in *E. coli* (Novotny et al., 1991), the product could not be isolated from the periplasm even though the leader sequence had been cleaved from the N-terminus of the recombinant protein. The single chain TCR was relatively insoluble, requiring the use of genetic manipulation to replace five of the "exposed" hydrophobic residues with relatively hydrophilic residues.

No methods are presently available for the production of single or heterodimeric T-cell receptor variable domains as secreted proteins. If available, such species would have potential use in the induction of antibodies as protective vaccines, for the therapy of autoimmune disease, and antibodies for targeting idiotypes (T-cell) or T-cell leukemias. Additionally, secretion of T-cell receptor domains from bacterial cell hosts should provide a convenient, economically attractive and rapid route for production of recombinant T-cell receptors.

Immunoglobulin Fc domains are also of great interest for purposes of studying the mechanisms of antibody stabilization, catabolism and antibody interactions with further molecules of the immune system. These include, depending on the class of antibody, interactions with complement, and binding to specific receptors on other cells, including macrophages, neutrophils and mast cells. More detailed knowledge of the biology of Fc regions would be important in understanding various molecular processes of the immune system, such as phagocytosis, antibody-dependent cell-mediated cytotoxicity and allergic reactions.

In an analogous situation to the T cell receptor, methods do not currently exist which allow the production of large quantities of functional individual Fc domains. To date, it is not known whether an immunoglobulin fragment, let alone a stable one, could be produced in a prokaryotic cells such as an *E. coli*. Therefore, methods for the recombinant production of such domains in prokaryotic cells, and particularly, methods resulting in the secretion of large quantities of antibody constant domains would be advantageous.

The production and purification of Fc domains would allow their structural and functional properties to be more precisely defined, and ultimately, precise interactive residues identified which control various functions, such as, e.g., catabolism. The production of a stable Fc fragment that has reduced binding to Fc receptors and complement factors would be attractive, since such a fragment could be used to tag therapeutic reagents. Chimaeric proteins produced in this manner would have the advantage of high stability and in addition, would not bind significantly to Fc receptors that are expressed on a wide variety of immune cells (Hogg, 1988). This would reduce the non-specific binding of the therapeutic reagents, since Fc receptors are ubiquitously expressed. This, in turn, allows lower doses of the agent to be used in therapy and also reduces undesirable side-effects due to non-specific binding.

TCR fragments have been produced in mammalian cells but they are relatively large. Whole antibodies have also been produced recombinantly. However, the availability of smaller size immunoglobulin-like segments may allow more rapid structural resolution using such techniques as NMR and X-ray crystallography. TCR variable domains interact with peptide-MHC complexes and are of considerable interest, antibody constant domains are also of interest given their wide variety of functions. The availability of purified individual domains will allow the functions of residues within such proteins to be defined.

Additionally, the use of variable domains alone in immunization should result in the production of anti-variable domain antibodies. Such antibodies are expected to be particularly desirable for use in therapy and diagnosis since they block the interaction of the TCR with antigen and, due to the variable nature of the $V_\alpha/V_\beta$ domains or other domains such as $V_\delta$ and $V_\gamma$, are specific for subsets of T-cells. Large TCR fragments, such as those that can be expressed from mammalian cells, result in production of antibodies not only against the variable domains, but also against other domains present in the construct, such as TCR constant domains and/or other immunoglobulin domains. There would therefore be distinct advantages in having smaller variable domain TCR fragments available, particularly for immunization since any immune response generated is likely to be directed to particular regions of interest, i.e., the V domains.

SUMMARY OF THE INVENTION

The present invention seeks to address these and other drawbacks in the prior art by providing compositions and methods for the expression and secretion of large quantities of immunoglobulin-like domains, such as T-cell receptor variable domains and native or engineered mutant antibody Fc fragments, in prokaryotic host cells. As such, the invention encompasses recombinant vectors, bacterial cells transformed by such vectors, immunoglobulin-like domains, fragments and conjugates, and to methods for their production and use. The invention also concerns the production of immunoglobulin-like domains, or other recombinant proteins, with increased or decreased stability in vivo, for use, for example, as therapeutic or imaging agents.

As used herein, the term "immunoglobulin-like domain" is intended to refer to a native or engineered domain from the immunoglobulin (Ig), or immunoglobulin-like, superfamily. The immunoglobulin-like superfamily is a well documented group of evolutionary conserved and structurally related proteins. Included in the immunoglobulin superfamily are cell surface and secreted antibodies (immunoglobulins), including IgG, IgM, IgA, IgD and IgE, and various cell surface receptor molecules. The cell surface receptors include T cell receptor chains; class I and class II MCH glycoproteins (also termed HLA antigens); the CD2, CD4 and CD8 proteins; certain CD3 polypeptides; Fc receptors, the Thy-1 molecule; the PDGF receptor; and various cell adhesion molecules (CAMs), such as neural cell and neuron-glia cell adhesion molecules (N-CAM and Ng-CAM, respectively).

Immunoglobulin-like domains may additionally be defined as constant or variable domains. The variable domains may be characterized by the presence of hypervariable loops, changes in the residues of which provide the wide antigen-binding capacity of the immune system. Constant domains do not express such hypervariability as they are not primarily involved in antigen-related interactions. As used herein, "immunoglobulin-like domain" is intended to include all such variable and constant domains, IG-like domains derived originally from antibodies or from cell surface receptors or other molecules, in addition to engineered, modified or 'mutant' forms of such domains.

Despite the presence or absence of hypervariable loops, immunoglobulin-like domains all exhibit common structural motifs. For example, they will each generally have on the order of about 100 amino acids, and will have a similar overall structure including antiparallel β sheets, usually stabilized by a conserved disulfide bond. The structural similarity is important as it renders the present invention applicable to all such immunoglobulin-like domains. Accordingly, the methods of the present invention may be adapted for use in the recombinant production of any immunoglobulin-like domain in a stable form and in large quantities. Naturally, one may wish to modify the particular expression conditions employed, such as buffers, temperatures, and the like, to optimize the yields in each case. Techniques for monitoring and optimizing recombinant production will be known to those of skill in the art in light of the present disclosure.

The present invention is exemplified by the production, and secretion, of large quantities of both variable region and constant region immunoglobulin-like domains, and genetically engineered mutant domains, in gram-negative hosts such as *E. coli* and *S. marcescens*. Also included are examples of the production of immunoglobulin-like domains derived originally from both a cell surface receptor and an antibody molecule. In particular, the production of single TCR variable domains, $V_\alpha$ and $V_\beta$, and single chain $V_\alpha V_\beta$ heterodimers; antibody Fc-hinge, Fc, CH2-hinge and CH3 domains; and Fc-hinge mutant domains with reduced half lives, is disclosed. However, in light of such wide-ranging examples, which cover the spectrum of the immunoglobulin-like superfamily and modifications thereof, it will be understood that the present invention is not limited to these examples alone. Rather, it encompasses all the immunoglobulin-like structures described herein above.

A particularly advantageous aspect of this invention is that it allows the production of large quantities, such as milligrams per liter of bacterial culture, of immunoglobulin-like domains in prokaryotes. Domains produced following expression from the recombinant vectors of the present invention do not suffer from the problems often associated with prokaryotic expression, such as, for example, protein aggregation in inclusion bodies. In fact, the immunoglobulin-like domains of the present invention exhibit native structural forms. For example, recombinant single chain T-cell receptor variable domains are disclosed which are folded into the β-pleated sheets indicative of native structure.

In certain embodiments, recombinantly produced antibody Fc and Fc-hinge domains are described which have the same in vivo stability as intact antibodies. One of the advantages of these proteins is that they are aglycosylated and have a reduced ability to bind to Fc receptors and complement factors. Thus, the construction of chimaeric molecules that contain a therapeutic hormone, for example, linked to the Fc fragment (or subfragment) are expected to have the advantages of increased stability in vivo without the undesirable non-specific binding properties that the native Fc fragment would have. Furthermore, the production of chimaeric proteins in prokaryotic hosts such as *E. coli* rather than in mammalian cells reduces the problems associated with proteolysis, since, in contrast to mammalian cell expression hosts, protease deficient stains of *E. coli* exist and are readily available. The stability of the Fc-based proteins may thus be exploited in the creation of recombinant fusion proteins with enhanced stability, as would may be used in a variety of therapeutic regimens in which the protein must remain stable whilst in the bloodstream.

In other important embodiments, the design and production of recombinant antibody Fc-hinge domains engineered to have reduced in vivo, or biological, half lives is disclosed. The Fc-hinge domain mutants with reduced biological half lives of the present invention are generally defined as mutants in which one or more of the natural residues at the CH2–CH3 domain interface of the Fc-hinge fragment have been exchanged for distinct amino acids, and such Fc-hinge domain mutants may also be functionally defined as mutants which exhibit impaired SpA (Staphylococcal protein A) binding. In preferred embodiments, the reduced half-life Fc-hinge mutants will have changes in certain amino acids between about residue 253 and about residue 434, which have been discovered to form a 'catabolic control site'.

More particularly, the present invention concerns mutant domains and antibodies containing domains in which one or more of the following amino acids have been exchanged for other residues: isoleucine (ile) at position 253; histidine (his) at position 310; glutamine (gln) at position 311; histidine (his) at position 433; and asparagine (asn) at position 434 (wherein the amino acids are numbered according to Kabat et al., (1991)). To reduce the half life of an Fc-hinge domain, or intact antibody, any of the above residues may be substituted for any other amino acid residue. The choice of substitution is not believed to be particularly critical so long as the original ile, his, gln or asn residues are replaced. Substitution can advantageously be achieved by any of the molecular biological techniques known to those of skill in the art, as exemplified hereinbelow, or even by chemical modification.

Preferred reduced half-life antibodies or domains will be those which include one or more of the following substitutions on the Kabat numbering system, or their equivalents on different numbering systems: ile 253 to ala 253; his 310 to ala 310; gln 311 to asn 311; his 433 to ala 433; and asn 434 to gin 434; of which the ile 253 to ala 253, his 310 to ala 310, and gln 311 to asn 311 mutations are particularly preferred. The most preferred mutant domains are the single mutant termed I-253, the double mutant termed HQ-310, and the tetra-mutant termed HQ-310/HN-433 (Table II).

The production of Fc-hinge domains with decreased vivo half lives is an advantageous development in that it marks the delineation of the site for the control of IgG1 catabolism to a specific region of the Fc-hinge fragment, and in practical terms, it has several important applications. It allows the design and construction of antibody molecules, domains, or fragments, such as bivalent Fab fragments, with reduced half lives. These would be generally useful in that the quicker biological clearance times would result in reduced immunogenicity of any antibody administered. The catabolic site delineated in this invention is distinct from the ADCC and complement fixing sites. This is important as antibodies may be produced which are completely functional and yet which have shorter half lives and reduced antigenicity themselves. Other important use include, for example, in antibody-based imaging regimens, antibody-based drug removal, or even in the creation of immunotoxins with shorter lives.

The Fc-hinge domain mutants may also be employed in embodiments other than those involving clinical administration, for example, in the isolation of receptors involved in IgG catabolism. To this end, one may use screening assays or differential screening assays in which the mutants would exhibit binding or increased binding to a potential catabolic receptor.

The discoveries of the present inventors concerning antibody catabolism are also envisioned to be useful, in a reverse-engineering manner, to increase the in vivo half life of virtually any recombinant protein, and particularly a recombinant antibody, which one desires to administer to a human or animal. An antibody or recombinant protein that was found to be cleared from the body more quickly than ideally desired could be engineered to remove certain catabolism-directing residues, such as any one of the residues identified herein.

In certain other embodiments, the present invention contemplates the creation of recombinant molecules, particularly antibody constructs, including imaging antibodies and immunotoxins, with decreased in vivo half lives. Although longevity of recombinant molecules is often needed, several protocols would benefit from the design of a molecule which would be more quickly removed from circulation after exerting its designed action. This may include, for example, antibodies employed for imaging; antibodies administered for the purpose of binding pathogens, toxins or drugs and thereby removing them from the body; and even certain immunotoxins which may quickly bind to their intended target and yet be removed from circulation before they are able to bind significantly to other related targets, thereby reducing toxic side effects.

To generate a domain, antibody or antibody construct with a reduced half-life, one would modify the natural residues at the CH2–CH3 domain interface of the Fc-hinge which form the 'catabolic control site'. Several such catabolism controlling mutations are described herein which may be straightforwardly engineered into an antibody molecule or antibody conjugate. These include, substituting another residue for isoleucine 253, histidine 310, glutamine 311, histidine 433, and/or asparagine 434 (Kabat et al., (1991). The present invention also provides an advantageous method for determining other catabolically important residues, which is based upon identifying a mutant with impaired SpA binding. Therefore, in addition to the specific mutations described herein, mutations which result in decrease SpA binding are contemplated to also result in reduced biological half life and to thus fall within the scope of this invention. Techniques for conducting SpA binding assays are known to those of skill in the art and are also described hereinbelow.

The recombinant plasmids or expression vectors of this invention are adapted for expression of immunoglobulin-like domains, such as T-cell receptor and antibody domains, in recombinant host cells, and particularly, in transformed prokaryotic host cells. Recombinant plasmids thus comprise a DNA segment coding for one or more immunoglobulin-like domains. Accordingly, any one or more of a wide variety of immunoglobulin-like domains may be incorporated into a recombinant vector and expressed in a host cell, and preferably, a prokaryotic cell, in accordance herewith. As discussed above, these include, for example, variable or constant domains from IgG, IgM, IgA, IgD, IgE, T cell receptors, MHC class I or MHC class II, and also, CD2, CD4, CD8, CD3 polypeptides, Fc receptors, Thy-1 and domains from the PDGF receptor, N-CAM or Ng-CAM.

In certain embodiments, the present invention concerns the expression and production of T cell receptor variable domains or antibody constant domains. Preferred TCR variable domains are $V_\alpha$ and $V_\beta$, with the murine T-cell receptor domain $V_\alpha V_\beta$ heterodimer, derived from the 1934.4 hybridoma (Wraith et al., 1989), being particularly preferred. In regard to constant domains, the production of antibody Fc-hinge, Fc, CH2-hinge or CH3 domains is preferred, with Fc-hinge or Fc domains being particularly preferred due to their in vivo stability.

In other instances, the production of Fc-hinge domains (or antibodies incorporating such domains) with mutations at ile 253, his 310, gln 311, his 433 or asn 434 is preferred as these have specifically reduced half lives. Such mutants are exemplified by HN-433, and more preferably, by I-253, HQ-310 and HQ-310/HN-433.

Various segments or subfragments of any of the above domains, as well as other variable or constant domains, may also be employed in accordance herewith. These domains include, for example, the TCR domains $V_\delta V_\gamma$, $C_\alpha$, $C_{\beta 1}$, $C_{\beta 2}$, $C_\delta$, $C_\gamma$, and immunoglobulin domains CH1. Variations of TCR or immunoglobulin domains other than those specifically described above also fall within the scope of the invention. Such variations may arise from naturally-occurring or genetically engineered mutations, such as point mutations, and other alterations affecting one or more amino acids or the addition of amino acids at the N or C termini.

Furthermore, while the invention has been illustrated with murine T-cell receptors and immunoglobulin fragments, similar strategies are applicable to immunoglobulin-like domains from a variety of other species, including mammals such as rat, and more particularly, human immunoglobulin-like molecules. In light of the structural similarity of the immunoglobulin-like domains, and the conservation of the immunoglobulin superfamily throughout evolution, it is contemplated that the techniques of the present invention will be directly applicable to the prokaryotic expression and recombinant production of an immunoglobulin-like domain from any given species.

Other DNA segments may also be included linked to the immunoglobulin-like domains described. For example, one or more recombinant TCR variable domains of varying specificities may be linked to one or more TCR constant domains, immunoglobulin constant domains, or even other proteins, such as bacteriophage coat protein genes. The antibody constant domains of the present invention may also be combined with another TCR or immunoglobulin domain, or indeed, with any other protein. The immunoglobulin constant domains may be variously expressed as a single domain, such as a CH3 domain; or in combination with one, two, three or more domains, such as, for example, as a CH2-hinge domain, an Fc domain, or an entire Fc-hinge domain. In particular embodiments, discussed in more detail below, Fc or Fc-hinge domains may be linked to any protein to produce a recombinant fusion with enhanced biological stability, or certain mutants may be employed to create antibodies or fusion proteins with reduced half lives.

Once expressed, any of the products herein could be radiolabeled or fluorescently labeled, or attached to solid supports, including sepharose or magnetic beads or synthetic bilayers such as liposomes. The products could also be linked to carrier proteins such as bovine serum albumin. The TCR V domains, or V domains in combination with other proteins such as constant domains, could also be linked synthetically to co-receptors such as the extracellular domains of CD4 or CD8. This could increase the avidity of the interaction of the TCR fragment with cognate peptide MHC complexes.

Recombinant, or cloning, vectors are included in one aspect of the present invention. Such vectors and DNA constructs will be useful not only for directing protein expression, but also as for use as templates for in vitro mutagenesis. Vectors will generally include a leader sequence, preferably pelB (Better et al., 1988), although other leader sequences may be used, for example, alkaline phosphatase (phoA) or ompA. In a preferred embodiment, the pelB leader segment is modified with a unique restriction site, such as NcoI, allowing insertion of TCR variable domain genes. Introduction of such restriction sites is a convenient means of cloning in a DNA segment in the same reading frame as the leader sequence.

Modification of the leader sequence DNA may be achieved by altering one or more nucleotides employing site-directed mutagenesis. In general, the technique of site specific mutagenesis is well known in the art as exemplified by publications (Carter, et al., 1985; Sambrook et al., 1989). As will be appreciated, the technique typically employs a phage vector which exists in both a single stranded and double stranded form. Typical vectors useful in site directed mutagenesis include vectors such as the M13 phage (Messing, et al., 1981). These phage are readily commercially available and their use is generally well known to those skilled in the art.

Site directed mutagenesis in accordance herewith is performed by first obtaining a single stranded vector which includes within its sequence the DNA sequence encoding a leader sequence, pelB being used herewith. An oligonucleotide primer bearing the desired mutated sequence is prepared, generally synthetically, for example by the method of Narang et al., (1980). The primer is annealed with the single stranded vector and subjected to DNA polymerizing enzymes such as the *E. coli* polymerase I Klenow fragment. In order to complete the synthesis of the mutation bearing strand, a heteroduplex is formed wherein one strand encodes the original non-mutated sequence and the second strand bears the desired mutation. The heteroduplex may be transformed into a bacterial cell, with *E. coli*. and *S. marcescens* being preferred. Clones are screened using colony hybridization and radiolabeled mutagenic oligonucleotide to identify colonies which contain the mutated plasmid DNA (Carter et al., 1985). Site directed mutagenesis is particularly suitable for generating reduced half life mutants.

Constructs may also include a "tag" useful for isolation and purification of the expressed and secreted polypeptide product. Tags are relatively short DNA segments fused in-frame with a sequence encoding a desired polypeptide, such as the TCR variable domains herein described, which have the function of facilitating detection, isolation and purification. For example, affinity peptides may be encoded by the segments, allowing isolation by selective binding to specific antibodies or affinity resins. Any of a number of tags may be used, including the c-myc tag, $(his)_6$ tag, decapeptide tag (Huse et al., 1989), Flag™ (Immunex) tags and so forth. A number of the tags are also useful for the detection of expressed protein using Western blotting (Ward et al., 1989; Towbin et al., 1978).

(His)$_6$ tags, for example, are preferable for purifying secreted polypeptide products on affinity metal chromatography columns based on metals such as Ni$^{2+}$. The (his)$_6$ peptide chelates Ni$^{2+}$ ions with high affinity. Polypeptide products containing these residues at the N or C termini bind to the affinity columns, allowing polypeptide impurities and other contaminants to be washed away as part of the purification process. Polypeptide products can then be eluted from the column with high efficiency using, for example, 250 mM imidazole.

Peptide tags, or linkers, may also be incorporated into the TCR product. For single chain TCR fragments, preferred linker peptides include a 15-mer, for example, (gly$_4$ser)$_3$, or other linkers, such as those described in Filpula and Whitlow (1991).

As mentioned above, recombinant vectors of the present invention may also include DNA segments encoding various other proteins. In particular, it is envisioned that recombinant vectors encoding antibody Fc-hinge or Fc domains may also include DNA segments encoding other proteins, or fragments thereof, particularly where one wishes to produce the protein in a more stable form. It is envisioned that the stability of proteins or peptides intended for administration to animals or humans may be increased in this manner. Examples of such proteins include, for example, interleukin-2, interleukin-4, γ-interferon, insulin, and the like, and even TCR V$_\alpha$V$_\beta$. A variety of drugs could, likewise, be stabilized in this manner. Equally, the present invention provides methods by which any antibody, fusion protein or drug may be produced in a less stable form, to facilitate its removal from circulation.

DNA segments encoding such proteins may be operatively incorporated into a recombinant vector, in frame with the Fc-based domain, whether upstream or downstream, in a position so as to render the vector capable of expressing a protein:Fc domain fusion protein (or a protein:Fc-hinge domain fusion protein). Techniques for the manipulation of DNA segments in this manner, for example, by genetic engineering using restriction endonucleases, will be known to those of skill in the art in light of both the present disclosure and references such as Sambrook et al. (1989).

The invention has been illustrated with prokaryotic host cells, but this is not meant to be a limitation. The prokaryotic specific promoter and leader sequences described herein may be easily replaced with eukaryotic counterparts. It is recognized that transformation of host cells with DNA segments encoding any of a number of immunoglobulin-like domains will provide a convenient means of producing fully functional proteins, such as for example, functional TCRs. Both cDNA and genomic sequences are suitable for eukaryotic expression, as the host cell will, of course, process the genomic transcripts to yield functional mRNA for translation into protein. Reduced half life mutant domains and antibodies may be produced in eukaryotic systems which fix complement, mediate ADCC and are also cleared from the body quickly.

It is similarly believed that almost any eukaryotic expression system may be utilized for the expression of immunoglobulin-like domains, e.g., baculovirus-based, glutamine synthase based or dihydrofolate reductase-based systems could be employed. Plasmid vectors would incorporate an origin of replication and an efficient eukaryotic promoter, as exemplified by the eukaryotic vectors of the PCMV series, such as pCMV5.

For expression in this manner, one would position the coding sequences adjacent to and under the control of the promoter. It is understood in the art that to bring a coding sequence under the control of such a promoter, one positions the 5' end of the translation initiation site of the translation reading frame of the protein between about 1 and about 50 nucleotides "downstream" of (i.e., 3' of) the chosen promoter.

Where eukaryotic expression is contemplated, one will also typically desire to incorporate into the transcriptional unit, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As used herein the term "engineered" or "recombinant" cell is intended to refer to a cell into which a recombinant gene, such as a gene encoding an immunoglobulin-like domain, has been introduced. Therefore, engineered cells are distinguishable from naturally occurring cells which do not contain a recombinant gene that is introduced by transfection or transformation techniques. Engineered cells are thus cells having a gene or genes introduced through the hand of man. Recombinantly introduced genes will either be in the form of a cDNA (i.e., they will not contain introns), a copy of a cDNA gene, genomic DNA (with or without introns; for expression in prokaryotic hosts, the DNA should be without introns), or will include DNA sequences positioned adjacent to a promoter not naturally associated with the particular introduced gene.

Generally speaking, it may be more convenient to employ as the recombinant gene a cDNA version of the gene. It is believed that the use of a cDNA gene will provide advantages in that the size of the gene is generally much smaller and more readily employed to transform (or transfect) a targeted cell than a genomic gene, which will typically be up to an order of magnitude larger than the cDNA gene. However, the inventor does not exclude the possibility of employing a genomic version of a particular gene where desired, for expression in mammalian cells. For prokaryotic host cells, constructs without introns will be used, since prokaryotes do not splice introns and exons into functional mRNA.

Suitable host cells useful in the practice of the invention include gram-negative organisms and might include *Serratia marcescens*, *Salmonella typhimurium* and similar species. A particularly preferred host cell is *Escherichia coli* and the several variants of *E. coli* that are readily available and well known to those of skill in the art.

A particular aspect of the invention is a method for the production of immunoglobulin-like domains, such as, TCR variable domains, native or mutant antibody constant domains, or subfragments or fusion proteins thereof. To produce such domains or modified domains, a gram-negative microorganism host cell is first transformed with any of the disclosed recombinant vectors, and then cultured in an appropriate bacterial culture medium under conditions to allow expression of the immunoglobulin-like domain(s), which may be subsequently isolated.

Culturing typically comprises growing and induction. Growing is conveniently performed in such media as Luria broth plus 1% glucose, 4×TY (double strength 2×TY) plus 1% glucose, minimal media plus casamino acids and 5% w/v glycerol with temperatures in the range of 20° C. to about 37° C., preferably between 25–30° C. In preferred embodiments, the media will contain a selection agent, such as ampicillin at a concentration of 0.1–1 mg/ml; to select bacterial cells which contain the expression plasmid. Naturally, one will choose a particular selection agent in conjunction with the plasmid construct originally employed, as is known to those of skill in the art.

Induction of expression is typically performed at a point after growth has been initiated, usually after 12–16 hours at 30° C. This length of time results in the cells being in the early stationary phase at the induction stage. If the growth media contains glucose, the cells are pelleted and washed prior to addition of an inducer, such as isopropylthiogalactopyranoside (IPTG) at a concentration of 0.1–1 mM, since glucose inhibits induction of expression. Again, a variety of other inducers may be employed, according to the vector construct originally used, as is known in the art. Cells may be grown for shorter periods prior to induction, for example for 6–10 hours, or to the mid-exponential stage of growth. Cells are induced for 5–28 hours. 5–6 hours of induction is a preferred induction time if the protein is to be isolated from the periplasm, since longer induction times result in the protein leaking into the culture supernatant. However, it may be desirable to isolate product from the external medium, in which case one would prefer using longer induction times. Temperatures in the range of 20° C. to 37° C. may be used as growth and induction temperatures, with 25° C. being a preferred induction temperature.

Isolating polypeptide products produced by the microbial host cell and located in the periplasmic space typically involves disrupting the microorganism, generally by such means as osmotic shock, sonication or lysis. Once cells are disrupted, cells or cell debris may be conveniently removed by centrifugation or filtration, for example. The proteins may be further purified, for example, by affinity metallic resin chromatography when appropriate peptide tags are attached to the polypeptide products.

Alternatively, if the induction period is longer than 8 hours (at 25° C., for example), so that the protein leaks into the culture supernatant, cells may be removed from the culture by centrifugation and the culture supernatant filtered and concentrated (for example, 10–20 fold). Concentrated supernatant is then dialyzed against phosphate buffered saline and separation achieved by column chromatography, such as affinity or adsorption chromatography. An example is separation through $Ni^{2+}$-NTA-agarose to separate appropriately tagged proteins such as those carrying a $(his)_6$ tag. When these tags are used in the construction of an expression vector, histidine tags are particularly preferred as they facilitate isolation and purification on metallic resins such as $Ni^{+2}$- NTA agarose.

The native sequence antibody Fc-hinge and Fc antibody constant domains of the present invention are herein shown to have the same in vivo stability as a native antibody. Accordingly, the present invention further encompasses a method by which to produce a protein with increased stability, by coupling it to one or more Fc-hinge or Fc domains. This is contemplated to be applicable to any protein which one desires to have increased stability, and particularly, to proteins which one desires to exhibit increased biological stability, such as an increased serum half life.

As used herein, the term "biologically stable protein" is intended to refer to a protein which has been modified resulting in increased biological stability with respect to the original protein. This term encompasses both known recombinant proteins and also proteins for which the recombinant form has not yet been reported. As such, increased or decreased biological stability may be measured with respect to the known or original recombinant protein, or with respect to the native protein. Biological stability may be measured by a variety of in vitro or in vivo means, for example, by using a radiolabeled protein and measuring levels of serum radioactivity as function of time, or by assaying the levels of intact antibody (of known specificity) present in the serum using ELISA as a function of time, with a particularly preferred measure of increased biological stability being evidenced by increased serum half life and decreased clearance rates.

To produce a biologically stable recombinant protein in which the protein in question is linked to an antibody Fc-hinge domain or an antibody Fc domain, in accordance herewith, one would first prepare a recombinant vector capable of expressing a protein:Fc-hinge or protein:Fc domain fusion protein in a gram-negative host, as described hereinabove. One would then insert the recombinant vector into a gram-negative bacterium and culture the bacterium under conditions effective to allow the expression of the fusion protein. Following this, one may then proceed to isolate the fusion protein so produced, for example, using the methods of the present invention.

The above method is proposed for use in the generation of a series of therapeutic compounds with improved biological stability. Such compounds include, for example, interleukin-2, insulin, interleukin-4 and interferon gamma, or even TCR $V_\alpha V_\beta$. The recombinant Fc domains of this invention are also contemplated to be of use in stabilizing a wide range of drugs, which would likely alleviate the need for their repeated administration. However, the present methods are not limited solely to the production of proteins for human administration, and may be employed to produce large quantities of any protein with increased stability, such as may be used in, for example, in immunization protocols, in animal treatment by veterinarians, or rodent in viva therapy models.

Several mutant Fc-hinge domains have been generated by the inventors and are herein shown to have dramatically reduced in vivo half lives in comparison to native domains. The present invention therefore further encompasses methods by which to produce antibodies or proteins with decreased biological half lives. These methods include, firstly, coupling a protein or an antibody variable domain to a reduced half life mutant domain of the present invention, as described above. To produce such antibodies or proteins one would prepare a recombinant vector capable of expressing the desired fusion or mutated protein, insert the vector into a gram-negative bacterium, culture it to allow expression and isolate the antibody or protein so produced. These techniques are applicable to any antibody or protein which one desires to have a decreased biological half life, including imaging antibodies and immunotoxins.

Another method of the invention, particularly suited to producing antibodies with decreased biological half lives, is to simply modify a given antibody at one of the catabolizing-controlling residues disclosed herein. This may be achieved chemically, or preferably, by site-directed mutagenesis and recombinant production using any known production method. The resultant modified antibody may be assayed for SpA binding as a preliminary screen. Antibodies engineered in this manner may be single antibodies, domains, Fab fragments, or antibody conjugates such as immunotoxins and antibodies used for diagnostic imaging regimens.

Also contemplated within the scope of the invention are recombinant immunoglobulin-like domain products, such as variable or constant antibody domains; antibodies, antibody constructs, antibody domains or immunotoxins with reduced half lives; T cell receptor domains; or domains from MHC molecules or cell signalling molecules such as CD2, CD4, CD8, CD3, N-CAM or Ng-CAM, or PDGF receptor domains, or fragments thereof. In preferred embodiments, these will include TCR variable domain products, such as single chain heterodimers comprising the variable domains $V_\alpha$, $V_\beta$, $V_\gamma$ and $V_\delta$; antibody constant domain products, such as Fc-hinge, Fc, CH2-hinge and CH3 domains; and antibody Fc-hinge domains engineered to have reduced in vivo half lives, such as, for example, the domains of Table II, and particularly those termed I-253, HQ-310 and HQ-310/HN-433. It will be appreciated that modification and changes may be made in the composition of these domains, for example by altering the underlying DNA, and still obtain a molecule having like or otherwise desirable characteristics. As such, biological functional equivalents of these immunoglobulin-like domains and mutants are also included within the scope of the present invention.

In general, certain amino acids may be substituted for other amino acids in a protein structure without appreciable loss of interactive binding capacity with structures such as, for example, antigen-binding regions of antibodies or receptor sites. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventor that various changes may be made in the coding sequences of immunoglobulin-like domains without appreciable loss of the biological utility or activity of the encoded protein. It may even be possible to change particular residues in such domains to enhance their biological utility or to increase their interactive capability, for example, by increasing the binding affinity of TCR variable domains for cognate peptide MHC complex.

In making such changes, the hydropathic index of amino acids may be considered. The importance of the hydropathic amino acid index in conferring interactive biologic function on a protein is generally understood in the art (Kyte & Doolittle, 1982). It is known that certain amino acids may be substituted for other amino acids having a similar hydropathic index or score and still retain a similar biological activity. Each amino acid has been assigned a hydropathic index on the basis of its hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

It is believed that the relative hydropathic character of the amino acid may play a role in determining the secondary structure of the resultant protein, which in turn defines the interaction of the protein with other molecules, for example, other components of the immune system such as receptors, antibodies and antigens; or other enzymes, substrates, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred. It is also conceivable that it may be possible to increase the binding affinity of immunoglobulin-like domains by changing an amino acid to another which is quite different in hydrophobicity. This may not have an adverse effect on the structure of the protein, particularly where variable domains are concerned, since the most interactive residues are believed to be located in more exposed hypervariable loops.

Substitution of like amino acids can also be made on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (-0.5±1); threonine (-0.4); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4). It is understood that an amino acid can be substituted for another having a similar hydrophilicity value and still, although not always, obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

As illustrated herein, transformed *E. coli* host cells will provide particularly good yields of immunoglobulin-like domains. The yields obtained are in the order of about 1–2 mg/L for $V_\alpha$; 0.1–0.2 mg/L for $V_\beta$; 0.5–1 mg/L for the single chain $V_\alpha V_\beta$ heterodimer; 2 mg/L for CH3; 1–1.5 mg/L for CH2-hinge; 1.5–2 mg/L for Fc; and 0.5–1 mg/L for Fc-hinge. It is contemplated that such values may be readily scaled up to produce relatively large quantities of these domains in a matter of days, employing, for example, a $(his)_6$ tag for affinity purification with the $Ni^{2+}$-NTA-agarose. Thus the expression system will provide a ready supply of immunoglobulin-like domain proteins which may be obtained in a relatively cost-effective manner.

The present invention shows that scTCR (from $V_\alpha$ and $V_\beta$) derived from the 1934.4 T-cell hybridoma (Wraith et al., 1989) is secreted into the periplasm and may be purified in yields of approximately 0.5–1 mg/L culture using $Ni^{2+}$-

NTA-agarose. FIG. 10 shows an SDS polyacrylamide gel analysis of the purification of this protein. For the scTCR in particular, lower growth and induction temperatures of 25–30° C. resulted in higher expression yields. Even higher expression may be achieved with modifications to growth medium and temperature, as recognized by those of skill in the art. For example, lower growth and induction temperatures were found to enhance expression of other recombinant proteins in *E. coli* (Takagi et al., 1988).

Purification of immunoglobulin-like domains, such as TCR variable domains, native antibody constant domains, or Fc-hinge domains with reduced half lives, may be achieved in many ways, including chromatography, density gradient centrifugation and electrophoretic methods. A particular example of scTCR purification employs an affinity column, made by linking the monoclonal antibody KJ16 (specific for murine $V_\beta 8$: Kappler et al., 1988) to sepharose. For the 1934.4 derived scTCR, purification with this affinity column indicated that the epitope recognized by this monoclonal antibody is in the correct conformational state in the recombinant scTCR.

The present invention facilitates the large scale production of immunoglobulin-like domains, including those derived from human sources, which may be employed in a wide variety of embodiments. These include, their use in in vitro mutagenesis studies and in high resolution structural analyses, such as NMR and X-ray crystallography. Fc-hinge and Fc domain analyses have allowed the region involved in antibody catabolism to be delineated, showing that residues ile 253, his 310, gln 311, his 433 and asn 434 are important. Recombinant $V_\alpha$, $V_\beta$, $V_\delta$, $V_\gamma$, single chain $V_\alpha V_\beta$ fragments, domains, or even subfragments thereof, may be used for mapping the TCR residues which are functionally important in binding peptide-MHC complexes. Residues of recombinant TCR fragments may be altered, prior to expression as soluble proteins as disclosed herein, or on the surface of bacteriophage (McCafferty et al., 1990), and mutants binding with higher affinity to peptide-MHC complexes may be screened, or selected for, using solid surfaces coated with antigen presenting cells and cognate peptide. Such higher affinity mutants would have a large number of applications, for example, in therapy of autoimmune disease as blocking reagents. Linking the engineered mutants to native Fc or Fc-hinge domains would have the further advantage of extending the in vivo half lives of the TCR $V_\alpha$, $V_\beta$ domains, thus generating blocking reagents that are stable in vivo.

Any of the immunoglobulin-like domains of the present invention may also be used in immunization protocols for the generation of anti-clonotypic antibodies, useful, for example, in passive immunization for the treatment of disease. As an example, TCRs expressed on the surface of leukemic T-cells could be expressed as soluble domains and used in immunization to generate anti-TCR antibodies. Such antibodies could be used as targeting reagents in the therapy of T-cell leukemias. It is also envisioned that soluble TCRs, as derived from pathogenic T cells, may be used in vaccination to generate a specific anti-TCR response in vivo for the therapy of autoimmune diseases in a similar way to that reported using peptides derived from TCR V-regions (Vandenbark, et al., 1989; Howell, et al., 1989; Offner, et al., 1991).

U.S. Pat. No. 4,554,101 (Hopp, incorporated herein by reference) also teaches the identification and preparation of epitopes from primary amino acid sequences on the basis of hydrophilicity. Through the methods disclosed in Hopp, one of skill in the art would be able to identify epitopes from within an amino acid sequence, such as, e.g., a sequence from a TCR molecule associated with a leukemic or pathogenic T cell. They would then be able to produce domains incorporating the most antigenic regions by means of the advantageous methods of the present invention.

In addition to employing T cell receptor technology in relation to T cell mediated autoimmune diseases and T cell leukemias, the large scale production of immunoglobulin Fc-hinge or Fc domains linked to other proteins or drugs also has potential for immunotherapy. In certain embodiments, chimaeric proteins or drugs may be produced which have the advantage of prolonged half lives and, since aglycosylated Fc has very low binding affinity for Fc receptors, they would not bind to the large number of immune cells that bear these receptors. This is a significant advantage since it reduces non-specific binding. Such Fc fragments will also not fix complement and, importantly, this would likely reduce the occurrence of local inflammatory reactions.

BRIEF DESCRIPTION OF THE DRAWINGS

FIGS. 5A and 5B. Nucleic acid (seq id no:1) and derived amino acid sequence (seq id no:2) of $V_\alpha$ TCR gene with the $(his)_6$ tag.

FIGS. 6A and 6B. Nucleic acid (seq id no:3) and derived amino acid sequence (seq id no:4) of $V_\beta$ TCR gene with the $(his)_6$ tag.

FIGS. 7A and 7B. Nucleic acid (seq id no:5) and derived amino acid sequence (seq id no:6) of scV$_\alpha$V$_\beta$ with the $(his)_6$ tag.

FIGS. 9A and 9B. Nucleic acid (seq id no:7) and derived amino acid sequence (seq id no:8) of scV$_\alpha$V$_\beta$pelBhis ver. 2.

Lane 1: molecular weight markers (with sizes shown on the left margin in kDa; lane 2, osmotic shock fraction of *E. coli* harboring V$_\alpha$pelBhis; lane 3, flow through from V$_\alpha$pelBhis osmotic shock fraction after passage through Ni$^{2+}$-NTA agarose column: lane 4, purified V$_\alpha$ domain; lanes 5–7, same as lanes 2–4 respectively, except that *E. coli* harbors V$_\beta$pelBhis; lanes 8–10, same as lanes 2–4, respectively except that *E. coli* harbors scV$_\alpha$V$_\beta$pelBhis.

Figure 11A:
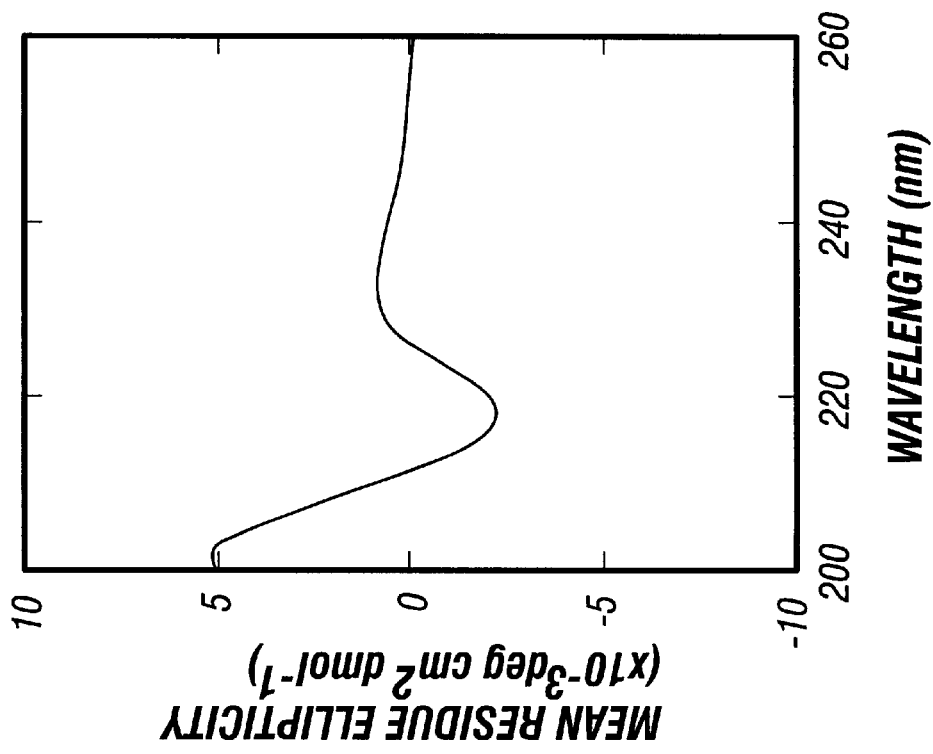
Figure 11B:
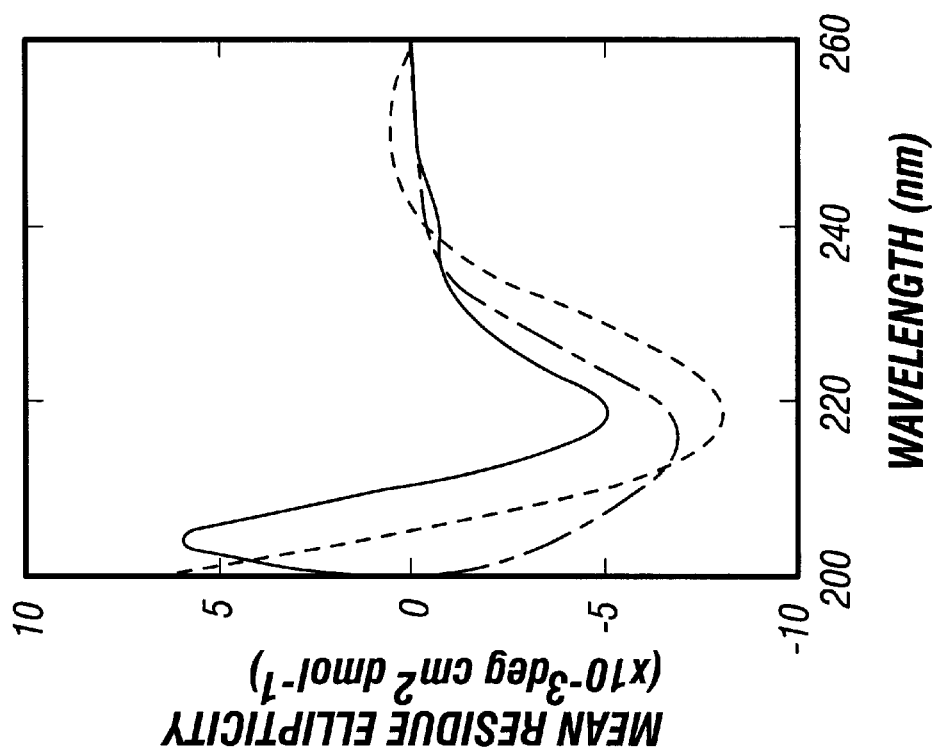
Figure 12A:
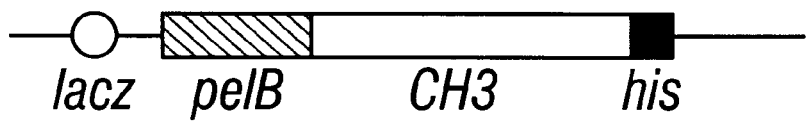
Figure 12B:
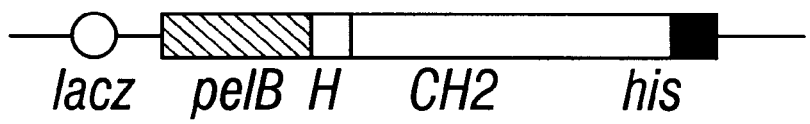
Figure 12C:
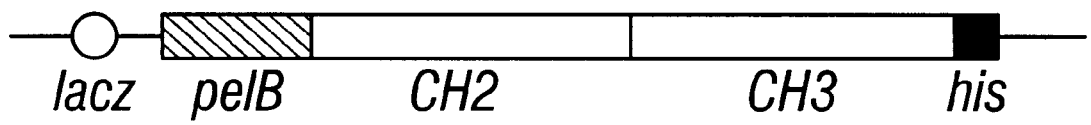
Figure 12D:
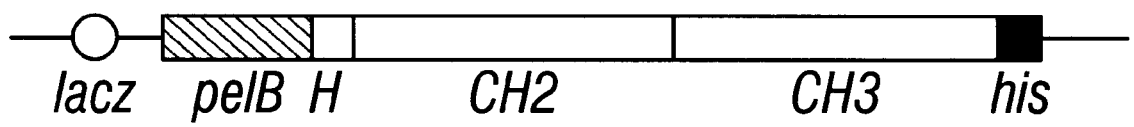

FIGS. 11A and 11B. Circular dichroism spectra for the recombinant TCR proteins. FIG. 11A: spectrum for the V$_\alpha$ domain is represented by a solid line; V$_\beta$ by a broken line; and scTCR by a dashed and dotted line. FIG. 11B: spectrum for the D1.3 scFv fragment. All spectra were smoothed and baseline corrected.

FIGS. 12A, 12B, 12C, and 12D. Schematic representation of portions of the plasmids used for the expression and secretion of immunoglobulin constant region fragments in *E. coli*. a) CH3 domain; b) CH2-hinge; c) Fc fragment and d) Fc-hinge fragments. The lacz promoter is represented by open circles, the pelB leader by hatched boxes, the immunoglobulin domains [hinge region (H) and CH2, CH3 domains] by open boxes and the his$_6$ peptide tag (his) by filled-in boxes.

Figure 13A:
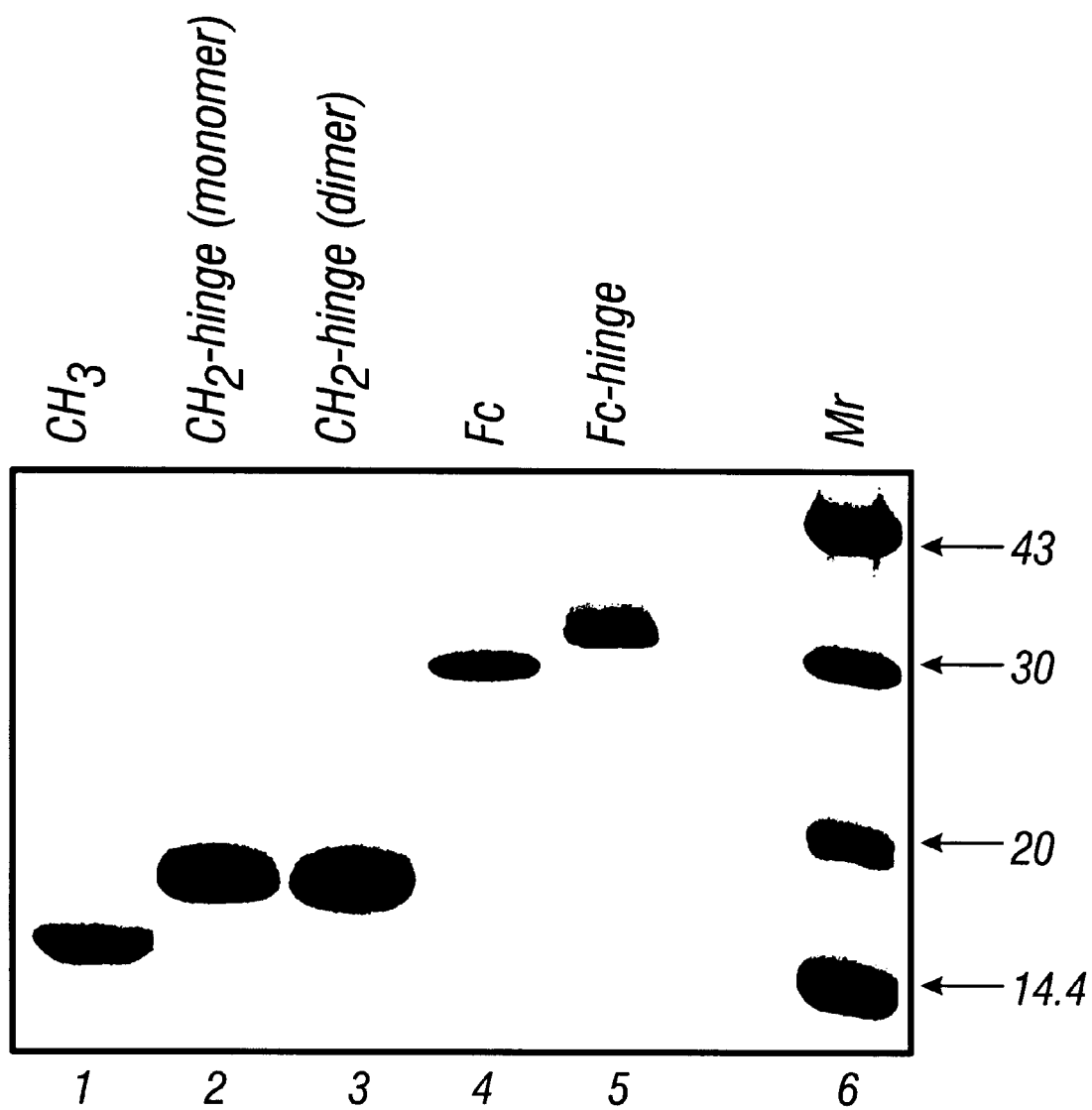
Figure 13B:
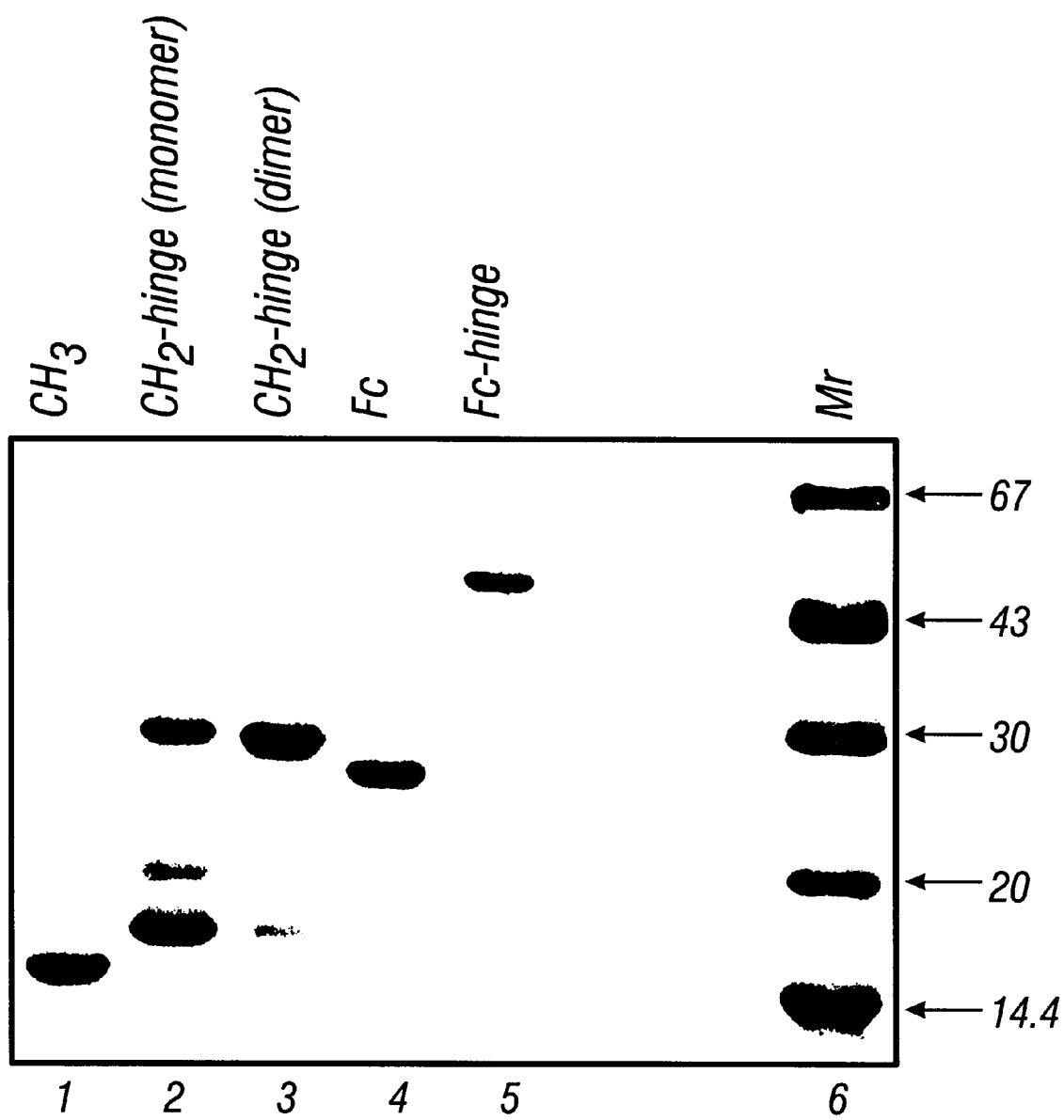

FIGS. 13A and 13B (scanned images). SDS polyacrylamide gel (15%) analyses of purified recombinant proteins, using reducing (FIG. 13A) and non-reducing conditions (panel B). Panel A: lane 1, molecular weight standards; lane 2, CH3 fragment; lane 3, CH2-hinge fragment; lane 4, CH2-hinge fragment following dimerization with Ellman's reagent; lane 5, Fc fragment; lane 6, Fc-hinge fragment, lane 7, molecular weight standards, within the sizes shown in kilodaltons on the right margin. FIG. 13B: as in FIG. 13A, but run under non-reducing conditions.

Figure 14A:
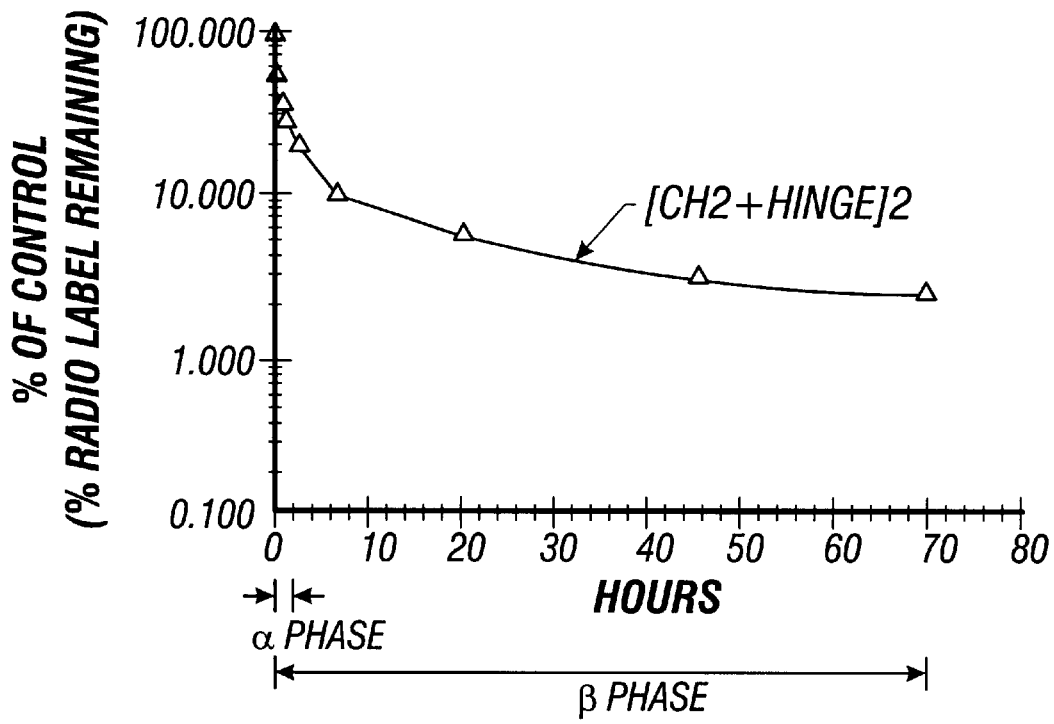
Figure 14B:
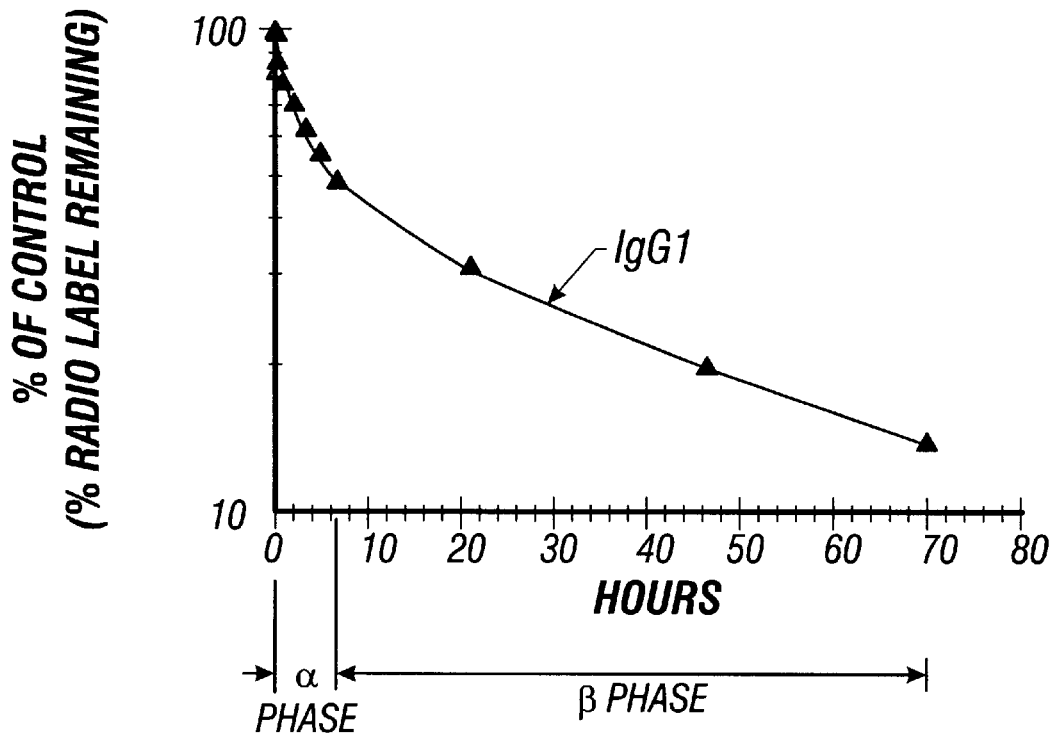

FIGS. 14A and 14B. Clearance curves for, A) recombinant [CH2-hinge]$_2$ and, B) glycosylated IgG1 molecule. The curves are biphasic with a rapid α phase (representing equilibration of the injected protein between the intra- and extra vascular space; the α phase of the proteins are in part determined by the size) and a longer β phase (representing the catabolism of the protein in the intra-vascular space). The half life of the β phases of the fragments are given in Table I and these represent the biological half-lives of the proteins.

FIGS. 15A and 15B-1 and 15B-2 (scanned images). Expression of Fc-hinge fragments and mutants.

Panel A. Vector used for the expression of Fc-hinge fragments and mutants. The lacz promoter is represented by the open circle; the PelB+pelB leader sequence is represented by the hatched box; the Fc-hinge fragment (with no mutations or mutations at positions shown) is represented by the open box; the his$_6$ peptide tag is represented by the filled in box. The numbers (EU numbering) of the N and C terminal amino acids of the recombinant Fc-hinge fragment are shown. The mutants, based on the EU numbering of Edelman et al. (1969), are as follows: (i) I-253, a single mutant, ile 253 to ala 253; (ii) HQ-310, a double mutant, his 310 to ala 310 and gln 311 to asn 311; (iii) HN-433, a double mutant, his 433 to ala 433 and asn 434 to gln 434. A 'tetra-mutant', HQ-310/HN-433, has also been created which has HQ-310 and HN-433 within the same Fc-hinge fragment, i.e., it contains four individual mutations. These details are also summarized in Table II. Amino acid numbers are as in Kabat et al. (1991).

FIG. 15B-1 and FIG. 15B-2 15% SDS polyacrylamide gel analyses of wild type and mutant Fc-hinge fragments, using non-reducing and reducing conditions. Lane 1, wild type; lane 2, I-253; lane 3, HQ-310; lane 4, HN-433; lane 5, HQ-310/HN-433. Sizes of molecular weight standards are shown in kilodaltons on the right margin.

Figure 16:
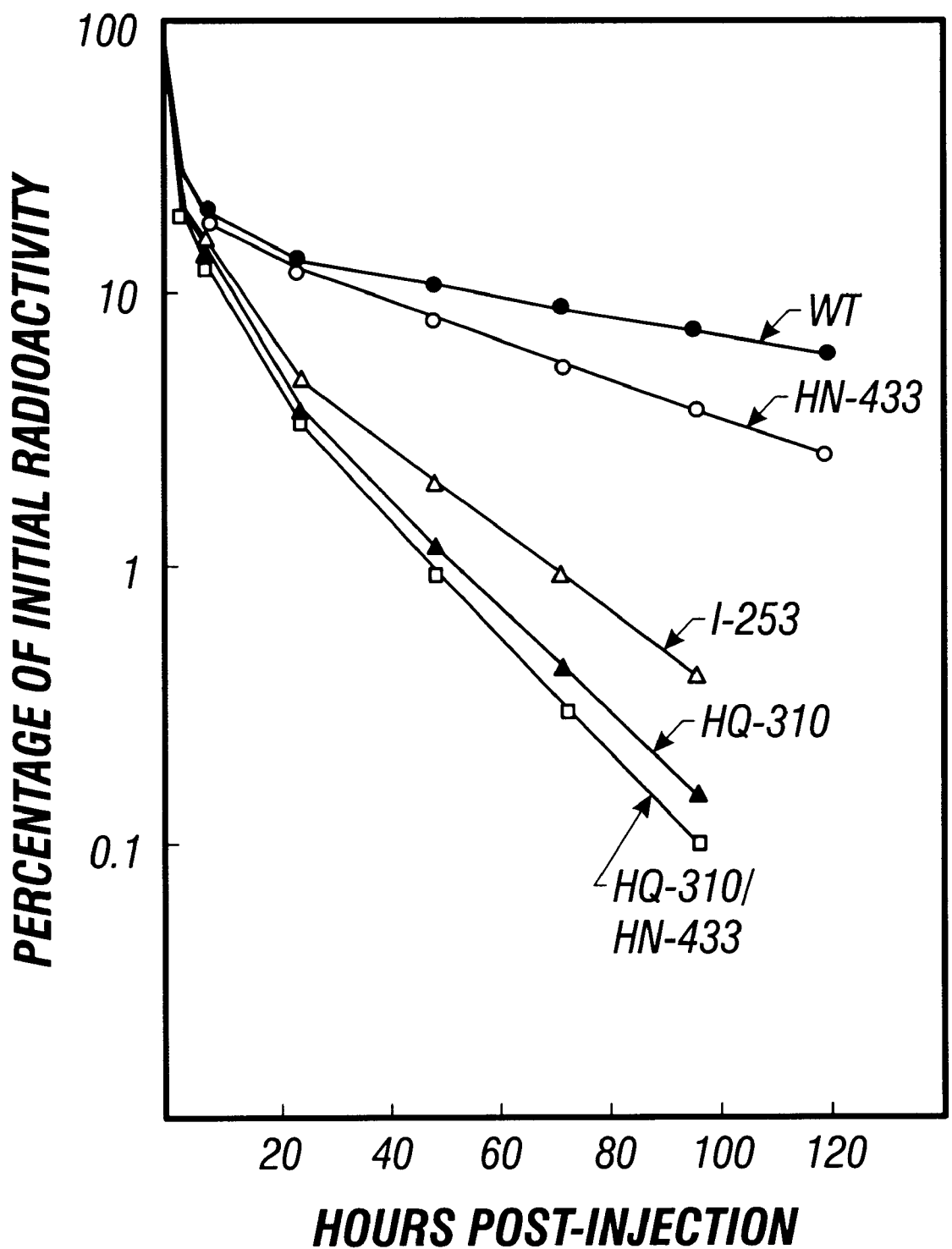

FIG. 16. Clearance curves of wild type Fc-hinge and mutants. The curves are biphasic with an α phase and a β phase. The methods of this study are described in Example 7. The quantitative values for these pharmacokinetic parameters are given in Table III.

Figure 17:
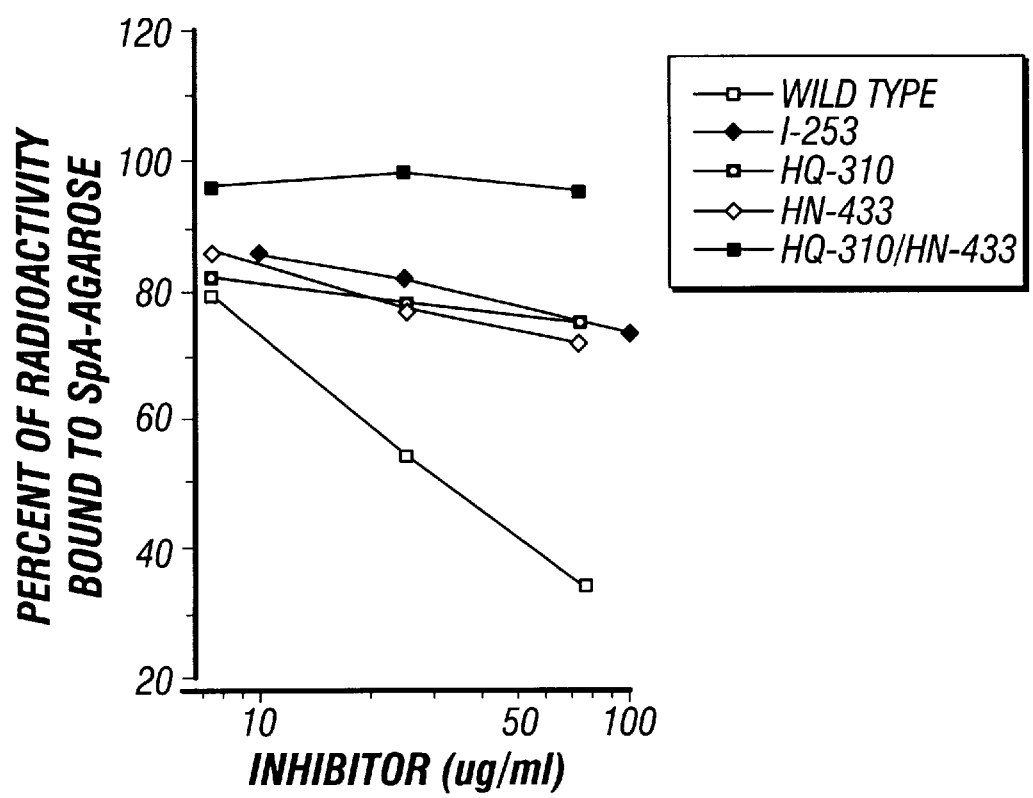

FIG. 17. SpA binding activity of the mutant Fc-hinge fragments relative to wild type. The percentage of inhibition is expressed as the amount of bound labelled wild type Fc-hinge fragment in the presence of unlabelled mutant or wild type Fc-hinge fragment relative to the amount bound in the absence of unlabelled mutant or wild type Fc-hinge fragment.

DETAILED DESCRIPTION OF PREFERRED EMBODIMENTS

A greater understanding of the mechanisms that are involved in regulating antibodies may lead to the development of new immunotherapeutic agents. In particular, knowledge concerning the mechanisms for stabilizing immunoglobulin molecules in vivo and controlling their catabolism would likely allow the generation of novel agents with modified in vivo half lives. This includes both the creation of therapeutic agents that are long-lived in vivo and the generation of molecules with reduced half lives, such as would be useful in the case of an antibody administered for imaging purposes or even a less toxic immunotoxin.

The present invention concerns the cloning and expression of immunoglobulin-like domains and engineered and mutant domains in gram-negative bacterial host cells. Advantages of the production of immunoglobulin-like domains in, for example, *E. coli* compared with mammalian cells include the following: (1) *E. coli* (and other prokaryotic hosts) grow much faster, allowing the results of genetic manipulation of immunoglobulin fragments to be analyzed more quickly; (2) use of *E. coli* is considerably cheaper than mammalian hosts; (3) production of individual immunoglobulin-like domains in mammalian hosts has not been reported. In regard to the generation of anti-idiotypic antibodies, particularly against TCR variable domains, this latter point is particularly significant; (4) the small size of single variable domains (V$_\alpha$, V$_\beta$, V$_\gamma$ and V$_\delta$) renders these fragments amenable to structural analyses using NMR.

Disclosed herein are recombinant vectors encoding immunoglobulin-like domains and portions thereof, such as T-cell receptor variable domains, antibody Fc fragments and subfragments and Fc-hinge domains with reduced in vivo half lives. Methods of producing large quantities of, for example, T-cell receptor domains with native β-pleated sheet structures, and immunoglobulin Fc and Fc-hinge domains, which have the same in vivo stability as intact antibodies, are described, as are methods for producing antibodies and other molecules with reduced half lives. These DNA constructs and protein domains are envisioned to be of various uses, such as in the production of immunotherapeutics or other stable recombinant proteins, or in the production of constructs, such as, e.g., imaging antibodies, with reduced half lives.

As the invention is exemplified by the production of a variety of immunoglobulin-like domains, including variable T-cell receptor V$_\alpha$ and V$_\beta$ domains; antibody Fc-hinge, Fc, CH2-hinge and CH3 domains; and engineered Fc-hinge domains with reduced in vivo half lives, such as, for example, the mutants termed I-253, HQ-10, HN-433 and HQ-310/HN-433; it will be understood that other immunoglobulin-like domains may be expressed employing the methods of the present invention.

It is recognized that a considerable number of the key molecules of the immune system include homologous domains, the structure of which have been conserved throughout evolution. Such molecules are members of the immunoglobulin superfamily, which includes, not only antibodies and T cell receptors, but also MHC class I and II glycoproteins, the CD2, CD4 and CD8 cell—cell adhesion proteins, some of the polypeptide chains of the CD3 complex associated with T cell receptors, and various Fc receptors, all of which contain one or more immunoglobulin-like domains.

Each of these domains is typically about 100 amino acids in length and is thought to be folded into the characteristic sandwich-like structure made of two antiparallel β sheets, usually stabilized by a conserved disulfide bond. Many of these molecules are dimers or higher oligomers in which immunoglobulin homology units of one chain interact with those in another.

Each immunoglobulin homology unit is usually encoded by a separate exon, and its seems likely that the entire supergene family evolved from a gene coding a single immunoglobulin homology unit similar to that encoding Thy-1 or $β_2$-microglobulin, which may have been involved in mediating early cell—cell interactions. Since a Thy-1-like molecule has been isolated from the brain of squids, it is probable that such a primordial gene arose before vertebrates diverged from their invertebrate ancestors some 400 million years ago. New family members presumably arose by exon and gene duplications, and similar duplication events probably gave rise to the multiple gene segments that encode antibodies and T cell receptors.

Apart from antibodies and the T cell receptor, among the best characterized proteins which contain immunoglobulin-like domains are the MHC molecules and the CD4 and CD8 glycoproteins. There are two main classes of MHC (major histocompatibility complex) molecules, class I and II, each consisting of a set of cell-surface glycoproteins. Both classes of MHC glycoproteins are heterodimers with homologous overall structures, the amino-terminal domains of which are thought to be specialized for binding antigen for presentation to T cells.

Each class I MHC gene encodes a single transmembrane polypeptide chain, termed α, most of which is folded into three extracellular, globular domains. Each α chain is non-covalently associated with a nonglycosylated small protein, termed $β_2$-microglobulin. $β_2$-microglobulin and the $α_3$ domain, which are closest to the membrane, are both homologous to an immunoglobulin domain, and thus both proteins are members of the immunoglobulin superfamily. The two amino-terminal domains of the α chain, which are farthest from the membrane, contain the polymorphic (variable) residues that are recognized by T cells in transplantation reactions. T cells also recognize virally derived peptides bound to Class I molecules, and this is particularly important in cellular immunity.

In common with class I MHC molecules, class II MHC molecules are heterodimers with two conserved immunoglobulin like domains close to the membrane and two polymorphic (variable) amino-terminal domains farthest from the membrane. In these molecules, however, both chains span the membrane. There is strong evidence that the polymorphic regions of both classes of MHC molecules interact with foreign antigen and that it is the complex of MHC molecule and foreign antigen that is recognized by the T cell receptor.

CD4 and CD8 are expressed on the surface of helper and cytotoxic T cells, respectively. Both glycoproteins are thought to bind to invariant parts of MHC molecules, CD4 to class II and CD8 to class I MHC glycoproteins.

Other molecules have subsequently been shown to include immunoglobulin-like domains. These include, for example, the PDGF receptor, the extracellular domain of which is thought to be folded into five immunoglobulin-like domains. An increasing number of cell-surface glycoproteins that mediate cell—cell adhesion in vertebrates have also been identified as belonging to the immunoglobulin superfamily. These include N-CAM, a large, single-pass transmembrane glycoprotein which is expressed on the surface of nerve cells and glial cells and mediates $Ca^{2+}$-independent cell adhesion. The extracellular portion of the N-CAM polypeptide is also folded into five immunoglobulin-like domains. The L1 glycoprotein, also known as the neuron-glia cell-adhesion molecule, or Ng-CAM, is also a member of the immunoglobulin superfamily.

Although the immunoglobulin superfamily contains many members, the present study specifically focused on the production of T cell receptor domains and native and engineered antibody domains. Turning firstly to T cell receptor domains, the variable domains of a murine T-cell receptor (TCR) were expressed in a bacterial host cell, allowing the subsequent purification of large quantities of protein. The genes encoding the TCR $V_α$ and $V_β$ domains of T-cell hybridoma 1934.4 (Wraith et al., 1989) were isolated using the polymerase chain reaction (Saiki et al., 1988) and ligated into expression vectors constructed from pUC119 (Viera et al., 1987). pUC119 contains a lacZ promoter sequence upstream of the site into which the $V_α$ and $V_β$ domain genes were ligated. The new expression vectors included a pelB leader segment in translational frame with the cloned variable domain genes.

Modification of these expression vectors, containing $V_α$ and $V_β$ single variable domains, was accomplished by cloning a $V_β$ encoding segment 3' to a $V_α$ gene segment and incorporating a single chain linker peptide. Bacterial hosts transformed with this construct were capable of expressing single chain heterodimeric TCR $V_αV_β$ domains.

The TCR genes employed were derived from a pathogenic CD4+ T-cell clone associated with induction of experimental allergic (autoimmune) encephalomyelitis (EAE) in the H-2ᵘ mouse (Wraith et al., 1989). EAE is a prototypic model of T-cell mediated autoimmune disease and may be a valuable model for multiple sclerosis in humans.

A: T Cell Receptor Variable Domains

Expression of single $V_α$ and $V_β$ domains

Vα and $V_β$genes derived from 1934.4 cells were cloned into VHNco-poly-tag1 to generate $V_α$pelBtag1 ($V_α$ gene only) and $V_β$pelBtag1 ($V_β$ gene only) and transformed into E. coli host cells. The nucleotide sequences of the constructions were confirmed by DNA sequencing prior to growing up and inducing E. coli recombinants for expression. Culture supernatants were analyzed by western blotting which clearly showed that the $V_α$ and Vβ domains were expressed individually and could be secreted into the culture supernatant. The molecular weights, from SDS gel analysis, were estimated as 17 kDa ($V_α$-tag1) and 14.5 kDa ($V_β$-tag1). For the $V_α$ domain this is significantly higher than that predicted by amino acid analysis, but is similar to the anomalously low gel mobilities observed for single antibody VH domains.

The level of secretion of the $V_\alpha$ domain was particularly high and was similar to, if not greater than, that reported for immunoglobulin FvD1.3 fragment expressed and secreted from *E. coli* (Ward et al., 1989). The level was estimated at 10 mg per liter of culture, by comparison with culture supernatants of *E. coli* recombinants harboring pSW1-VHD1.3-VkD1.3-tag1 using western blotting. The relatively high expression level of the $V_\alpha$ domain may reflect a propensity of this domain to form homodimers. Such homodimer formation could mask the hydrophobic residues of the $V_\alpha$ domain which, in a native TCR, interact with analogous $V\beta$ residues during $V_\alpha$:$V_\beta$ pairing, thus increasing the solubility (and secretion levels) of the homodimer.

In contrast to the $V_\alpha$ domain, the $V_\beta$ domain was secreted into the culture supernatant at levels of about 0.5–1 mg per liter of culture, although the intracellular/periplasmic levels of the $V_\beta$ domain were similar to those of the $V_\alpha$ domain. The $V_\beta$ protein apparently does not fold into a soluble form as readily as the $V_\alpha$ domain. It is expected that the amount of secreted $V_\beta$ will be increased by altering the induction conditions. Alternatively, higher levels of soluble $V\beta$ domain may be obtained by osmotically shocking the recombinant *E. coli* cells, followed by denaturation and refolding of the released $V_\beta$ protein.

Co-expression of $V_\alpha$ and $V_\beta$ domains

As illustrated in Example 2, the $V_\alpha$ and $V_\beta$ domains may be co-expressed and secreted from *E. coli* recombinants harboring $V_\alpha V_\beta$pelBtag1. The $V_\alpha$ polypeptide was secreted in excess over the $V_\beta$ domain, indicating that at least some of the recombinant TCR protein is not heterodimeric. However, $V_\alpha$ domain secretion levels were lower when co-expressed with the $V_\beta$ polypeptide than when expressed and secreted as a single domain. This may be due, for example, to limitations on the amount of protein which can be secreted into the *E. coli* periplasm, i.e., $V_\beta$ secretion may compete with $V_\alpha$ secretion. Alternatively, there may be some polarity effects on the expression of the $V_\alpha$ domain, which is 3' to the $V_\beta$ gene in $V_\alpha V\beta$pelBtag1.

One element of the present invention thus demonstrates that TCR $V_\alpha$ and $V_\beta$ polypeptides can be expressed and secreted from recombinant *E. coli* cells as either individual domains or co-expressed. The secretion system may be employed as a rapid and economically favorable alternative to existing methods for the production of TCRs or TCR-immunoglobulin chimeras in mammalian cell transfectomas.

Purification

For purification, the $V_\alpha$ and $V_\beta$ domains were expressed with carboxy terminal (his)$_6$ tags. As a preferred method of purification, induction conditions were established allowing isolation of the protein from the periplasmic space using osmotic shock. The osmotic shock fractions were dialyzed against phosphate buffered saline overnight at 4° C. with 3 changes, and the dialysate passed through an Ni$^{2+}$-NTA-agarose column. Alternatively, longer induction times were used and the protein purified from the culture supernatant. Concentration of the supernatant was then effected by concentration under high pressure using an Amicon filtration unit followed by overnight dialysis against PBS and passage through a Ni$^{2+}$-NTA-agarose column. Using purification from osmotic shock fractions, yields of 1–2 mg/L $V_\alpha$ domain and 0.1–0.2 mg/L $V_\beta$ were obtained.

The $V_\alpha$ and $V_\beta$ domains do not associate when co-expressed within the same bacterial cell. To drive the association of the two domains, therefore, the $V_\alpha$ domain was linked to the $V_\beta$ domain by a synthetic linker and the two domains expressed as a heterodimeric scTCR fragment. This heterodimer may be expressed with carboxy-terminal (his)$_6$ peptide tags and purified using affinity purification on Ni$^{2+}$-NTA-agarose columns. The purification yields from osmotic shock fractions were 0.5–1 mg/L culture.

Structural Analyses To assess the folded state of the recombinant TCR fragments, CD spectral analyses were carried out on the fragments and on the D1.3 single chain Fv fragment. The minima in the curves at 218 nm for these proteins indicate the presence of a high proportion of β-pleated sheet structure (Johnson, 1990). These spectra also indicated a lack of α-helical regions, since α-helical regions result in minima at ~208 nm and 224 nm, and this is consistent with the proposed structural models for TCR extracellular domains (Novotny et al., 1986; Chothia et al., 1988), and the structure of the crystallographically solved D1.3 Fv fragment (Bhat et al., 1990). The maxima at approximately 205 nm in the spectra of the $V_\alpha$ domain and the D1.3Fv fragment has previously been associated with the presence of an abundance of β-turns.

Overall and in general terms the invention shows that single $V_\alpha$, $V_\beta$ domains and single chain heterodimeric TCRs (scTCRs) derived from an encephalitogenic T cell hybridoma may be expressed and purified in yields ranging from 0.1–2 milligrams per liter of bacterial culture. In addition, structural analysis using CD indicates that the recombinant TCR fragments contain a high proportion of β pleated sheet structures. Although molecular modelling has indicated that the extracellular domains of TCRs may resemble immunoglobulin Fv and Fab fragments in structure (Novotny et al., 1986; Chothia et al., 1988), to date this has not been demonstrated empirically.

The ability of the $V_\alpha$, $V_\beta$ domains and heterodimeric scTCR to inhibit the binding of the 1934.4 T cell hybridoma to cognate peptide-MHC complexes (N-terminal residues 1–11 of myelin basic protein associated with the MHC class II protein I-A"; Wraith et al., 1989) is of particular interest because it would demonstrate functional activity of the recombinant proteins. It is conceivable, however, that soluble TCR fragments are ineffective inhibitors of the multivalent, high avidity, interaction (Harding and Unanue, 1990) of T cell borne antigen receptors with peptide-MHC complexes. The tripartite interaction of 'native' TCR on CD4+ T cells with peptide-MHC complexes may be stabilized by contacts between CD4 residues and the MHC class II molecule (Sleckman et al., 1987: Fleury et al., 1991). The absence of this 'co-receptor' in the recombinant TCRs may therefore decrease the avidity of the interaction further.

B: Antibody Constant Domains

The features of an immunoglobulin molecule that determine high stability in vivo were poorly understood prior to the present invention. Previous studies indicate that the CH2 domain may play an important role in the control of catabolism of antibodies, and a recent study has also suggested that sequences in the CH3 domain may be involved (Ellerson et al., 1976; Mueller et al., 1990; Pollock et al., 1990). The presence of carbohydrate residues on the CH2 domain appears to have a minor if significant effect on the stability, and the extent of the effect is dependent on the isotype (Tao & Morrison, 1989).

As part of the present work, recombinant CH2-hinge, CH3, Fc and Fc-hinge fragments derived from the murine IgG1 constant region have been expressed and secreted from recombinant *E. coli* cells. The fragments have been purified, radiolabeled and used in clearance studies in mice. The clearance rates have been compared with those of an Fv fragment and a complete glycosylated IgG1 molecule. The recombinant Fc-hinge fragments have stability properties that are very similar to those of the complete immunoglobulin molecule. In contrast, the CH2-hinge and CH3 fragments are both cleared rapidly and in a similar way to the Fv fragment. This indicates that sequences in both the CH2 and CH3 region are important for in vivo stability, and in addition, that glycosylation only plays a minor role in the control of the catabolism of this isotype.

To accomplish prokaryotic expression, fragments of the genes encoding domains derived from the murine IgG1 immunoglobulin molecule 9E10 were ligated into expression plasmids, in a similar manner to that described for the T cell receptor variable domain fragments, and the ligated DNA was transformed into E. coli. This resulted in the expression and secretion of antibody constant domain fragments by the recombinant host cells. The recombinant proteins were isolated from the periplasm by osmotic shock followed by affinity purification using $Ni^{2+}$-NTA-agarose, and were purified in yields of 2, 1–1.5, 1.5–2 and 0.5–1 milligrams per litre of culture for the CH3 domain, CH2-hinge fragment, Fc fragment and Fc-hinge fragment respectively.

The CH3 domain, Fc fragment and Fc-hinge fragment were all found to be homodimeric proteins. For the Fc and CH3 domain, the dimers are non-covalently linked, and are presumably stabilized by non-covalent interactions. For the Fc-hinge dimer, the fragments are covalently linked by —S—S— bridges between the hinge region cysteines. Approximately 90% of the CH2-hinge fragment was found to be expressed and purified in a monomeric form.

A particularly important aspect of this study is the finding that the immunoglobulin Fc-hinge and Fc fragments, purified following expression in E. coli, have the same in vivo stability as a native antibody molecule. This was determined by measuring the clearance rates of $^{125}$I-radiolabeled immunoglobulin fragments in vivo as a function of time. Results from these studies demonstrated that the recombinant aglycosylated Fc-hinge or Fc fragments have similar stability in vivo as the complete glycosylated IgG1 molecule.

The recombinant aglycosylated Fc fragment, with or without a hinge region, was found to have a β phase similar to that of a complete glycosylated IgG1 immunoglobulin molecule. These results indicate that for the murine IgG1 isotype the presence of carbohydrate residues does not appear to be necessary for in vivo stability, although it may still play a minor role. In contrast to the clearance data for the Fc and Fc-hinge fragments, both dimeric CH2-hinge and CH3 fragments are catabolized as rapidly as antibody Fv fragments. This indicates that for the murine IgG1 isotype, the presence of sequences in both the CH2 and CH3 domains are necessary for in vivo stability. Previous data obtained using protein chemistry suggested that the CH2 domain is responsible for in vivo stability (Ellerson et al., 1976) although a recent study indicated that residues in the CH3 domain may also be involved in the catabolism control of the murine IgG2a and IgG2b isotypes (Pollock et al., 1990).

The present discoveries relating to stability are particularly important as the in vivo stability of aglycosylated Fc fragments has not been previously assessed (Nose et al., 1990). Aglycosylated Fc fragments, in comparison with the glycosylated version (prepared by proteolysis of immunoglobulin produced by mammalian cells), are known to have reduced binding to complement C1q and greatly reduced binding to Fc receptors on monocytes (Nose et al., 1990; Leatherbarrow et al., 1985; Nose & Wigzell, 1983). However, these advantageous properties would be of little significance if the aglycosylated molecules were found to be unstable. The inventors have been able, for the first time, to express aglycosylated Fc fragments which proved to be stable in vivo.

The production of the IgG1 Fc-hinge or Fc fragment in E. coli has allowed the important residues of this region involved in controlling antibody stability and catabolism in vivo to be elucidated. These results are described in Example 7. Furthermore, following the present invention, human Fc domains may now be produced in E. coli, allowing further detailed studies of the human protein. Additionally, the bacterial secretion of Fc or Fc-hinge domains, or Fc or Fc-hinge domain:fusion proteins, whether of murine or human origin, is envisioned to provide a convenient, economically attractive and rapid route for the production of novel stabilized proteins.

Following structural analyses, smaller regions of the Fc structure may be employed in protein chimeras, or fusion proteins, to produce biologically stable therapeutic agents. This is particularly useful for the production of therapeutic agents which cannot be obtained from other expression systems, such as mammalian cells, due to proteolysis. As such, the Fc-hinge or Fc domains of the present invention, or portions thereof, are proposed to be useful modules for both the tagging and stabilization of recombinant molecules, including chimeric proteins of therapeutic use.

C: Engineered Antibody Domains with Reduced In Vivo Half Lives

The mechanisms involved in regulating the in vivo catabolism of IgG molecules are currently not well understood, although the Fc region is believed to contain sequences that are important for serum persistence of IgG (Spiegelberg & Weigle, 1965). As described herein and by Pollock et al. (1990), the CH2 domain and, to a lesser extent, the CH3 domain, have been shown to influence biological half life of IgGs.

It has been observed that Staphylococcal protein A (SpA)-IgG complexes are cleared more rapidly from serum than uncomplexed IgG molecules (Dima et al., 1983). Results from X-ray crystallography studies have indicated that residues in the Fc-hinge region are involved in SpA binding (Deisenhofer, 1981). These distinct lines of information prompted the present inventors to mutate residues at the CH2–CH3 domain interface of the (above-described) recombinant Fc-hinge fragment derived from the murine IgG1 molecule and to investigate the catabolism of the resultant mutants.

Using this approach, several amino acid residues of the CH2 domain (Ile-235 and His-310-Gln-311) and of the CH3 domain (His-433-Ala-434) were changed by in vitro mutagenesis. The mutant proteins were then purified from recombinant E. coli cells and the pharmacokinetic parameters measured in mice. The results from such studies demonstrate that amino acid residues from the CH2 domain, and to a lesser extent those from the CH3 domain, are directly involved in the catabolism of mouse IgG1. Thus, the site of the IgG1 molecule that controls catabolism is located at the CH2–CH3 domain interface and is distinct from the lower hinge region that is involved in binding to Fc receptors (Duncan et al., 1988; Lund et al., 1991). The identification of specific amino acid residues that are involved in catabolism control supports the hypothesis that receptor bearing cells may be important in regulating serum IgG levels (Brambell et al., 1964).

The inventors have termed the specific residues of the murine IgG1 molecule that they discovered to be involved in controlling the catabolism of this isotype the 'catabolic control site'. This region is distinct from the sites of interaction with Fc receptors but overlaps with the SpA binding site. This is, therefore, consistent with earlier data that showed that SpA-immunoglobulin complexes were cleared more rapidly than uncomplexed immunoglobulins (Dima et al., 1983). This data does not rule out the involvement of additional residues of the Fc fragment in catabolism control, but it does provide a clear means by which the biological half life of an antibody or antibody-based molecule or conjugate may be shortened. It also provides a means by which the longevity of a particular antibody may be increased if desired, by re-inserting residues such as ile 253, his 310, gin 311, his 433 and asn 434, should any such residues be found to be mutated in a particular antibody.

Although the mechanisms involved in the catabolism of IgG molecules have still to be completely elucidated, the data presented herein support the concept that SpA-like 'protective' receptors bind to the CH2–CH3 domain interface on IgGs and protect them from degradation. The engineered Fc-hinge fragments which form these aspects of the present invention are envisioned to be useful reagents in a variety of embodiments. For example, they may be employed in the isolation the putative receptor and in further delineating the sites and mechanism of IgG catabolism.

An improved understanding of IgG breakdown mechanisms, as represented by the discoveries of the present invention, would also likely be of use in the design of therapeutic molecules with specified pharmacokinetic properties. The inventors contemplate that antibody molecules with reduced half lives may now be designed and constructed. These may be used, for example, in antibody-based imaging regimens, in antibody binding and removal of pathogens, toxins or drugs, and in second or third generation immunotoxins with reduced binding to normal tissues and hence reduced side effects.

D: Imaging Agents and Immunotoxins

The present invention provides methods for creating recombinant molecules, such as antibody constructs, with decreased in vivo half lives. This is contemplated to be particularly beneficial for use with imaging antibodies, and even with immunotoxins. As such, recombinant molecules may be designed which are more quickly removed from circulation after exerting their desired action. Currently, imaging technology does not employ whole antibodies which do not result in precise enough images. Rather, bispecific Fab fragments are used which are often difficult to synthesize. Methods for the engineering of antibodies which are cleared from the body more rapidly, as disclosed herein, therefore represent a significant advance in this area.

In general, to generate an antibody or antibody construct with a reduced half-life, one would preferably incorporate one or more of the catabolism controlling mutations described herein into the antibody portion of the molecule, with mutations at ile 253, his 310 and gln 311, being preferred, and multiple mutants being even more preferred. Alternatively, one could also fuse one of the mutant Fc-hinge domains disclosed herein to any desired variable domain or domains. Imaging and immunotoxin technologies are generally known to those of skill in the art and may be advantageously combined with the teachings of the present invention.

Antibodies

Antibodies or antibody fragments (e.g., Fab', Fab or F(ab')$_2$) are currently used in human diagnosis therapy. Monoclonal antibodies are often employed, which may be of human, murine, monkey, rat, hamster, chicken or even rabbit origin. "Humanized" antibodies are also used as are chimeric antibodies from mouse, rat, or other species, bearing human constant and/or variable region domains, single domain antibodies (e.g., DABs), Fv domains, bispecific antibodies, as well as recombinant antibodies and fragments thereof. Due to the ease of preparation and ready availability of reagents, murine monoclonal antibodies are contemplated to be preferable as starting material to engineer a reduced half life antibody in accordance with the present invention.

There is a very broad array of antibodies known in the art that have immunological specificity for tumors, as a vast number of tumor associated antigens have been identified. Methods for the development of antibodies that are "custom-tailored" to the patient's tumor are likewise known. Any antibody of sufficient selectivity, specificity and affinity may be employed as the basis for an antibody conjugate. Such properties may be evaluated using conventional immunological screening methodology known to those of skill in the art.

Imaging Antibody Constructs

Antibody-based molecules are often used as diagnostic agents in which antibody-imaging constructs are created which have the ability to provide an image of, for example, tumors and tumor vasculature, through magnetic resonance imaging, X-ray imaging, computerized emission tomography and such technologies. In antibody-imaging constructs, the antibody portion used is generally directed against the tumor or a specific marker thereof, or against tumor vasculature, and the imaging agent is an agent detectable upon imaging, such as a paramagnetic, radioactive or fluorogenic agent. Many such imaging agents are known in the art, as are methods for their attachment to antibodies (see, e.g., U.S. Pat. Nos. 5,021,236 and 4,472,509, both incorporated herein by reference).

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, one might mention iodine$^{131}$, iodine$^{123}$, technicium$^{99m}$, indium$^{111}$, rhenium$^{188}$, rhenium$^{186}$, galium$^{67}$, copper$^{67}$, yttrium$^{90}$, iodine$^{125}$, or astatine$^{211}$.

Immunotoxins

Immunotoxin technology is fairly well-advanced and known to those of skill in the art of antibody research. Immunotoxins are agents which have an antibody component linked to another agent, particularly a cytotoxic or otherwise anticellular agent, having the ability to kill or suppress the growth or cell division of cells. Exemplary anticellular agents include chemotherapeutic agents, radioisotopes as well as cytotoxins. Example of chemotherapeutic agents are hormones such as steroids; antimetabolites such as cytosine arabinoside, fluorouracil, methotrexate or aminopterin; anthracycline; mitomycin C; vinca alkaloids; demecolcine; etoposide; mithramycin; or antitumor alkylating agents such as chlorambucil or melphalan.

Preferred immunotoxins often include a plant-, fungal- or bacterial-derived toxin, such as an A chain toxin, a ribosome inactivating protein, α-sarcin, aspergillin, restirictocin, a ribonuclease, diphtheria toxin or *pseudomonas* exotoxin, to mention just a few examples. The use of toxin-antibody constructs is well known in the art of immunotoxins, as is their attachment to antibodies. Of these, a particularly preferred toxin for attachment to antibodies will be a deglycosylated ricin A chain. Deglycosylated ricin A chain (dgA) is preferred because of its extreme potency, longer half-life, and because it is economically feasible to manufacture it a clinical grade and scale (available commercially from Inland Laboratories, Austin, Tex.) Truncated ricin A chain, from which the 30 N-terminal amino acids have been removed by Nagarase (Sigma), may also be employed.

The preparation of immunotoxins is generally well known in the art (see, e.g., U.S. Pat. No. 4,340,535, incorporated herein by reference). Numerous types of disulfide-bond containing linkers are known which can successfully be employed to conjugate toxin moieties to antibodies, however, certain linkers are generally preferred, such as, for example, sterically hindered disulphide bond linkers are preferred due to their greater stability in vivo, thus preventing release of the toxin moiety prior to binding at the site of action. A particularly preferred cross-linking reagent is SMPT, although other linkers such as SATA, SPDP and 2-iminothiolane may also be employed. Blue-Sepharose, a column matrix composed of Cibacron Blue 3GA and agarose, may be used to purify immunoconjugates, which may then be formulated into a suitable pharmaceutical composition, such as described in Remington's Pharmaceutical Sciences, 16th Ed. Mack Publishing Company, 1980, incorporated herein by reference.

The following examples are intended to illustrate the practice of the present invention and are not intended to be limiting. As the invention is demonstrated with a variety of immunoglobulin-like domains, including variable murine T-cell $V_\alpha$ and $V_\beta$ domains; antibody Fc-hinge, Fc, CH2-hinge and CH3 domains; and mutant domains with reduced stability; it will be understood that other domains will be adaptable to similar constructs as those described hereinabove. Likewise, a variety of tags, linker sequences and leader sequences may be employed depending on the particular purification or isolation methods desired to obtain the polypeptide products.

EXAMPLE 1

The following example illustrates the construction of plasmids for expression of the T-cell receptor single domains, $V_\alpha$ and $V_\beta$ and the single chain $V_\alpha V_\beta$ construct. Two types of plasmids are illustrated; one with a c-myc tag and the other with a (his)$_6$ tag. Other tags could be used.

Bacterial Strains and Plasmids

*E. coli* BMH71-18 was used as host for the cloning and expression of TCR domains (Rüther et al., 1981). Plasmid pSWI-VH-poly-tag1 (Ward et al., 1989) was modified by replacing pUC19 with pUC119 (Viera et al., 1987) as the backbone vector. In addition, an NcoI restriction site was inserted into the pelB leader sequence using site directed mutagenesis to generate V$_H$Nco-poly-tag1.

Isolation of $V_\alpha$ and $V_\beta$ Genes

The $V_\alpha$ and $V_\beta$ genes were isolated from 1934.4 hybridoma cells (Dr. D. Wraith, Cambridge University, Department of Pathology, Immunology Division, Level 3 Laboratories Block, Addenbrookes's Hospital, Hills Road, Cambridge CB2 2QQ, UK) using a PCR amplification method. 10$^6$ cells were washed once in sterile PBS, then resuspended in 1 ml sterile deionized water and heated at 100° C. for 5 mins. This results in isolation of genomic DNA. Debris was pelleted by centrifugation for 3 minutes at room temperature at 11,000 rpm and 2–10 $\mu$l of supernatant used in a PCR reaction with the following $V_\alpha$ or $V_\beta$ specific primers:

$V_\alpha$:
I(SEQ ID NO18: 5'-ATC CTT <u>CCA TGG</u> CCG ACT CAG TGA CTC AGA CGG AAG GT-3'
II(SEQ ID NO19: 5'-AAG GAT <u>GGT GAC C</u>GG TTT ATT GGT GAG TTT GGT TCC-3'
$V_\beta$:
III(SEQ ID NO20: 5'-ATC CTT <u>CCA TGG</u> CCG AGG CTG CAG TCA CCC AAA GTC CA-3'
IV(SEQ ID NO21: 5'-AAG GAT <u>GGT GAC C</u>AG AAC AGT CAG TCT GGT TCC TGA-3'

For each domain, the oligonucleotides encode either an NcoI or BstEII fragment (underlined) to allow restriction enzyme digestion of the PCR products, followed by gel purification using "Geneclean" (BIO 101, Valley Park, Mo. 63088) and ligation as an NcoI-BstEII fragment into VHNco-poly-tag1.

PCR conditions were as follows:
3 units Promega Taq polymerase (Promega, Madison, Wis. 53711–5399)
5 $\mu$l 10×Promega reaction buffer
25 pmol of each oligonucleotide primer
0.2 mM dNTPs
2–10 $\mu$l 1934.4 hybridoma supernatant (crude genomic DNA preparation)
Water to 50 $\mu$l Cycling conditions were 94° C. for 0.5 min, 55° C. for 0.5 min, 72° C. for 1 min with Taq polymerase added at the end of the first cycle, that is, at 72° C. Thirty cycles of PCR were conducted and an additional 3 units of Taq polymerase added after 15 cycles to minimize occurrence of PCR errors. Alternatively, less error-prone polymerases such as Vent™ polymerase (New England Biolabs, Beverly, Mass. 01915-5599) may be used.

V$_\alpha$pelBtag1 Plasmid

Figure 3:
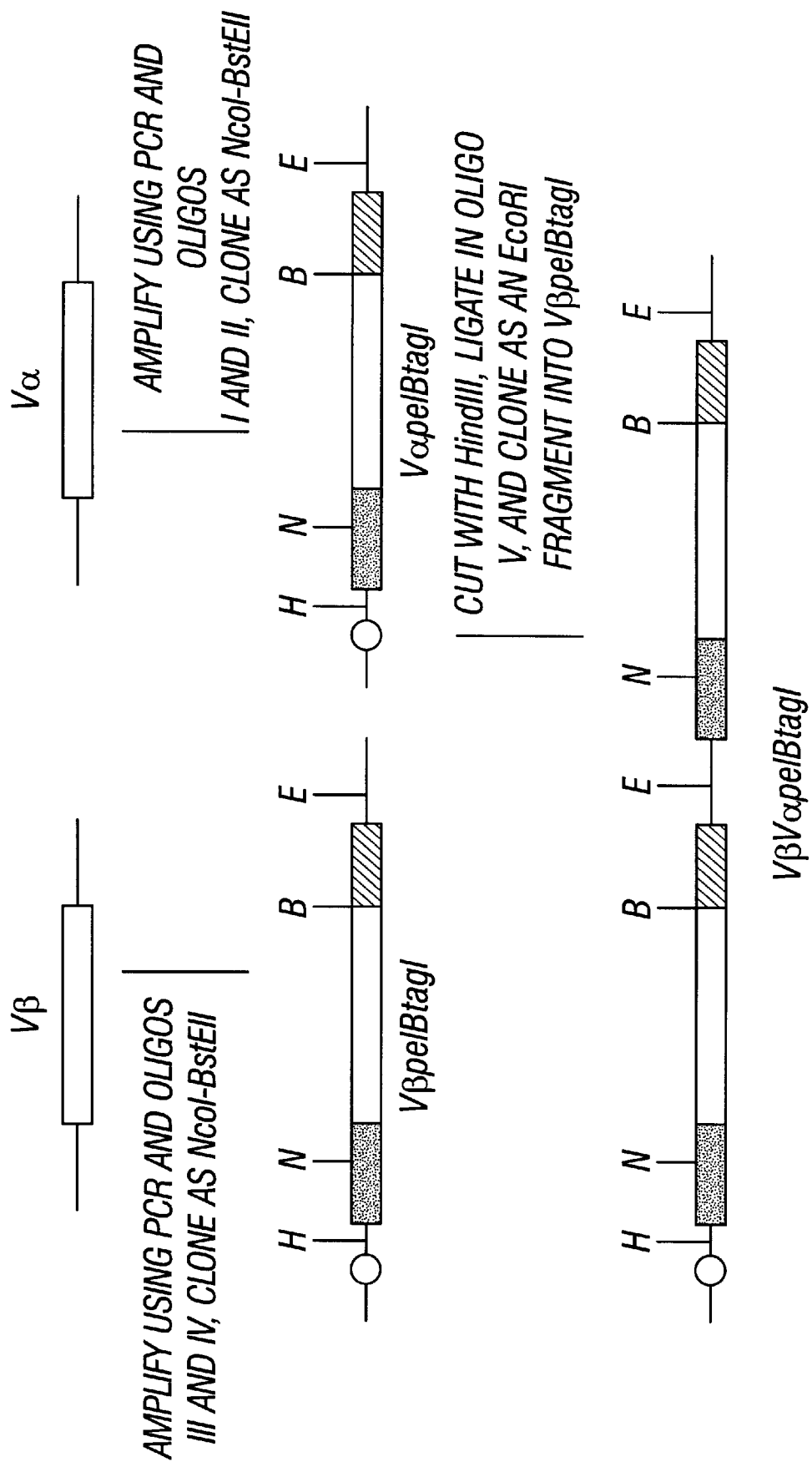
FIG. 3. Construction of plasmids for expression of the $V_\alpha$ domain ($V_\alpha$pelBtag1), $V_\beta$ domain ($V_\beta$pelBtag1) and co-expression of the two domains ($V_\alpha V_\beta$pelBtag1). H=HindIII, N=NcoI, B=BstI and E=EcoRI. Filled in box= pelB leader, stippled box=$V_\beta$ gene, striped box=five 3' codons of VH gene in pSWI-VH-poly-tag1 plus tag1 (c-myc) codons, open box=$V_\alpha$ gene and open circle=lacZ promoter.

The tag portion for the plasmid construct used in this example is c-myc with the following nucleic acid sequence (SEQ ID NO: 22) GAA CAA AAA CTC ATC TCA GAA GA GGA TCT GAAT encoding the following 11-mer (SEQ ID NO23: glu gln lys leu ile ser glu glu asp leu asn. The polylinker sequence is (SEQ ID NO: 24): CTG CAG TCT AGA GTC GAC CTC GAG GGT CACC.

pSWI-VH-poly-tag1 (Ward, et al., 1989) was modified by the insertion of a unique NcoI site into the pelB leader sequence using site-directed dideoxynucleotide mutagenesis (Carter, et al., 1985) and the oligonucleotide 5'-GGC CAT GGC TGG TTG GG-3' (SEQ ID NO: 25) to generate VH Nco-poly-tag1. The pelB leader sequence was ATG AAA TAC CTA TTG CCT ACG GCA GCC GCT GGA TTG TTA TTA CTC GCT GCC CAA CCA <u>GCG ATG GCC</u> (SEQ ID NO:26). The underlined portion was converted to CCATGG by mutagenesis. The $V_\alpha$ gene isolated and tailored by the PCR was then cloned in translational frame as an NcoI-BstEII fragment into VH Nco-poly-tag1 to generate V$_\alpha$pelBtag1 as shown in FIG. 3. Dideoxynucleotide sequencing was carried out to confirm the DNA sequences of the plasmid construction.

V$_\beta$pelBtag1 Plasmid

The V$_\beta$pelBtag1 plasmid was constructed according to the procedure for the V$_\alpha$ plasmid except that the V$_\beta$ gene was used in place of V$_\alpha$. The construct is shown in FIG. 3.

V$_\alpha$V$_\beta$pelBtag1 Plasmid

To construct the V$_\alpha$V$_\beta$pelBtag1 plasmid, V$_\alpha$pelBtag1 was modified by replacement of the 5' HindIII site of pUC119 (Viera and Messing,, 1987) with an EcoRI site by ligation of oligonucleotide V (SEQ ID NO:27). 5'-AGC T<u>GA ATT C</u> 3' as a duplex into HindIII restricted V$_\alpha$pelBtag1 (with the EcoRI site shown underlined). The ligation destroyed the HindIII site. It was then cloned as an EcoRI fragment into EcoRI restricted V$_\beta$pelBtag1, shown in FIG. 3. Recombinants were analyzed for correct orientation of the V$_\alpha$ gene with respect to the V$_\beta$ gene by restriction enzyme analysis. Dideoxynucleotide sequencing was carried out to confirm the DNA sequences of the plasmid construction.

scV$_\alpha$V$_\beta$pelBhis Plasmid

The V$_\alpha$ and V$_\beta$ domains do not associate when they are co-expressed within the same bacterial cell. To drive the association of the two domains, therefore, the V$_\alpha$ domain was linked to the V$_\beta$ domain by a synthetic peptide linker and the two domains expressed as a heterodimeric scTCR fragment. This heterodimer was expressed with carboxy-terminal (his)$_6$ peptide tags and purified as herein described for single chain domains. Purification yields were 0.5–1.0 mg/L culture.

Figure 8:
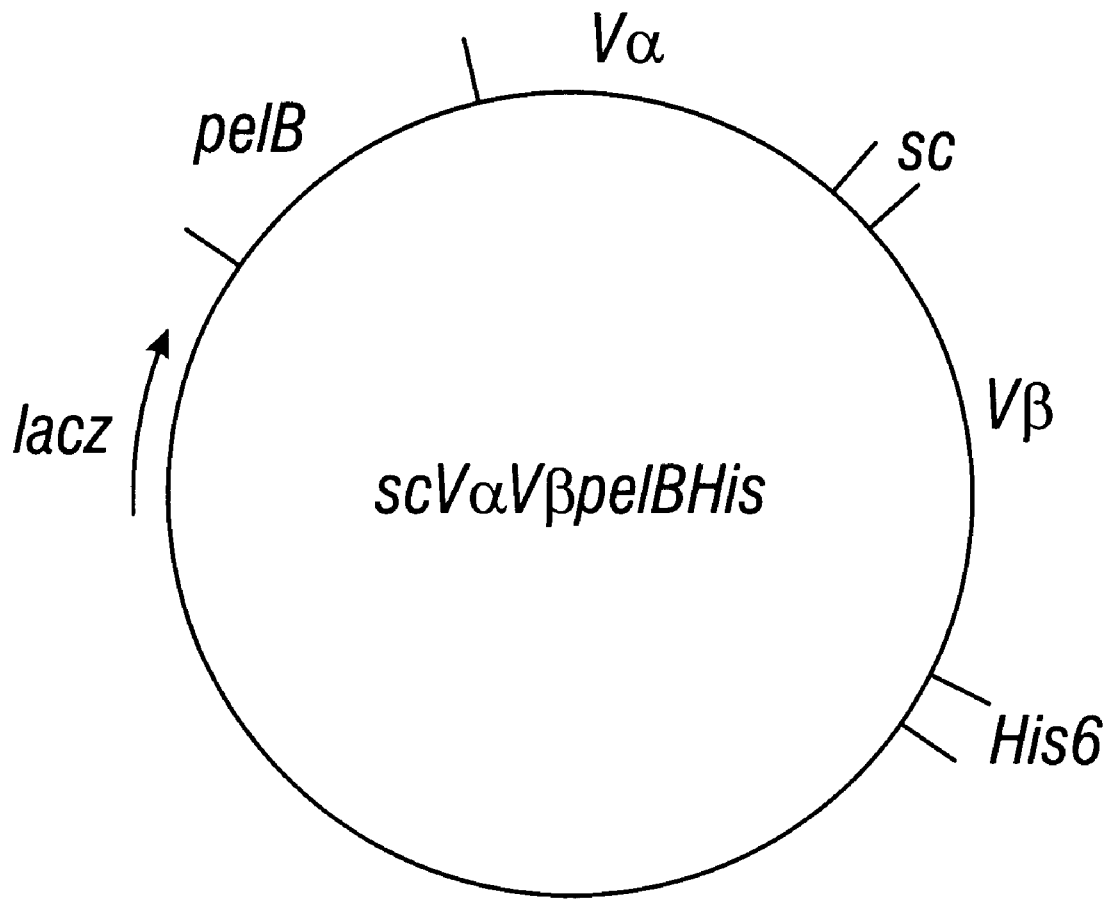
FIG. 8. Schematic representation of the plasmid construct for scTCR.
Figure 15A:
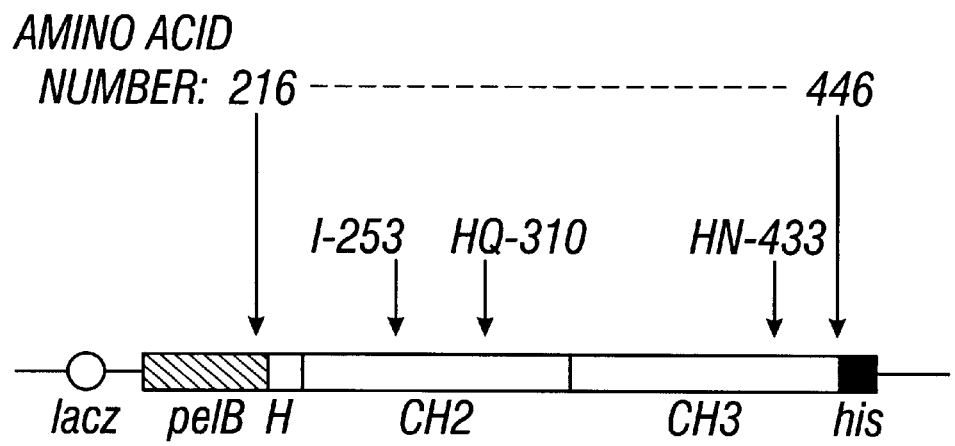
Figures 1, 15B:
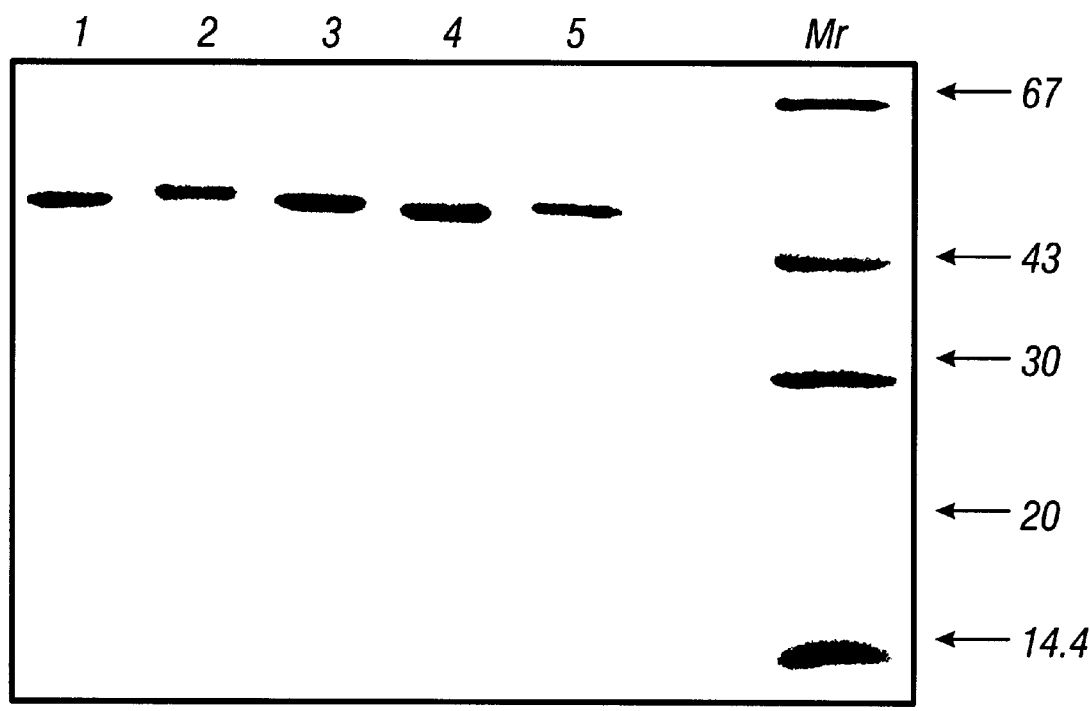

The plasmid V$_\alpha$V$_\beta$pelBmyc2 (FIG. 1) was constructed in a similar manner to V$_\alpha$pelBmyc or V$_\alpha$V$_\beta$pelBtag1, except that the V$_\beta$pelBmyc gene was cloned 3' to the V$_\alpha$pelBmyc gene. The plasmid scV$_\alpha$V$_\beta$pelBhis, shown schematically in FIG. 8, was constructed as indicated in FIG. 1. The V$_\alpha$ gene was ligated 5' to the V$_\beta$ gene so that in the expressed protein the V$_\alpha$ domain was located at the N-terminus of the V$_\alpha$V$_\beta$ heterodimer. Since the V$_\alpha$ domain is more soluble than the V$_\beta$ domain and expressed at higher levels, this orientation of the two domains with respect to each other appears to assist in the secretion and folding of the scTCR.

The single chain linker, (Gly$_4$Ser)$_3$ (Huston et al., 1988) was ligated into BstEIII-PstI restricted V$_\alpha$δV$_\beta$pelB as the following DNA duplex:

5'-GTC ACC GGT GGA GGC GGT TCA GGC GGA GGT GGC TCT GGC GGT GGC
   3'G CCA CCT CCG CCA AGT CCG CCT CCA CCG AGA CCG CCA CCG
GGA TCG GAG GCT GCA- 3'
CCT AGC CTC CG-5'
(5' to 3' sequence=SEQ ID NO:28 and 3' to 5' sequence= SEQ ID NO:29).
where the coding strand is indicated by underlining.

To construct sc V$_\alpha$V$_\beta$pelBmyc, the resulting HindIII-PstI fragment (scV$_\alpha$δV$_\beta$pelB) encoding the pelB leader, the V$_\alpha$ gene, the single chain linker and the 5' end of the V$_\beta$ gene was ligated into HindIII-PstI restricted V$_\beta$pelBmyc to replace the pelB leader. To insert the (his)$_6$ peptide tag into scV$_\alpha$V$_\beta$pelBmyc, the plasmid was restricted with BstEII and the following duplex ligated into the construct (FIG. 1):

5'-GTC ACC CAT CAC CAT CAC CAT CAC TAA TAA- 3'
   3'G GTA GTG GTA GTG GTA GTG ATT ATT CAG TG-5'
(5' to 3' sequence=SEQ ID NO:30 and 3' to 5' sequence= SEQ ID NO:31).
with the coding strand indicated by underlining.

Recombinant clones with the correct orientation of the (his)$_6$ tag were identified by PCR screening. Ligation of the duplex in the correct orientation into BstEII cut scV$_\alpha$V$_\beta$pelBmyc removed the 3' BstEII site. In addition, the presence of 2 stop codons at the 3' end of the histidine codons prevented readthrough into the downstream c-myc tag sequences. Nucleic acid and derived amino acid sequences of the single chain TCR with attached (his)$_6$ tag is shown in FIG. 7 (seq id nos:5 and 6).

Single stranded DNA was purified from extruded phage using polyethylene glycol precipitation. Sequencing reactions were then carried out using aliquots of the single stranded DNA, appropriate oligonucleotide primers and Sequenase (USB Corp, Cleveland, Ohio 44122) as polymerase. Random low level incorporation of dideoxynucleotides corresponding to each nucleotide position in the gene which was being sequenced occurred by using low levels of chain terminators (dideoxynucleotides) in the reaction mixes. The extended, prematurely terminated single stranded DNA molecules were then analyzed by electrophoresis followed by autoradiography with radiolabeled nucleotides included in the reactions to improve the sensitivity of detection.

V$_\alpha$pelBhis and V$_\beta$pelBhis were constructed using the strategy shown in FIG. 1. Prior to expression analysis, all DNA constructs were sequenced using the dideoxynucleotide method. Single stranded DNA was isolated from the clones by growth of the recombinant cells in the presence of helper phage, VCSM13 (Stratagene, La Jolla, Calif. 92037). Nucleic acid (seq id nos:1 and 3) and derived amino acid sequences (seq id nos:2 and 4) for V$_\alpha$pelBhis and V$_\beta$pelBhis are shown in FIGS. 5 and 6 respectively.

V$_\alpha$pelBhis Plasmid

V$_\alpha$pelBhis was constructed using the strategy outlined in FIG. 1. This involved restriction by BstEII to remove the single chain linker sequence and the V$_\beta$ domain gene followed by relegation.

V$_\beta$pelBhis Plasmid

V$_\beta$pelBhis was constructed using the strategy outlined in FIG. 1. A PstI-EcoRI fragment encoding the majority of the V$_\beta$ domain gene and the (his)$_6$ tag was isolated following restriction enzyme digestion. This was then ligated into PstI-EcoRI restricted V$_\beta$pelBmyc to replace the majority of the V$_\beta$ gene and the c-myc tag.

Construction of scV$_\alpha$V$_\beta$pelBHis ver. 2

Figure 4:
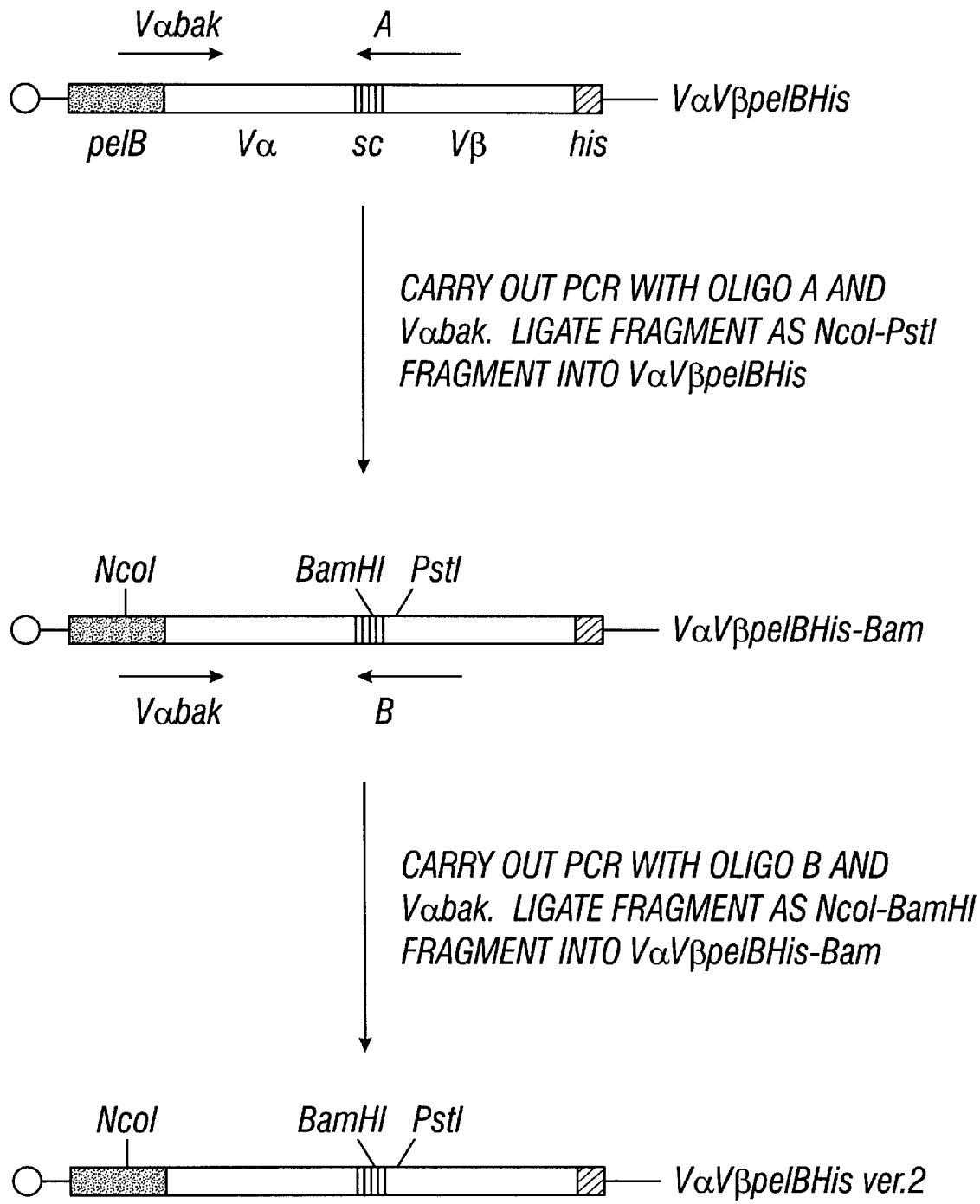
FIG. 4. Strategy for the construction of scV$_\alpha$V$_\beta$pelBHis ver.2. The pelB leader is represented by a stippled box, the $V_\alpha$ and $V_\beta$ domains by open boxes, the single chain (sc) linker peptide by vertical lines and the $(his)_6$ tag by a hatched box. The lacZ promoter is represented by an open circle. Oligonucleotides A and B are set forth in Example 1. PCR with oligonucleotide B results in the deletion of two codons between the 3' end of $J_\alpha$ and the 5' end of the $(gly_4ser)_3$ linker peptide.

A vector scV$_\alpha$V$_\beta$pelBHis ver. 2 has been constructed in which two codons (val-thr) which are located between the 3' end of the Jα gene and the 5' end of the (gly4ser)$_3$ linker have been removed, FIG. 4. These codons are derived from the 3' end of an immunoglobulin heavy chain variable domain, and may therefore interfere with the scTCR structure in the protein expressed from V$_\alpha$V$_\beta$pelBHis. The two codons were removed using PCR mutagenesis, as shown in FIG. 4, and the following primers.

Primer A (SEQ ID NO:32): 5' GTA TCT GCA GCC TCC GAT CCG CCA CCG CCG GAT CCA CCT 3'
Primer B (SEQ ID NO:33): 5' ATC AGG ATC CAC CTC CGC CTG AAC CGC CTC CAC CCG GTT TAA TGG 3'

The scTCR encoded by scV$_\alpha$V$_\beta$pelBHis ver. 2 can be secreted and purified in yields of 0.5–1 mg/liter of culture, and CD analysis indicates that the protein is folded into a similar, if not the same, structure as that encoded by sc V$_\alpha$V$_\beta$pelBHis. Thus, for practical purposes of sc TCR production the two constructs do not appear to differ.

The nucleic acid and derived amino acid sequence of the single chain construct is shown in FIG. 9 (seq id nos:7 and 8).

EXAMPLE 2

The following are examples of expression of V$_\alpha$, V$_\beta$ and V$_\alpha$V$_\beta$ T-cell receptor domains employing *E. coli* hosts transformed with the vectors of Example 1.

Expression of V$_\alpha$, V$_\beta$ and scV$_\alpha$V$_\beta$ Proteins

Figure 1A:
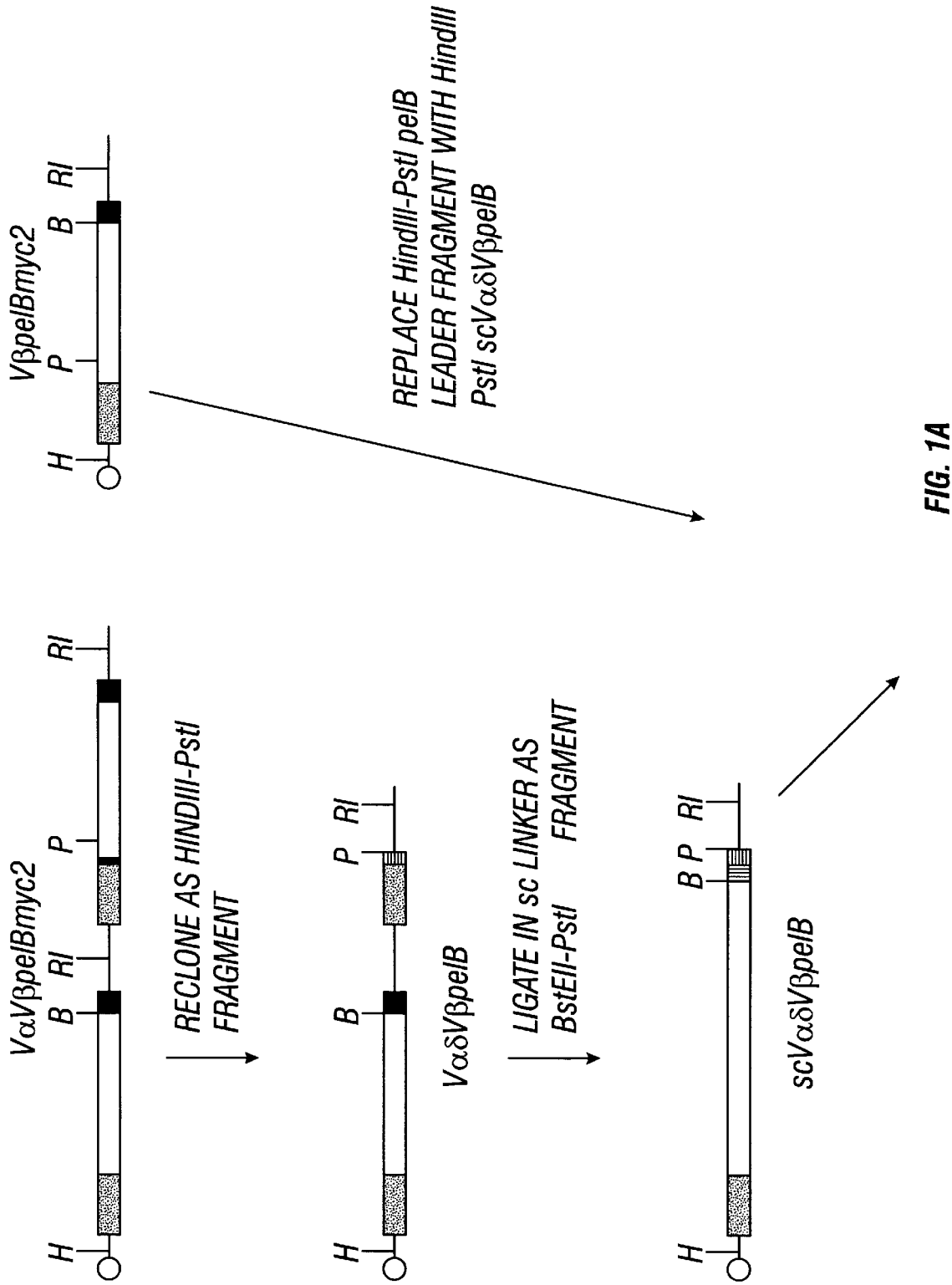
FIGS. 1A and 1B. Strategy used for construction of plasmids for expression and purification of single $V_\alpha$ and $V_\beta$ domains and scTCR $V_\alpha V_\beta$ fragments.
Figure 1B:
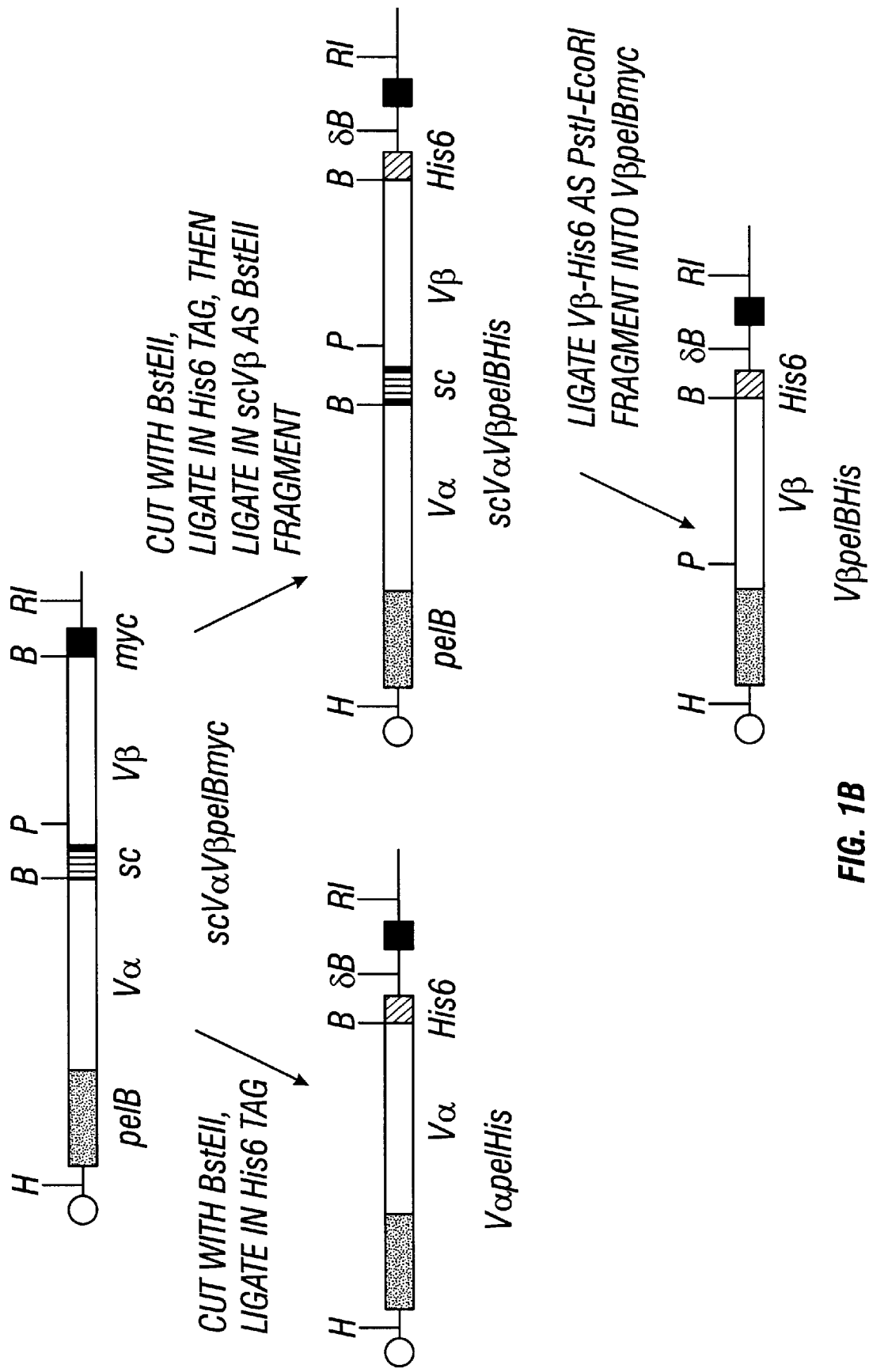
Figure 2:
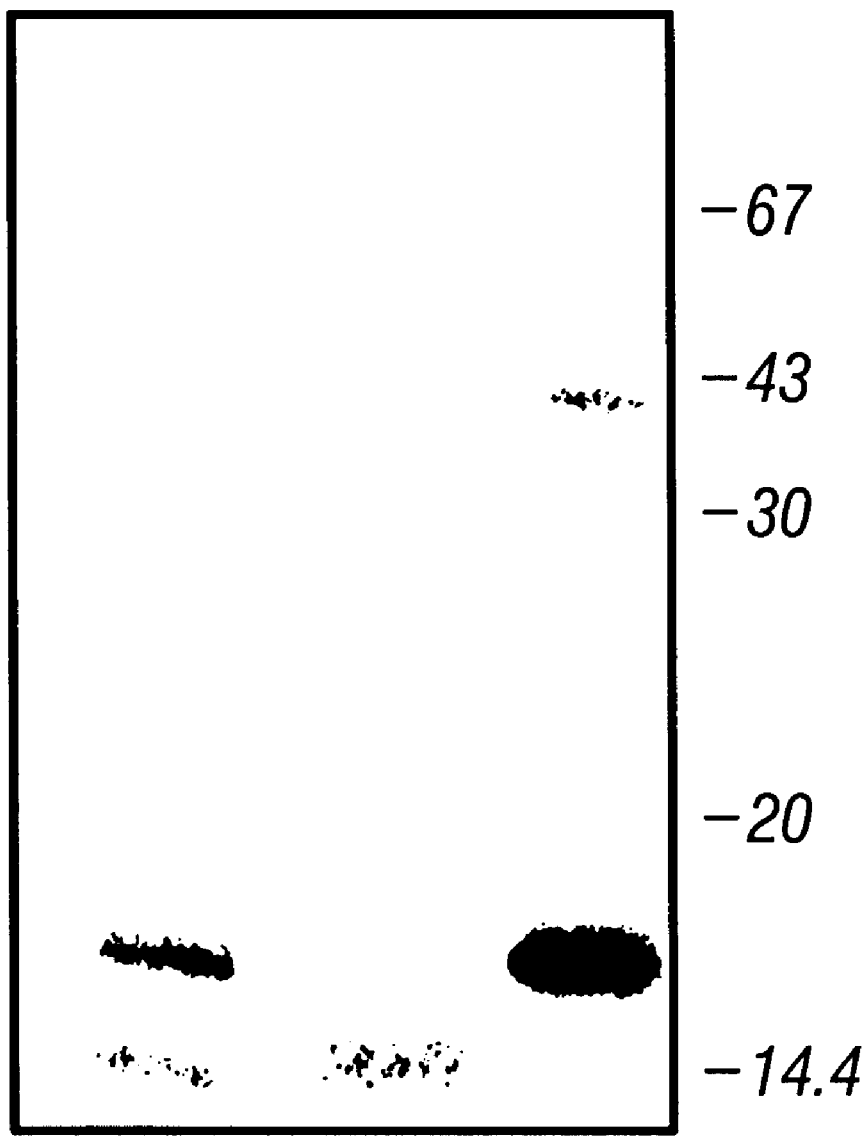
FIG. 2 (Scanned image). Expression analysis of $V_\alpha$ and $V_\beta$ domains tagged with carboxy terminal c-myc peptides by western blotting (using the 9E10 monoclonal antibody which recognizes the c-myc epitope) of culture supernatants electrophoresed) on a 15% SDS polyacrylamide gel. *E. coli* recombinants harboring the following plasmids were analyzed: lane 1, $V_\alpha V_\beta$pelBtag1; lane 2, $V_\beta$pelBtag1, and lane 3, $V_\alpha$pelBtag1. The mobilities of molecular weight size standards, run on an equivalent gel stained with Coomassie brilliant blue rather than transferred onto nitrocellulose, are indicated in kDa on the right margin.

Detection of unpurified recombinant protein in culture supernatants or osmotic shock fractions was performed as follows:

*E. coli* recombinants harboring V$_\alpha$pelBmyc, V$_\beta$pelBmyc V$_\alpha$V$_\beta$pelBmyc, or scV$_\alpha$V$_\beta$pelBmyc were grown up in 2×TY (or 4×TY) plus 100 μl ampicillin and 1% (wt:vol) glucose to early stationary phase, pelleted by centrifugation, washed once in either 2×TY (or 4×TY) or 50 mM NaCl and then induced by resuspension in 2×TY (or 4×TY) plus 100 μ/ml ampicillin and 1 mM isopropyl-β-D-thiogalactopyranoside (IPTG) for 14–16 hrs. Cultures were grown and induced at 37° C. with shaking at 250 rpm. Culture supernatants were analyzed by western blotting (Towbin et al., 1979; Ward et al., 1985) using monoclonal antibody 9E10 (Evan et al., 1985) followed by anti-mouse $F_c$ conjugated to horseradish peroxidase (ICN Immunobiologicals) for detection (FIG. 2). Diamino benzidine (Sigma, St. Louis, Mo.) was used as the horseradish peroxidase substrate. To detect expressed proteins in osmotic shock fractions the following procedure was followed.

Recombinant cells harboring $V_\alpha$pelBmyc, $V_\beta$pelBmyc, $V_\alpha V_\beta$pelBmyc or sc$V_\alpha V_\beta$pelBmyc were grown up at 30° C. for 12–16 hours in the same media as above, pelleted by centrifugation and washed in either 4×TY or 50 mM NaCl, and resuspended in 4×TY plus 100 μg/ml ampicillin plus 0.1 mM IPTG plus 1 μg/ml leupeptin (a protease inhibitor) and 10 μg/ml PMSF for 5–6 hours. Periplasmic fractions were isolated using cold TES buffer or 20% TES as described below. Osmotic shock fractions (see below) were then analyzed using Western blotting and the 9E10 monoclonal antibody as above.

Figure 10:
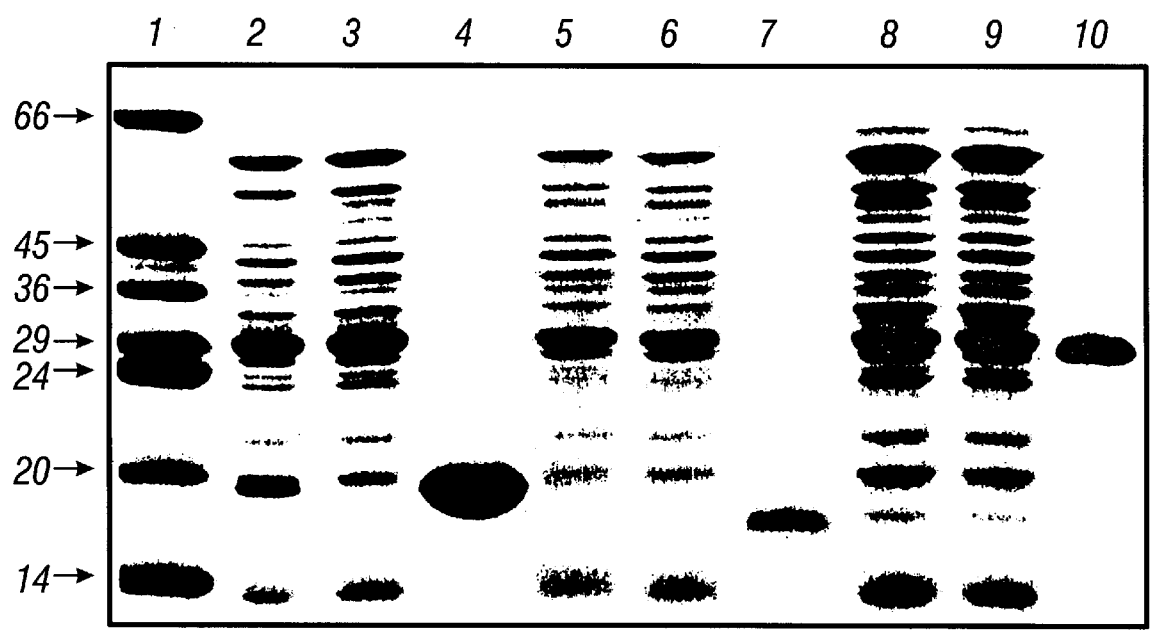
FIG. 10 (Scanned image). SDS PAGE analysis of the purified single domains (lanes 2–7) and scTCR (lanes 8–10).

For optimal yields of purified T-cell receptor proteins, recombinants harboring $V_\alpha$pelBhis, $V_\beta$pelBhis and $V_\alpha V_\beta$pelBhis were employed. 1–2 liter cultures of recombinants were grown up in 4×TY media (double strength 2×TY) plus 100 μg ampicillin/ml plus 1% (w/v) glucose for 15 hr at 30° C. Cells were pelleted by centrifugation, washed once in 4×TY and resuspended in 1 liter of 4×TY plus 100 μg ampicillin/ml, 0.1 mM-IPTG, 1 μg leupeptin/ml and 10 μg PMSF/ml and grown at 25° C. for 5–5.5 hrs. At this stage the majority of the recombinant protein was located in the periplasm, and was isolated by osmotically shocking the cells as follows:

Cells were cooled by standing on ice for 10 minutes, and then pelleted by centrifugation (6000 rpm, 15 minutes at 4° C.). Cell pellets were resuspended in cold (at 0–4° C.) 200 mM Tris-HCl pH 8.0, 500 mM sucrose and 0.5 mM Na$_2$EDTA (TES, 40 mls used per 1 liter culture). Cells were incubated in TES for 20–40 minutes at 0° C.), and then pelleted by centrifugation (10,000 rpm, 10 minutes at 4° C.). The supernatant was dialyzed against phosphate buffered saline overnight (3 changes at 4° C.). The pellets were resuspended in cold 20% v/v TES and incubated for 20–40 minutes at 0° C. The cells were again pelleted by centrifugation (10,000 rpm, 10 minutes at 4° C.), and the supernatant was dialyzed against phosphate buffered saline overnight (3 changes at 4°). Both TES and 20% TES supernatants were then passed through Ni$^{2+}$-NTA-agarose columns. Bound protein was batch eluted in 1–2 ml fractions with 250 mM imidazole, pH 9.2. To reduce non-specific binding of additional proteins, the column was washed with 500 mM NaCl/100 mM Tris HCl, pH 8, and the same at pH 7.4, prior to elution. The purified protein was dialyzed extensively against 10 mM NaH$_2$PO$_4$, pH 7.0, prior to CD analysis. Purity of T-cell receptor fragments was assessed by 15% SDS/polyacrylamide gel electrophoresis followed by staining with Coomassie brilliant blue. The SDS-PAGE stained gel of the purified proteins is shown in FIG. 10.

Yields of the purified $V_\alpha$ and $V_\beta$ domains were approximately 1–2 mg/L culture and 0.2 mg/L culture respectively. Crosslinking experiments with dithiobis (succimidylpropionate) (DSP) indicated that the $V_\alpha$ domain tended to form homodimers. To analyze the oligomeric state of the $V_\alpha$ domain, the purified protein (at a concentration of approximately 1 mg/ml in PBS) or culture supernatant from induced cultures (see above; 24 hours or more induction) was used. The purified protein was $V_\alpha$ (his)$_6$ (carboxy terminal (his)$_6$ tag) and the culture supernatant contained $V_\alpha$myc (carboxy terminal c-myc tag). 50 μl of each sample was incubated with 0.1–2 mM of DSP for one hour at room temperature. The crosslinked samples were then analyzed by SDS-PAGE (under non-reducing conditions) followed by either staining with Coomassie brilliant blue (for $V_\alpha$(his)$_6$) or Western blotting (for $V_\alpha$myc). For the Western blotting, the $V_\alpha$ domain was detected using the 9E10 monoclonal antibody as above. For a significant proportion of $V_\alpha$ domain, the size following incubation with crosslinker was approximately 30 kDa, indicating the formation of homodimers.

As a single chain polypeptide, the 1934.4 hybridoma cell-derived scTCR with a (his)$_6$ peptide tag was secreted into the periplasm and purified using Ni$^{2+}$-NTA-agarose in yields of about 0.5–1.0 mg/l culture. The lower growth and induction temperature and lower IPTG concentration (0.1 mM), about 25° C., was particularly beneficial in inducing higher expression yields for the single chain $V_\alpha V_\beta$ heterodimer.

An alternative purification of the single chain $V_\alpha V_\beta$ domain employed an antibody-linked sepharose column. The purification of the scTCR by affinity chromatography indicated epitopic recognition by the antibody employed, monoclonal antibody KJ16 which is specific for murine $V_{\beta 8}$ (Kappler et al., 1988).

EXAMPLE 3

The following example illustrates that the expression vectors of Example 1 are not limited to expression in *E. coli*. *Serratia marcescens* was employed as host in the following example.

Expression and Secretion of TCR Single Chain TCRs from *S. marcescens*

The plasmid sc$V_\alpha V_\beta$pelBhis was transformed into *S. marcescens* by electroporation and transformants selected on 2×TY agar plates with 1 mg/ml ampicillin and 1% w/v glucose, or minimal media (Sambrook et al., 1989) plates plus 1 mg/ml ampicillin plus 1 w/v glucose. Transformants were grown up in minimal media plus 10% w/v casamino acids, 5% w/v glycerol, 0.5 mg/ml ampicillin (MCGA media) at 30° C. for 24 hrs with aeration (250 rpm). 30–50 ml of this culture was used to inoculate 500 ml of the same MCGA media and grown for 12–16 hrs overnight at 30° C. with aeration (250 rpm) and then IPTG added to a final concentration of 0.2–0.5 mM. Cells were induced for 12–24 hrs by growth at 30° C. with aeration (250 rpm) and then stood on ice for 10 min. Cells were pelleted by centrifugation for 30 min, 10,000 rpm, followed by 30 min at 14,000 rpm and the supernatant filtered through a 0.45 μm filter unit (Nalgene). The supernatant was concentrated 10–20 fold in a high pressure concentrator with a YM10 filter and then dialyzed overnight (3 changes) against PBS at 4° C. The dialyzed supernatant was passed through a Ni$^{2+}$-NTA-agarose column using the procedure for isolation from *E. coli* host according to Example 2.

Alternatively, the *S. marcescens* recombinants may be induced for shorter time periods and the protein isolated from the periplasmic space by osmotic shocking. Yields are higher if longer induction periods are employed and the protein isolated from culture supernatant.

EXAMPLE 4

The following example relates to an analysis of the folded state of the recombinant TCR fragments using circular dichroism (CD) analysis. Results indicated a significant proportion of β-sheet structure, indicative of native folding.

Circular Dichroism Analysis of Expressed TCR Proteins

FIG. 11 shows the circular dichroism spectra of recombinant TCR proteins. The recombinant TCR fragments were purified using the methodology described above, from *E. coli* cells harboring $V_\alpha$pelBhis, $V_\beta$pelBhis and sc$V_\alpha V_\beta$pelBhis and dialyzed into 10 mM sodium phosphate pH7.0 prior to CD analysis. As a comparison, the immunoglobulin scFv fragment derived from the D1.3 antibody (Ward et al., 1989) was purified and used. This fragment was expressed from a plasmid construction derivative of pSW2 (Ward et al., 1989; McCafferty et al., 1990). The scFv was purified from the culture supernatant of induced cultures using lysozyme sepharose (Ward et al., 1989) and dialyzed against 10 mM sodium phosphate pH 7.0 prior to analysis in CD. The rationale for using this immunoglobulin fragment as a comparison is that molecular modeling indicates that the $V_\alpha$ and $V_\beta$ domains of TCRs resemble immunoglobulin variable domains (Chothia et al., 1988; Novotny et al., 1986). For each recombinant TCR protein, several spectra were generated using different concentrations and/or protein from different purification batches. FIG. 11 shows representative spectra.

CD analyses were carried out using an AVIV model 60DS circular dichroism spectrophotometer at 25° C. and a cell path of 0.2 cm. Concentrations of proteins in 10 mM $NaH_2PO_4$ varied from 1.0 μM to 7.8 μM. Concentration of the purified proteins was determined by quantitative amino acid hydrolysis. Proteins examined were $V_\alpha(his)_6$, $V_\beta(his)_6$, scTCR$V_\alpha V_\beta(his)_6$ and D1.3scFv.

By comparison with both the CD spectrum of the structurally solved D1.3 Fv fragment (Bhat et al., 1990) and that of other proteins known to have a high proportion of β-pleated sheet structure, it was concluded that the CD spectra of the recombinant TCR fragments contained a high proportion of β-pleated sheet structure. This is consistent with the molecular modeling studies which indicate that the TCR domain fold is immunoglobulin-like in character (Chothia et al., 1988; Novotny et al., 1986). The features of the spectra are: i) a minima at 218 nm, indicative of β-pleated sheet structure, ii) no minima at the wavelengths which are characteristic of α helical structure (Johnson, 1990), implying that there is no α helical structure in the TCR domains which is consistent with molecular models, iii) no maxima at the wavelength expected for random coil structure (Johnson, 1990), indicating that at least the majority of the TCR domains are folded into secondary structure and not in denatured (unfolded) state, and iv) for the $V_\alpha$ domain and D1.3 scF$_v$, a maxima at 205 nm indicating the presence of β turns.

EXAMPLE 5

The following example illustrates the production of an immunoglobulin Fc-hinge or Fc fragment and Fc-hinge or Fc derived subfragments in milligram quantities using *E. coli* as an expression host. These results indicate the suitability of the system for the commercial production of large quantities of recombinant protein.

Plasmids, Expression and Purification

PCR was used to isolate and tailor the genes encoding fragments derived from the murine IgG1 immunoglobulin molecule 9E10 (Honjo et al., 1979; Evan et al., 1985) for ligation into the expression plasmids (FIG. 12). To accomplish this, total RNA was extracted from 1×10$^7$ 9E10 hybridoma cells, as described herein above. cDNA was primed using oligonucleotides CH3forBst or CH2forBst (see below; Honjo et al., 1979) for the isolation of either the CH3 domain gene/Fc fragment genes or the CH2 domain gene respectively. The genes were then isolated using PCR and the primers shown below. As listed, the five distinct sequences represent seq id no:9 through seq id no:13, respectively.

a) CH3 domain,
CH3bakNco (SEQ ID NO: 9)=5' ATC ACC ATG GCC GGC AGA CCG AAG GCT CCA CAG 3;
CH3forBst (SEQ ID NO: 10)=5' TAC AGG TGA CCT TAC CAG GAG AGT GGG AGA GGC T 3' b) CH2-hinge,
HingebakNco (SEQ ID NO: 11)=5' ATC ACC ATG GCC GTG CCC AGG GAT TGT GGT TG 3'
CH2forBst (SEQ ID NO: 12)=5' ATC AGG TGA CCT TGG TTT TGG AGA TGG TTT T 3' c) Fc fragment,
CH2bakNco (SEQ ID NO: 13)=5' ATC ACC ATG GCC GAA GTA TCA TCT GTC TTC ATC 3'
CH3forBst; as above d) Fc-hinge fragment,
HingebakNco and CH3forBst; both as above A typical PCR comprised: 3 units Promega Taq polymerase, 10 μl Promega buffer, 10 μl 0.2 mM dNTP cDNA synthesis reaction in a final volume of 100 μl. Cycling conditions were: 94° C. (0.5 min), 55° C. (0.5 min), 72° C. (1 min) for thirty cycles using a Techne temperature cycling block. The oligonucleotides each encode either an NcoI or BstEII restriction site indicated by underlining, and italicized sequences) indicate the regions of the oligonucleotides that anneal to murine IgG1 constant region genes (Honjo et al., 1979); which allows restriction digestion of the PCR products followed by gel purification and ligation as NcoI-BstEII fragments into V$\alpha$pelβHis (Ward, 1992). The ligated DNA was then transformed into *E. coli* BMH 71-18, as described above. The sequences of the inserts of all plasmid constructions were analyzed using the dideoxynucleotide method and either Sequenase (USB) for single stranded DNA templates and Femtomole kits (Promega) for double stranded DNA templates.

These antibody fragments can be expressed and secreted from recombinant *E. coli* cells, and the carboxy-terminal His$_6$ peptide tags allow purification using Ni$^{2+}$-NTA-agarose. *E. coli* BMH 71-18 transformants harboring the plasmids shown in FIG. 12 were grown up and induced for expression as described herein above. The recombinant proteins were isolated from the periplasm by osmotic shock followed by affinity purification using Ni$^{2+}$-NTA-agarose. The recombinant fragments were purified in yields of 2, 1–1.5, 1.5–2 and 0.5–1 milligrams per litre of culture for the CH3 domain, CH2-hinge fragment, Fc fragment and Fc-hinge fragment respectively. The purity of the recombinant proteins was assessed using SDS gel electrophoresis (Laemmli) and staining with Coomassie blue R-250 (FIG. 13).

For derivatization of the CH2-hinge fragments with Ellman's reagent, the following procedure was used: CH2-hinge at a concentration of 1 mg/ml in 50 mM sodium phosphate buffer pH 7.5–8.0 was incubated with a 100 molar excess of Ellman's reagent (Pierce) dissolved in dimethyl formamide. Following incubation at room temperature for several hours, the derivatized CH2-hinge fragment was separated from free Ellman's reagent on a G-25 column. The Ellmanised CH2-hinge fragment was then incubated with an equimolar amount of underivatized CH2-hinge in 50 mM sodium phosphate buffer, pH 7.5, at room temperature. The reaction was monitored by measuring the optical density at 412 nm. When the optical density remained constant, the monomeric CH2-hinge was separated from dimeric CH2-hinge using gel filtration.

In vitro Structural Analyses Results from HPLC analyses indicated that the CH3 domain, Fc fragment and Fc-hinge fragment are all expressed and purified as homodimeric proteins. For the Fc and CH3 domain, the dimers are non-covalently linked, as demonstrated by analyses on non-reducing PAGE (FIG. 13B). The dimerization of the Fc fragments and CH3 domains is presumably stabilized by non-covalent interactions between the CH3 fragments, which are closely apposed in the immunoglobulin structure (Marquart et al., 1980). For the Fc-hinge dimer, the fragments are also covalently linked by —S—S— bridges between the hinge region cysteines (FIG. 13).

In contrast, analysis of the CH2-hinge fragment using HPLC indicates that approximately 10% of the protein is expressed and purified as a dimer, and the remainder as monomers. Structural analyses of immunoglobulins indicate that the CH2 domains in the Fc region of an antibody molecule form few interactions, and presumably the relative weakness of these interactions (compared with those between CH3 domain, for example) result in a low proportion of expressed dimers. The dimers are covalently linked by —S—S— bridges (FIG. 13); expression and purification of CH2 domain without the hinge region resulted in a significant proportion of this protein forming dimers that are non-covalently linked, and in addition, there are no free sulphydryls as would be expected for an immunoglobulin domain that is correctly folded with intramolecular —S—S— bridges. This suggests that in the CH2-hinge fragments, the —S—S— bridges are formed between cysteine residues located in the hinge region.

EXAMPLE 6

The following example illustrates that the native sequence immunoglobulin Fc-hinge and Fc fragments, purified following expression in $E.\ coli$, have similar in vivo stability to the native IgG1 antibody molecule.

To determine the clearance rates of the immunoglobulin fragments in vivo, the recombinant proteins were radiolabeled with $^{125}$I and the levels of serum radiolabel monitored as a function of time. The clearance rates were then compared with those of intact murine IgG1 (expressed and purified from a hybridoma) and the bacterially expressed D1.3 Fv fragment (Ward et al., 1989) derived from the murine D1.3 antibody. The clearance curves were all found to be biphasic (FIG. 14). The half lives of the α and β phases are shown in Table I. For the D1.3 Fv, CH2-hinge and CH3 fragments the α phases were too rapid to be accurately determined (FIG. 14).

From the clearance rate data, several conclusions can be drawn. Firstly, the recombinant aglycosylated Fc fragments (with or without the hinge region) have the same stability in vivo as the complete glycosylated IgG1 molecule. The shorter half life of the α phase, which represents the equilibration phase between the vascular and extravascular tissue, is shorter for the recombinant Fc-hinge or Fc fragments due to their smaller size. Secondly, both the CH3 domain and CH2-hinge fragment are cleared at rates similar to that of the D1.3 Fv fragment (FIG. 14).

TABLE I

Half lives of the β phases of the immunoglobulin fragments

| Immunoglobulin (fragment) | β-phase (half life in hours) |
|---|---|
| CH2 + Hinge | 24.5 |
| [CH2 + Hinge]₂ | 26.8 |
| CH3 | 13.8 |
| Fc | — |
| Fv | 20 |
| Fc-hinge | 66.3 |
| Complete immunoglobulin | 85 |
| Glycosylated Fc-hinge | — |

Recombinant immunoglobulin fragments were purified and radiolabeled using either the Bolton Hunter reagent (Amersham, 2000 Ci/mmol) or Iodogen (Amersham) to a specific activity of $10^5$–$10^7$ cpm/μg of protein. The complete IgG1 antibody used as a control was purified from mammalian cells using standard methodology. The glycosylated Fc-hinge fragment was derived from this IgG1 antibody by papain digestion followed by purification using protein A sepharose (Pierce). For the measurement of the half lives, 2–4 BALB/c mice (23–28 gms, female) were injected with 0.1 ml of radiolabeled protein (approximately 1–50 μg protein containing $10^6$–$10^7$ cpm) in the tail or retro-orbitally, and bled retro-orbitally at time points from 2 mins-72 hours post injection. The amount of radioactivity present in the blood samples was determined using a Scintillation counter.

A high proportion (approximately 90%) of the CH2-hinge fragment was expressed and purified in monomeric rather than dimeric form, and therefore the possibility remained that the determinants of stability are located on the CH2-hinge dimer. To determine whether CH2-hinge dimers was stable in vivo, dimers of the CH2-hinge fragments were generated by derivatizing an aliquot of the purified CH2-hinge fragments with Ellman's reagent (FIG. 13), and then mixing this with an equimolar of underivatized CH2-hinge fragment. HPLC analysis indicated that this resulted in approximately 90% dimerization, and this dimer was used in clearance studies. The half life of the α phase of this dimer is slightly longer than that of the predominantly monomeric CH2-hinge domain, due to the twofold difference in molecular size. The β phase is, however, indistinguishable from that of the monomeric form, indicating that the rapid clearance of the CH2-hinge is not due to the monomeric state.

These data demonstrate that recombinant aglycosylated Fc fragments, with or without hinge regions, have a β phase that is similar to that of a complete glycosylated IgG1 immunoglobulin molecule. Therefore, the carbohydrate residues do not appear to play a major role in stability. In addition, the hinge is not necessary for in vivo stability. In contrast, both dimeric CH2-hinge and CH3 fragments are catabolized as rapidly as antibody Fv fragments, indicating that the presence of sequences in both the CH2 and CH3 domains are necessary for the in vivo stability of the recombinant Fc-hinge or Fc fragment. The production of the IgG1 Fc-hinge or Fc fragment in $E.\ coli$ is envisioned to allow the delineation of the key residues involved in controlling the catabolism of the immunoglobulin molecule in vivo. In light of the present work, the production and analysis of human Fc regions in $E.\ coli$ is now possible. It is envisioned that this work will also lead to the development of novel tagging and stabilization methods for use with various recombinant molecules employed in animal or human therapeutics.

EXAMPLE 7

The following example illustrates the design and bacterial production of engineered immunoglobulin Fc-hinge fragments, the delineation of the site that controls IgG1 catabolism and, thereby, the production of antibody fragments that have reduced in vivo half lives.

Plasmids, Expression and Purification

The methods employed in the present example are based upon those described in detail in Example 5. Mutations were made using designed mutagenic oligonucleotides and either PCR mutagenesis (as described hereinabove, I-253) or site-directed mutagenesis (as described hereinabove, HQ-310, HN-433). The oligonucleotides employed were as listed below, with the three distinct sequences representing seq id no:14 through seq id no:16, respectively.

i) I-253 (SEQ ID NO: 14):

5' ATC TAC ACG TGA CCT TAG GAG TCA GAG TA G CGG TGA G 3';

ii) HQ-310 (SEQ ID NO: 15);

5' GAG CCA GTC GTT GGC CAT GAT GGG AAG 3';

iii) HN-433 (SEQ ID NO: 16):

5' AGT ATG GTG TTG GGC CAG GCC CTC ATG 3'.

Oligonucleotides are shown in reverse complement to coding strand and mutated bases are indicated by underling. For the I-253 mutant, oligonucleotide i) and the reverse universal M13 sequencing primer (New England Biolabs) was used in the PCR with wild-type Fc-hinge DNA as template. The AflIII site (present in the wild type Fc-hinge gene (Honjo et al., 1979) used for cloning of the mutant DNA to replace the corresponding wild type sequences is indicated by italics. The HQ-310/HN-433 mutant was made by a three way ligation of an NcoI-MscI fragment containing the 5' 416 bp of the Fc-hinge HQ-310 mutant and an MscI-BstEII fragment containing the 3' 265 bp of the Fc-hinge HN-433 mutant. All mutated genes were sequenced (Sequenase, USB or Femtomole, Promega) prior to functional analyses.

Figures 2, 15B:
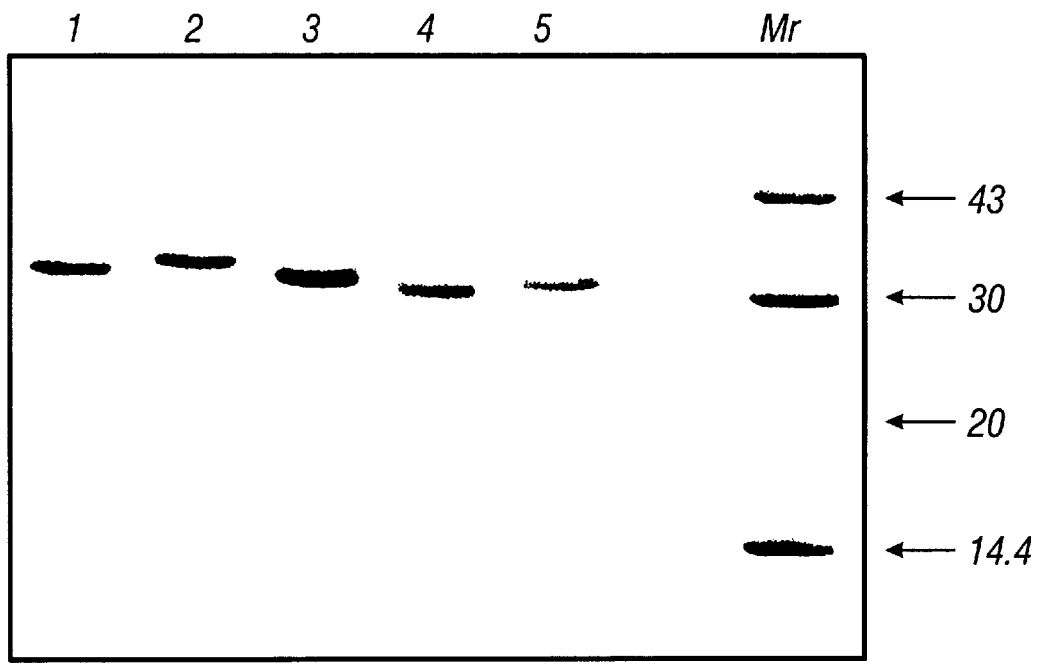

Plasmids encoding wild type IgG1 Fc-hinge, and mutants I-253, HQ-310, HN-433 and HQ-310/HN-433 were constructed for this study (FIG. 15, Panel A). The residues that were been mutated are all in close proximity to the CH2–CH3 domain interface (Deisenhofer 1981) and are also conserved in most of the IgG isotypes in both mouse and man (Kabat et al., 1991). The details of these mutants are represented below in Table II:

TABLE II

Reduced Half-Life Fc-Hinge Mutants

| | | |
|---|---|---|
| I-253 | a single mutant | ile 253 to ala 253 |
| HQ-310 | a double mutant | his 310 to ala 310; and gln 311 to asn 311 |
| HN-433 | a double mutant | his 433 to ala 433; and asn 434 to gln 434 |
| HQ-310/HN-433 | a tetra-mutant | his 310 to ala 310; gln 311 to asn 311; his 433 to ala 433; and asn 434 to gln 434 |

The wild type and mutant Fc-hinge fragments were expressed and purified from recombinant *E. coli* cells in yields of 0.5 milligrams per liter. These fragments were purified using $Ni^{2+}$-NTA-agarose as described hereinabove and in (Ward, 1992). Analyses using reducing and non-reducing SDS-PAGE (Laemmli, 1988, with Coomassie brilliant blue R250 staining) indicated that the wild type and mutant Fc-hinge fragments were expressed as sulphydryl linked homodimers (FIG. 15b).

In Vivo Stability and Catabolism

The proteins were radiolabeled with 125-I Na using the Iodo-gen method (Amersham). The free iodine was removed by two successive gel filtrations on Sepharose G-25M using tuberculin syringe columns and low speed centrifugation. The final volume of radiolabeled protein was adjusted to 0.5–0.7 ml with phosphate buffered saline (pH 7.2) containing 1 mg/ml BSA. The specific activity of the radiolabeled proteins were approximately $10^7$ cpm/µg, with less than 5% free iodine. All radiolabeled Fc-hinge fragments were analyzed on SEC-250 (Bio-Rad) column by permeation HPLC and emerged as single peaks with retention times corresponding to 55 kDa—which indicated that was no detectable radiolysis of the proteins.

To analyze the clearance of the various fragments, studies based upon the following method were employed. BALB/c mice (20–25 gms) were given 0.1% NaI in drinking water one date prior to injection and throughout the period of monitoring the clearance of the radiolabeled proteins. The radiolabeled proteins were injected intravenously through the tail vein in a volume not larger than 150 µl and with a radioactive load of 10–50×$10^6$ cpm. The mice were bled with heparinized 50 µl capillary tubes from the retro-orbital sinus three minutes following injection and at the time intervals indicated on FIG. 16. The plasma was collected by centrifugation and kept at −20° C. The radioactivity was measured on an LKB gama counter using 25 µl of plasma before and after precipitation with 10% trichloroacetic acid (TCA). In all cases, greater than 90% of the plasma counts were precipitated by 10% TCA. The plasma collected from mice at 24 hours was pooled and analyzed by HPLC on SEC-250 columns. It was not possible to inject exact volumes of radiolabeled protein into each animal, and the results (FIG. 16) are therefore expressed relative to the amount of plasma radioactivity at 3 minutes post-injection.

Following injection of the radiolabeled proteins into groups of 3–4 mice, as described above, the serum radioactivity was monitored at various time intervals. For each fragment, it was found that the clearance curves in different mice were almost identical (FIG. 17 shows representative curves for one mouse from within each group0. For each recombinant protein, the plasma samples collected at the 24 hour time point from mice within one group were pooled and subjected to HPLC on SEC-250 columns. 90% of the radioactivity was eluted as a major peak that had a retention time identical to that of the corresponding material prior to injection for all the Fc-hinged fragments. This indicates that the wild type and mutant Fc-hinge fragments persist in the serum as intact molecules, and are not associated with other serum proteins.

The pharmacokinetic parameters of the wild type and mutant Fc-hinge fragments are shown in Table III. These data indicate that the mutations have significant effects on the half lives of both the α and β phases of the IgG1 Fc-hinge fragment. Mutations in the CH2 domain (I-253 and HQ-310) have a more marked effect than those in the CH3 domain (HN-433). The HN-433 mutant is cleared with pharmacokinetics that are similar to those of the isolated CH2-hinge fragment, as disclosed hereinabove, suggesting that these CH3 domain mutations have eliminated the involvement of this domain in maintaining serum levels. The HQ-310/HN-433 mutant is cleared more rapidly than either of the two mutants from which it is derived. The mean residence times, areas under curves and plasma clearance figures are consistent with the calculated values for the half lives of the α and β phases (Table III).

TABLE III

Pharmacokinetic parameters of the wild type and mutant Fc-hinge fragments

| Fc-hinge Fragment | α phase $t_{1/2}$ (hours) | β phase $t_{1/2}$ (hours) | MRT* (hours) | AUC# (total; ng/hour/ml) | PC@ (ng/hour) |
|---|---|---|---|---|---|
| Wild type | 10.46 ± 0.78 | 82.88 ± 10.05 | 104.4 ± 12.8 | 1949 ± 256.9 | 5.36 ± 0.79 |
| I-253 | 6.68 ± 0.15 | 20.03 ± 0.62 | 16.3 ± 0.82 | 548 ± 27.1 | 22.5 ± 1.15 |
| HQ-310 | 5.97 ± 0.62 | 17.5 ± 1.62 | 12.14 ± 1.03 | 528.0 ± 126.6 | 20.39 ± 4.67 |
| HN-433 | 10.25 ± 1.21 | 50.32 ± 2.92 | 60.02 ± 5.06 | 1469 ± 231.6 | 6.86 ± 0.91 |
| HQ-310/ HN-433 | 5.81 ± 0.20 | 15.57 ± 0.79 | 10.41 ± 0.62 | 529.4 ± 69.7 | 20.97 ± 4.25 |

MRT* = mean residence time; AUC# = area under curve; PC@ = plasma clearance rate. All radioactive counts that were used to calculate the pharmacokinetics were more than 50 times greater than background (30 cpm). The half lives of the α and β phases were determined using a noncompartmental model provided by a computer program of Dr. K. Vyas, Merck, Sharp and Dohme Research Laboratories, West Point, Pennsylvania. For the α phases, data points between 0.05 and 24 hours were used for all fragments. For the β phases, data points between either 24 and 164 hours (wild type and HN-433) or 24 and 96 hours (I-253, HQ-310, HQ-310/HN-433) were used. The pharmacokinetic parameters for the recombinant proteins were analyzed in two independent experiments using 3–4 animals for wild type and mutant Fc-hinge fragments, with the exception of the I-253 mutant which was analyzed in one experiment in 4 mice.

Binding to SpA

The effect of the mutations on binding of the Fc-hinge fragment to SpA were analyzed in competition binding studies as follows. 100 µl of packed SpA-agarose gel was suspended in 250 µl of sodium phosphate buffer (0.05 M, pH 7.5) containing 3 mM EDTANa$_2$ and 1 mg/ml bolvine serum albumin (PBE/BSA). Unlabelled wild type or mutant Fc-hinge fragments were added in varying amounts (7.5 µg to 100 µg). All incubations were made up to a final volume of 500 µl with PBE/BSA and incubated at room temperature with occasional stirring for 30 minutes. A constant amount of $^{125}$I-labelled wild type Fc-hinge fragment (1 µg with a specific activity of approximately 2×10$^6$ cpm/µg) was added to each tube and further incubated at room temperature for 90 minutes with occasional stirring. The SpA-agarose gel was washed 4 times with PBE/BSA using centrifugation to pellet the gel. Bound radioactivity was counted in an LKB gamma counter. The relative affinity of the mutant Fc-hinge fragments for protein A was calculated from the slope of the curves shown in FIG. 17.

In the above manner, the ability of the mutants to compete with radiolabeled wild type fragment for binding to SpA-agarose was determined and compared with the competitive ability of the wild type Fc-hinge fragment (FIG. 17). The results of these studies indicated that all of the mutants are impaired in SpA binding, and the least active mutant (HQ-310/HN-433) had undetectable binding activity. These data are consistent with the crystallographic structure of the SpA-IgG1 complex (Deisenhofer, 1981). In addition, for each mutant the decrease in SpA binding activity correlated with the corresponding increase in catabolic rates, with mutations in the CH2 domain having a greater effect (in particular, HQ-310) than those in the CH3 domain.

To eliminate the possibility that the increased clearance rates and decreased SpA binding activities of the mutants were due misfolding of the mutant Fc-hinge fragments, the circular dichroism (CD) spectra of the mutants were compared with that of the wild type Fc-hinge fragment in the range 190–260 nm. It was found that the spectra showed no significant differences. In addition, temperature denaturation analyses using CD indicated that the mutant and wild type Fc-hinge fragment behaved similarly under the conditions used (10 mM sodium phosphate, pH 7.0). The mutants also formed sulphydryl linked dimers (FIG. 15b) that showed no tendency to aggregate. The data therefore suggest that the Fc-hinge fragments described in this study are not misfolded as a result of the mutations.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

REFERENCES

The references listed below are incorporated herein by reference to the extent that they supplement, explain, provide a background for or teach methodology, techniques, and/or compositions employed herein.

Adelman, J. P., Hayflick, J. S., Vasser, M. and Seebury, P. H. *DNA* 2/3, 183–193 (1983).
Amit, A. G., Mariuzza, R. A., Phillips, S. E. V., and Poljak, R. J., *Science,* 233:747–752 (1986).
Better, M., Chang, C. P., Robinson, R. R. and Horwitz, A. H. *Science,* 240, 1041–1043 (1988).
Bhat, T. N., Bentley, G. A., Fischmann, T. O., Boulot, G. and Poljak, R. J. *Nature,* 347, 483–485 (1990).
Borst et al., 1987, *Nature* 325, 683–688.
Brambell, F. W. R., Hemmings, W. A. and Morris, I. G., *Nature,* 203, 1352–1355.
Brenner et al., 1986, *Nature* 322, 145–149.
Carter, P. J., Bedouelle, H., Winter, G. *Nucleic Acids Res.,* 13, 4431–4443 (1985).
Chothia, C., Boswell, D. R. and Lesk, A. M. *EMBO J.,* 7, 3745–3755 (1986)
Deisenhofer, J., *Biochemistry,* 20, 2361-(1981).
Devaux, B., Bjorkman, P. J., Stevenson, C., Greif, W., Elliot, J. F., Sagerström, C., Clayberger, C., Krensky, A. M. and Davis, M. M. *Eur. J. Immunol.,* 21, 2111–2119 (1991).
Dima, D. S., Medesan, C., Mota, G., Moraru, I., Sjöquist, J. and Ghetie, V., *Eur. J. Immunol.,* 13, 605–614 (1983).
Duncan, A. R., Woof, J. M., Partridge, L. J., Burton, D. R. and Winter, G., *Nature,* 332, 563–563 (1988).
Edelman, G. M., Cunningham, B. A., Gall, W. E., Gottlieb, Ph.D., Rutishauser, U. and Waxdal, M. J. *Proc. Natl. Acad. Sci. USA,* 63, 78–85 (1969).
Ellerson, J. R., Yasmeen, D., Painter, R. H., and Dorrington, K. J., *J. Immunol.,* 116(2):510–517 (1976).
Evan, G. I., Lewis, G. K., Ramsay, G. and Bishop, J. M. *Mol. Cell. Biol.,* 5, 3610–3616 (1985).
Fleury, S., Lamarre, D., Meloche, S., Ryu, S-E., Cantin, C., Hendrickson, W. A. and Sekaly, R-P. *Cell,* 66, 1037–1049 (1991).
Gascoigne, N. R. J. *J. Biol. Chem.,* 265, 9296–9301 (1990).
Gregoire, C., Rebai, N., Schweisguth, F., Necker, A., Mazza, G., Auphan, N., Millward, A., Schmitt-Verhulst, A-M. and Malissen, B. *Proc. Natl. Acad. Sci. USA,* 88, 8077–8081 (1991).

Harding, C. V. and Unanue, E. R. *Nature,* 346, 574–576 (1990).

Hogg, Nancy, *Immunology Today,* 9(7 & 8): 185–193 (1988).

Honjo, Tasuku, Obata, Masanori, Yamawaki-Kataoka, Yuriko, Kataoka, Tohru, Kawakami, Toshiaki, Takahashi, Naoki, and Mano, Yoshitake, *Cell,* 18:559–568, 1979.

Howell, M. D., Winters, S. T., Olee, T., Powell, H. C., Carlo, D. J., Brostoff, S. W. *Science,* 246, 668–670 (1989).

Huston, J. S., Levinson, D., Mudgett-Hunter, M., Tai, M-S, Novotny, J., Margolies, M. N., Ridge, R. J., Bruccoleri, R. E., Haber, E., Crea, R. and Opperman, H. *Proc. Natl. Acad. Sci. USA,* 85, 5879–5883 (1988).

Johnson, W. C. *Proteins,* 7, 205–214 (1990).

Kabat, E. A., Wu, T. T., Perry, H. M., Gottesman, K. S. and Foeller, C., In: "Sequences of Proteins of Immunological Interest," U.S. Department of Helath and Human Services (1991).

Kappler, J. W., Staerz, U., White, J. and Marrack, P. C. *Nature,* 332, 35–40 (1988).

Kyte & Doolittle, *J. Mol. Biol.* 157:105–132 (1982)

Laemmli, U. K., *Nature,* 227, 680–685 (1970).

Leatherbarrow, R. J., Rademacher, Thomas W., and Dwek, Raymond A., *Molecular Immunology,* 22(4) :407–415 (1985).

Lin, A. Y., Devaux, B., Green, A., Sagerstrom, C. Elliott, J. F. and Davis, M. M. *Science,* 249, 677–679 (1990).

Lund, J. et al., *J. Immunol.,* 147, 2657–2662 (1991).

McCafferty et al., *Nature* 348, 552 (1990).

Mariuzza, R. A. and Winter, G. P., *J. Biol. Chem.,* 264, 7310–7316 (1989).

Marquart, Markus, Deisenhofer, Johann, and Huber, Robert, *J. Mol. Biol.,* 141:369–391 (1980).

Messing, et al., 1981, *Nacl. Acids Res.,* 9, 309.

Mueller, B. M., Reisfeld, Ralph A., and Gillies, Stephen D., *Proc. Natl. Acad. Sci. USA,* 87:5702–5705 (1990).

Narang, S. A., Brousseau, R. Hsuing, H. M., and Michniewicz, J. J., *Methods in Enzymology,* 65:610 (1980).

Nose, Masato, Takano, Tyo, Nakamura, Satoshi, Arata, Yoji, and Kyogoku, Masahisa, *International Immunology,* 2(11):1109–1112 (1990).

Nose, Masato, and Wigzell, Hans, *Proc. Natl. Acad. Sci. USA,* 80:6632–6636 (1983).

Novotny, J., Tonegawa, S., Saito, H., Kranz, D. M. and Eisen, H. N. *Proc. Natl. Acad. Sci. USA,* 83, 742–746 (1986).

Novotny, J., Gahjn, R. K., Smiley, S. T., Hussey, R. E., Luther, M. A., Recry, M. A., Siciliaro, R. F. and Reinher, E. L. (1991) *Proc. Natl Acad. Sci, USA,* 88, 8646–8650.

Offner, H., Hashim, G. A., Vandenbark, A. A. *Science,* 251, 430–432 (1991).

Pollock, Roberta R., French, Deborah L., Metlay, Joshua P., Birshtein, Barbara K., and Scharff, Matthew D., *Eur. J. Immunol.,* 20:2021–2027, 1990.

Rüther, U., Koenen, M., Otto, K. and Müller-Hill, B. *Nucl. Acids Res.,* 9, 4087–4098 (1981).

Saiki, R. K., Gelfand, D. H., Stoffel, S., Scharf, S. J., Higuchi, R., Horn, G. T., Mullis, K. V. and Erlich, H. A. *Science* 239, 487–491 (1988).

Sambrook, J., Fritsch, E. F. and Maniatis, T. Molecular Cloning; a Laboratory Manual, Cold Spring Harbor Press, 1989.

Sleckman, B. P., Peterson, A., Jones, W. K., Foran, J. A., Greenstein, J. L., Seed, B. and Burakoff, S. J. *Nature,* 328, 351–353 (1987).

Skerra, A. and Plückthun, A. *Science,* 240, 1038–1041 (1988).

Spiegelberg, H. L. and Weigle, W. O., *J. Exp. Med.,* 121, 323–328 (1965).

Tao, Mi-Hua and Morrison, Sherie L., *J. Immunol.,* 143(8) :2595–2601 (1989).

Takagi, H., Morinaga, Y., Tsuchiya, M., Ikemura, H. and Inouye, M. *Bio/technol.,* 6, 948–950 (1988).

Towbin, H., Stachelin, T. and Gordon, J. (1979) *Proc. Natl. Acad. Sci.,* 76, 4350–4354.

U.S. Pat. No. 4,554,101, Hopp, T. P., Nov.19, 1985.

Vandenbark, A. A., Hashim, G. and Offner, H. *Nature,* 331, 541–544 (1989). Viera, J. and Messing, J. in 'Methods in Enzymology', (Eds. R. Wu and L. Grossman, Academic Press, New York), 153, 3–11 (1987).

Ward, E. S., Güssow, D., Griffiths, A. D., Jones, P. T. and Winter, G. *Nature,* 341, 544–546 (1989).

Ward, E. S., *J. Mol. Biol.,* 224, 885–890 (1992).

Whitlow, M. and Filpula, D., in Methods: A Companion to Methods in Enzymology, Vol. 2, No. 2, p. 97–105 (1991)

Wraith, D. C., Smilek, D. E., Mitchell, D. J., Steinman, L. and McDevitt, H. O. *Cell,* 59, 247–255 (1989).

---

What is claimed is:

1. A method for producing an antibody with a decreased biological half life, comprising the steps of:
 a) obtaining a DNA segment that encodes an antibody with an Fc-hinge domain:
 b) introducing a mutation into said DNA segment encoding said antibody wherein expression of said DNA segment results in an antibody in which the Fc-hinge domain comprises an amino acid mutation in the CH2–CH3 domain interface region of the Fc-hinge fragment which results in impaired SpA binding relative to native Fc-hinge domain SpA binding; and
 c) expressing said antibody.

2. The method of claim 1, wherein the antibody is a recombinant antibody and the mutation is introduced into a DNA segment encoding the antibody by site-specific mutagenesis.

3. The method of claim 1, wherein the amino acid mutation lies in the region between about residue 253 and about residue 434 of SEQ ID NO:17.

4. The method of claim 3, wherein the mutation is an amino acid substitution at isoleucine 253, histidine 310, glutamine 311, histidine 433 or asparagine 434 of SEQ ID NO:17.

5. The method of claim 4, wherein alanine is substituted for histidine 310 of SEQ ID NO:17.

6. The method of claim 4, wherein asparagine is substituted for glutamine 311 of SEQ ID NO:17.

7. The method of claim 4, wherein alanine is substituted for histidine 433 of SEQ ID NO:17.

8. The method of claim 4, wherein glutamine is substituted for asparagine 434 of SEQ ID NO:17.

9. The method of claim 1, wherein said antibody is conjugated to an imaging agent.

10. The method of claim 9, wherein said imaging agent comprises a paramagnetic ion, a radioactive agent or a fluorogenic agent.

11. The method of claim 1, wherein said antibody is conjugated to a toxin.

12. The method of claim 11, wherein said toxin is a ricin A toxin.

* * * * *

UNITED STATES PATENT AND TRADEMARK OFFICE
CERTIFICATE OF CORRECTION

PATENT NO. : 6,165,745
DATED : December 26, 2000
INVENTOR(S) : Ward et al.

It is certified that error appears in the above-identified patent and that said Letters Patent is hereby corrected as shown below:

Title page,
In the priority information, please insert therefor -- This application is a continuation-in-part of PCT/US93/03895 filed April 26, 1994. --

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*